US011666581B2

(12) United States Patent
Pillow et al.

(10) Patent No.: US 11,666,581 B2
(45) Date of Patent: Jun. 6, 2023

(54) PROTAC ANTIBODY CONJUGATES AND METHODS OF USE

(71) Applicant: Genentech, Inc., South San Francisco, CA (US)

(72) Inventors: Thomas Pillow, San Francisco, CA (US); Jack Sadowsky, Dublin, CA (US); Leanna Staben, San Francisco, CA (US); Steven Staben, San Francisco, CA (US); Binqing Wei, Belmont, CA (US); Ingrid Wertz, South San Francisco, CA (US); Pragya Adhikari, Fremont, CA (US); Nicole Blaquiere, San Francisco, CA (US); Peter Dragovich, San Diego, CA (US); Wayne Fairbrother, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 1048 days.

(21) Appl. No.: 16/194,897

(22) Filed: Nov. 19, 2018

(65) Prior Publication Data

US 2019/0175612 A1     Jun. 13, 2019

Related U.S. Application Data

(63) Continuation of application No. PCT/US2017/033611, filed on May 19, 2017.

(60) Provisional application No. 62/339,257, filed on May 20, 2016.

(51) Int. Cl.
| | |
|---|---|
| *A61K 31/551* | (2006.01) |
| *A61K 47/54* | (2017.01) |
| *A61K 47/68* | (2017.01) |
| *A61K 47/65* | (2017.01) |
| *A61P 37/06* | (2006.01) |
| *A61P 35/00* | (2006.01) |
| *C07K 16/28* | (2006.01) |
| *C07K 16/32* | (2006.01) |
| *C12N 9/00* | (2006.01) |

(52) U.S. Cl.
CPC .......... *A61K 31/551* (2013.01); *A61K 47/545* (2017.08); *A61K 47/65* (2017.08); *A61K 47/68* (2017.08); *A61P 35/00* (2018.01); *A61P 37/06* (2018.01); *C07K 16/2827* (2013.01); *C07K 16/32* (2013.01); *C12N 9/93* (2013.01); *C12Y 203/02007* (2013.01)

(58) Field of Classification Search
CPC .... A61K 31/551; A61K 47/545; A61K 47/65; A61K 47/68; A61K 47/6803; A61K 47/6849; A61K 47/6855; A61P 35/00; A61P 37/06; C07K 16/2827; C07K 16/32; C12N 9/93; C12Y 203/02007
See application file for complete search history.

(56) References Cited

U.S. PATENT DOCUMENTS

| | | | | |
|---|---|---|---|---|
| 9,999,681 | B2 * | 6/2018 | Flygare | A61P 25/00 |
| 10,533,058 | B2 * | 1/2020 | Flygare | A61K 47/6851 |
| 2011/0256133 | A1 | 10/2011 | Dixit et al. | |
| 2016/0045607 | A1 | 2/2016 | Crew et al. | |

FOREIGN PATENT DOCUMENTS

| | | | |
|---|---|---|---|
| JP | 2017-529345 | 10/2017 | |
| WO | WO 2014/044622 | 3/2014 | |
| WO | WO-2014044622 A1 * | 3/2014 | ............. A61K 38/05 |
| WO | WO 2014/165506 | 10/2014 | |
| WO | WO 2015/071393 | 5/2015 | |
| WO | WO-2015071393 A1 * | 5/2015 | ........... A61K 31/551 |
| WO | WO-2015081282 A1 * | 6/2015 | ......... A61K 31/5386 |
| WO | WO-2015095227 A2 * | 6/2015 | ......... C07K 16/2863 |
| WO | WO 2017/201449 | 11/2017 | |

OTHER PUBLICATIONS

Buckley, et al., Angew Chem Int Ed Engl 2014 53(9): 2312-2330 (Year: 2014).*
Ali, et al., Journal of Mammary Gland Biology and Neoplasia 2000 vol. 5 No. 3 (Year: 2000).*
Pluta, et al., Neoplasma 2015 vol. 62, No. 4, pp. 666-673.*
Burke, et al., Bioconjugate chem 2009 20 1242-1250 (Year: 2009).*
Gruvberger-Saal, et al., Clin Cancer Res 2007 13(7)) (Year: 2007).*
Koniev, et al., Chem. Soc. Rev. 2015 vol. 44 5495-5551 (Year: 2015).*
Winter, G. et al. "Phthalimide conjugation as a strategy for vivo target protein degradation" Sciencexpress, doc 6, dated May 21, 2015, pp. 1-9.
International Search Report and Written Opinion for Application No. PCT/US2017/033611 dated Sep. 6, 2017.
Office Action for JP Application No. 2018-560504 dated Jun. 9, 2021.
Office Action and Search Report for CN Application No. 201780030893.6 dated Nov. 3, 2021.

* cited by examiner

*Primary Examiner* — Julie Wu
*Assistant Examiner* — John L Van Druff
(74) *Attorney, Agent, or Firm* — Alston & Bird LLP

(57) ABSTRACT

The subject matter described herein is directed to antibody-PROTAC conjugates (PACs), to pharmaceutical compositions containing them, and to their use in treating diseases and conditions where targeted protein degradation is beneficial.

22 Claims, 1 Drawing Sheet
Specification includes a Sequence Listing.

PROTAC ANTIBODY CONJUGATES AND METHODS OF USE

CROSS-REFERENCE TO RELATED APPLICATIONS

This application is a continuation of International Application No. PCT/US2017/033611, filed on May 19, 2017, which claims the benefit of priority to U.S. provisional Application No. 62/339,257 filed 20 May 2016, the contents of which applications are hereby incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named SEQLIST.TXT, created on Nov. 16, 2018, and having a size of 77 kilobytes and is filed concurrently with the specification. The sequence listing contained in this ASCII formatted document is part of the specification and is herein incorporated by reference in its entirety. SEQ ID NOs. 1-6 are intentionally omitted.

FIELD OF THE INVENTION

The subject matter described herein relates generally to antibody-(proteolysis-targeting chimera) (PROTAC) conjugate molecules that are useful for facilitating intracellular degradation of target proteins.

BACKGROUND

Cell maintenance and normal function requires controlled degradation of cellular proteins. For example, degradation of regulatory proteins triggers events in the cell cycle, such as DNA replication, chromosome segregation, etc. Accordingly, such degradation of proteins has implications for the cell's proliferation, differentiation and death.

While inhibitors of proteins can block or reduce protein activity in a cell, protein degradation in a cell can also reduce activity or remove altogether the target protein. Utilizing a cell's protein degradation pathway can, therefore, provide a means for reducing or removing protein activity. One of the cell's major degradation pathways is known as the ubiquitin-proteasome system. In this system, a protein is marked for degradation by the proteasome by ubiquitinating the protein. The ubiqitinization of the protein is accomplished by an E3 ubiquitin ligase that binds to a protein and adds ubiquitin molecules to the protein. The E3 ubiquitin ligase is part of a pathway that includes E1 and E2 ubiquitin ligases, which make ubiquitin available to the E3 ubiquitin ligase to add to the protein.

To harness this degradation pathway, PROTACs have been developed. PROTACs bring together an E3 ubiquitin ligase with a protein that is to be targeted for degradation. To facilitate a protein for degradation by the proteasome, the PROTAC is comprised of a group that binds to an E3 ubiquitin ligase and a group that binds to the protein one wishes to degrade. These groups are typically connected with a linker. This molecular construct can bring the E3 ubiquitin ligase in proximity with the protein so that it is ubiquitinated and marked for degradation.

There is an ongoing need in the art for enhanced and targeted delivery of PROTACs to cells that contain the protein target. Targeted delivery using antibody-PROTAC conjugates can enhance delivery of PROTACs to particular cells using the specificity of an antibody and can also enhance the pharmacokinetics of delivery of PROTACs to cells relative to other modes of administration of PROTACs, such as infusion.

SUMMARY OF THE INVENTION

In one aspect, the subject matter described herein is directed to a PROTAC-antibody conjugate (PAC) having the formula:

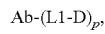

wherein, D is a PROTAC having the structure E3LB-L2-PB; wherein, E3LB is an E3 ligase binding group covalently bound to L2; L2 is a linker covalently bound to E3LB and PB; PB is a protein binding group covalently bound to L2; Ab is an antibody covalently bound to L1; L1 is a linker, covalently bound to Ab and to D; and p has a value from about 1 to about 8.

Another aspect of the subject matter described herein is a pharmaceutical composition comprising a PAC, and one or more pharmaceutically acceptable excipients.

Another aspect of the subject matter described herein is the use of a PAC in methods of treating conditions and diseases by administering to a subject a pharmaceutical composition comprising a PAC.

Another aspect of the subject matter described herein is a method of making a PAC.

Another aspect of the subject matter described herein is an article of manufacture comprising a pharmaceutical composition comprising a PAC, a container, and a package insert or label indicating that the pharmaceutical composition can be used to treat a disease or condition.

DETAILED DESCRIPTION

Figure 1:
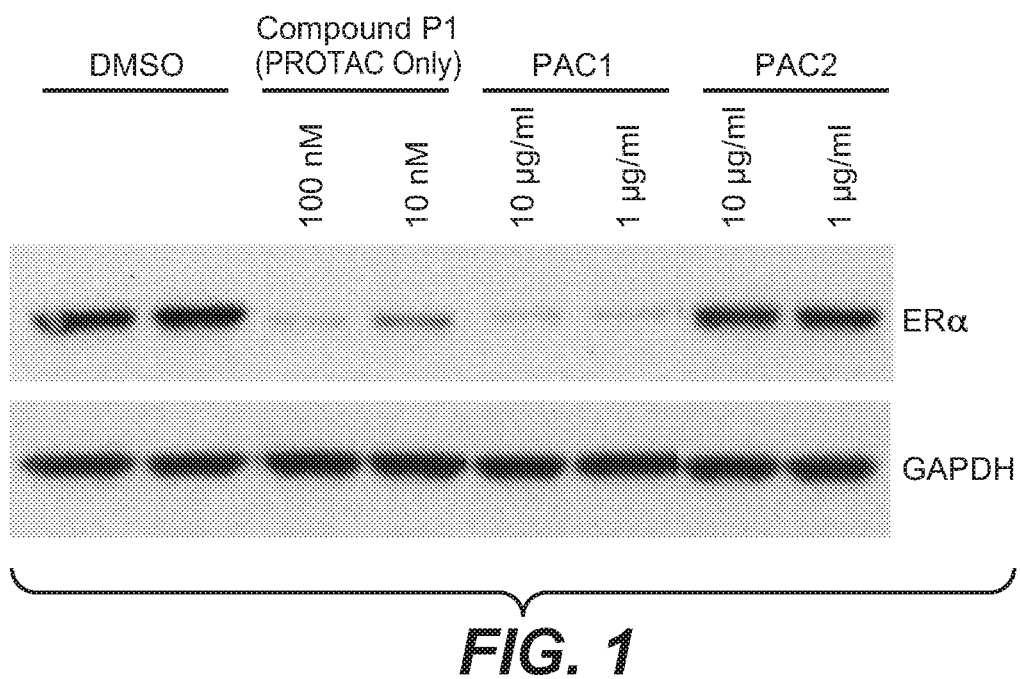
FIG. 1 shows the detection of ER-α by Western blot for PROTAC (without Ab), compound P1, and PROTAC-antibody conjugates (PACs) PAC1, and PAC2.

Disclosed herein, are antibody-proteolysis targeting chimera conjugates, referred to herein as PROTAC-Antibody conjugates (PACs), that are useful in targeted protein degradation, and the treatment of related diseases and disorders. The subject matter described herein utilizes antibody targeting to direct a PROTAC to a target cell or tissue. As described herein, connecting an antibody to a PROTAC to form a PAC has been shown to deliver the PROTAC to a target cell or tissue. As shown herein, e.g. in Examples 1 and 2, a cell that expresses an antigen can be targeted by an antigen specific PAC, whereby the PROTAC portion of the PAC is delivered intracellularly to the target cell. Also as shown herein, PACs that comprise an antibody directed to an antigen that is not found on the cell do not result in significant intracellualr delivery of the PROTAC to the cell.

Accordingly, the subject matter described herein is directed to PROTAC-antibody conjugate (PAC) compositions that result in the ubiquitination of a target protein and subsequent degradation of the protein. The compositions comprise an antibody covalently linked to a linker (L1), which is covalently linked at any available point of attachment to a PROTAC, in which the PROTAC comprises an E3 ubiquitin ligase binding (E3LB) moiety, wherein the E3LB moiety recognizes a E3 ubiquitin ligase protein and a protein binding moiety (PB) that recognizes a target protein. The subject matter described herein is useful for regulating protein activity, and treating diseases and conditions related to protein activity.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

The term "PROTAC" refers to proteolysis-targeting chimera molecules having generally three components, an E3 ubiquitin ligase binding group (E3LB), a linker L2, and a protein binding group (PB).

The terms "residue," "moiety" or "group" refers to a component that is covalently bound or linked to another component. For example a "residue of a PROTAC" refers to a PROTAC that is covalently linked to one or more groups such as a Linker L2, which itself can be optionally further linked to an antibody.

The term "covalently bound" or "covalently linked" refers to a chemical bond formed by sharing of one or more pairs of electrons.

The term "peptidomimetic" or PM as used herein means a non-peptide chemical moiety. Peptides are short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A peptidomimetic chemical moiety includes non-amino acid chemical moieties. A peptidomimetic chemical moiety may also include one or more amino acid that are separated by one or more non-amino acid chemical units. A peptidomimetic chemical moiety does not contain in any portion of its chemical structure two or more adjacent amino acids that are linked by peptide bonds.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology,* 5th Ed., Garland Publishing, New York). A target antigen generally has numerous binding sites, also called epitopes, recognized by CDRs (complementary determining regions) on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment(s)" as used herein comprises a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) *Protein Eng. Design & Sel.* 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the subject matter described herein may be made by the hybridoma method first described by Kohler et al (1975) *Nature,* 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352: 624-628; Marks et al (1991) *J. Mol. Biol.,* 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA*, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "intact antibody" as used herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used hererin means a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa ($\kappa$) and lambda ($\lambda$), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) *J. Immunol.* 161:4083-4090; Lund et al (2000) *Eur. J. Biochem.* 267: 7246-7256; US 2005/0048572; US 2004/0229310).

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain that are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. *Cancer Cell* 5:317-328 (2004)).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following. In certain embodiments, an antibody as described herein has dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "free cysteine amino acid" as used herein refers to a cysteine amino acid residue which has been engineered into a parent antibody, has a thiol functional group (—SH), and is not paired as an intramolecular or intermolecular disulfide bridge. The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "Linker", "Linker Unit", or "link" as used herein means a chemical moiety comprising a chain of atoms that covalently attaches a PROTAC moiety to an antibody, or a component of a PROTAC to another component of the PROTAC. In various embodiments, a linker is a divalent radical, specified as L1 or L2.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer.

A "patient population" refers to a group of cancer patients. Such populations can be used to demonstrate statistically significant efficacy and/or safety of a drug.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal may be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the subject matter described herein, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g., breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

By "monotherapy" is meant a therapeutic regimen that includes only a single therapeutic agent for the treatment of the cancer or tumor during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "cancer" and "cancerous" refer to or describe the physiological condition in mammals that is typically characterized by unregulated cell growth/proliferation. A "tumor" comprises one or more cancerous cells. Examples of cancer are provided elsewhere herein.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio ≥2.0. The term "HER2-positive cell" refers to a cell that expresses HER2 on its surface.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage IIB, and stage IIIA breast cancers.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor are known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease. A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TMI); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®, an antisense oligonucleotide); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., *Science,* 251: 430-432 (1991); WO 90/11294; Ianeway, *Nature,* 341: 482 (1989); and WO 91/01133); BAFF antagonists such as BAFF antibodies and BR3 antibodies and zTNF4 antagonists (for review, see Mackay and Mackay, *Trends Immunol.,* 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., *Science,* 261: 1328-30 (1993); Mohan et al., *J. Immunol.,* 154: 1470-80 (1995)) and CTLA4-Ig (Finck et al., *Science,* 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the subject matter described herein are used to delay development of a disease or to slow the progression of a disease.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

An "effective amount" of an agent, e.g., a pharmaceutical formulation, refers to an amount effective, at dosages and for periods of time necessary, to achieve the desired therapeutic or prophylactic result. For example, an effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a PAC, as well as salts thereof, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

As used herein, the term "plurality" refers to two or more conjugates. Each conjugate can be the same or different from any other conjugate in the plurality.

A "small molecule" or "small molecular compound" generally refers to an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of any length from two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like.

The term "alkenylene" refers to linear or branched-chain divalent hydrocarbon radical of any length from two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH═CH—), allyl (—$CH_2$CH═CH—), and the like.

The term "alkynyl" refers to a linear or branched monovalent hydrocarbon radical of any length from two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of any length from two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4, 5], [5, 5], [5, 6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4, 5], [5, 5], [5, 6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Other terms, definitions and abbreviations herein include: Wild-type ("WT"); Cysteine engineered mutant antibody ("thio"); light chain ("LC"); heavy chain ("HC"); 6-maleimidocaproyl ("MC"); maleimidopropanoyl ("MP"); valine-citrulline ("val-cit" or "vc"), alanine-phenylalanine ("ala-phe"), p-aminobenzyl ("PAB"), and p-aminobenzyloxycarbonyl ("PABC"); A118C (EU numbering)=A121C (Sequential numbering)=A114C (Kabat numbering) of heavy chain K149C (Kabat numbering) of light chain. Still additional definitions and abbreviations are provided elsehwere herein.

II. PROTAC-Antibody Conjugate (PAC)

The PROTAC-Antibody Conjugate (PAC) molecules described herein comprise an antibody conjugated via a linker (L1) to a PROTAC, wherein the PROTAC comprises a ubiquitin E3 ligase binding groug ("E3LB"), a linker ("L2") and a protein binding group ("PB"). The general formula of a PAC is:

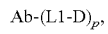

Ab-(L1-D)$_p$, wherein, D is PROTAC having the structure E3LB-L2-PB; wherein, E3LB is an E3 ligase binding group covalently bound to L2; L2 is a linker covalently bound to E3LB and PB; PB is a protein binding group covalently bound to L2; Ab is an antibody covalently bound to L1; L1 is a linker, covalently bound to Ab and to D; and p has a value from about 1 to about 50. The variable p reflects that an antibody can be connected to one or more L1-D groups. In one embodiment, p is from about 1 to 8. In another embodiment, p is about 2.

The following sections describe the components that comprise the PAC. To obtain a PAC having potent efficacy and a desirable therapeutic index, the following components are provided.

1. Antibody (Ab)

As described herein, antibodies, e.g., a monoclonal antibodies (mABs) are used to deliver a PROTAC to target cells, e.g., cells that express the specific protein that is targeted by the antibody. The antibody portion of a PAC can target a cell that expresses an antigen whereby the antigen specific PAC is delivered intracellularly to the target cell, typically through endocytosis While PACs that comprise an antibody directed to an antigen that is not found on the cell surface may result in less specific intracellular delivery of the PROTAC portion into the cell, the PAC may still undergo pinocytosis. The PACs and method of their use described herein advantageously utilize antibody recognition of the cellular surface and/or endocytosis of the PAC to deliver the PROTAC portion inside cells.

a. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

b. Library-Derived Antibodies

Antibodies for use in a PAC may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

c. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

d. Multispecific Antibodies

In certain embodiments, an antibody provided herein is a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same protein molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one protein molecule, whereas the second antigen-binding domain of the multispecific antibody may bind to another epitope on a different protein molecule, thereby cross-linking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both protein and any other antigen. In certain embodiments, one of the binding specificities is for protein and the other is for CD3. See, e.g., U.S. Pat. No. 5,821,337. In certain embodiments, bispecific antibodies may bind to two different epitopes of the same protein molecule. In certain embodiments, bispecific antibodies may bind to two different epitopes on two different protein molecules. Bispecific antibodies may also be used to localize cytotoxic agents to cells which express protein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. Nature Biotechnology (2007)).). The antibody or fragment herein also includes a "Dual Acting FAb" or "DAF" comprising an antigen binding site that binds to a target protein as well as another, different antigen (see, US 2008/0069820, for example).

e. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Plückthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

f. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

i. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved antibody-dependent cellular cytotoxicity (ADCC) or complement-dependent cytotoxicity (CDC).

TABLE 1

Amino acid substitutions.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |

TABLE 1-continued

Amino acid substitutions.

| Original Residue | Exemplary Substitutions | Preferred Substitutions |
|---|---|---|
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for antibody directed enzyme prodrug therapy (ADEPT)) or a polypeptide which increases the serum half-life of the antibody.

ii. Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as L-PROTAC groups, to create a PAC, as described further herein. In certain embodiments, any one or more of the following residues may be substituted with cysteine: V205 (Kabat numbering) of the light chain; A140 (EU numbering) of the heavy chain; L174 (EU numbering) of the heavy chain; Y373 (EU numbering) of the heavy chain; K149 (Kabat numbering) of the light chain; A118 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A 18C (EU numbering) cysteine substitution.

Cysteine engineered antibodies may be generated as described, e.g., in U.S. Pat. No. 7,521,541.

In certain embodiments, the antibody comprises one of the following heavy chain cysteine substitutions:

TABLE 2

HC Cysteine Substitutions.

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

TABLE 3

LC Cysteine Substitutions.

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | V | 205 | 205 |

A nonlimiting exemplary hu7C2.v2.2.LA light chain (LC) K149C THIOMAB™ antibody has the heavy chain and light chain amino acid sequences of SEQ ID NOs: 26 and 30, respectively. A nonlimiting exemplary hu7C2.v2.2.LA heavy chain (HC) A118C THIOMAB™ antibody has the heavy chain and light chain amino acid sequences of SEQ ID NOs: 31 and 25, respectively.

PACs include cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a THIOMAB™ antibody It should be noted that a single site mutation yields a single engineered cysteine residue in a ThioFab, while a single site mutation yields two engineered cysteine residues in a THIOMAB™ antibody due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies for use in a PAC are in the ranges of 0.6 to 1.0; 0.7 to 1.0; or 0.8 to 1.0.

To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249, Shen et al (2012) Nature Biotech., 30(2): 184-191; Junutula et al (2008) Jour of Immun. Methods 332:41-52). The engineered cysteine thiols may react with linker reagents or the Linker L-PROTAC intermediates described herein, which have thiol-reactive, electrophilic groups such as maleimides, activated disulfides (such as a 4-nitropyridyl disulfide), or alpha-halo amides to form a PAC with cysteine engineered antibodies (THIOMAB™ antibodies) and the PROTAC residue. The location of the PROTAC moiety can thus be designed, controlled, and known. PROTAC/antibody ratio ("PAR") can be controlled since the engineered cysteine thiol groups typically react with thiol-reactive linker reagents or linker L-PROTAC intermediates in high yield. Engineering an antibody to introduce a cysteine amino acid by substitution at a single site on the heavy or light chain gives two new cysteines on the symmetrical antibody. A PAR of about 2 can be achieved and near homogeneity of the conjugation product.

Cysteine engineered antibodies preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker L1 intermediates by reduction and reoxidation of intrachain disulfide groups.

iii. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

iv. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG, IgG2, IgG3 or IgG4 Fc region) comprising an amino acid modification (e.g. a substitution) at one or more amino acid positions.

In certain embodiments, the subject matter described herein is directed to an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., *Journal of Biological Chemistry* 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., *Journal of Biological Chemistry* 281(33): 23514-23524 (2006).

In certain embodiments, the YTE mutant provides a means to modulate antibody-dependent cell-mediated cytotoxicity (ADCC) activity of the antibody. In certain embodiments, the YTE0 mutant provides a means to modulate ADCC activity of a humanized IgG antibody directed against a human antigen. See, e.g., U.S. Pat. No. 8,697,650; see also Dall'Acqua et al., *Journal of Biological Chemistry* 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., *Journal of Biological Chemistry* 281(33): 23514-23524 (2006).

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

In certain embodiments, the proline at position 329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526).

In a specific embodiment the polypeptide comprising an Fc variant of a wild-type human Fc polypeptide comprises a triple mutation: an amino acid substitution at position Pro329, a L234A and a L235A mutation according to EU numbering (P329/LALA) (U.S. Pat. No. 8,969,526). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, *Nature* 322:738-40 (1988); U.S. Pat. Nos. 5,648,260; 5,624,821; and WO 94/29351 concerning other examples of Fc region variants.

g. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

h. Tumor-Associated Antigens

Antibodies, including but not limited to cysteine engineered antibodies, which may be useful in the PACs described herein in the treatment of cancer include, but are not limited to, antibodies against cell surface receptors and tumor-associated antigens (TAA). Certain tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to more specifically target cancer cells for destruction via antibody-based therapies.

Examples of tumor-associated antigens TAA include, but are not limited to, those listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA listed below are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, and/or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

i. Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in *Mather, Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al.,

*Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

Referring now to antibody affinity, in embodiments, the antibody binds to one or more tumor-associated antigens or cell-surface receptors selected from (1)-(53):

(1) BMPRIB (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB/pid=NP_001194.1—Cross-references: MIM:603248; NP_001194.1; AY065994

(2) E16 (LAT, SLC7A5, Genbank accession no. NM_003486)
Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+system), member 5/pid=NP_003477.3—*Homo sapiens* Cross-references: MIM:600182; NP_003477.3; NM_015923; NM_003486_1

Figure 2:
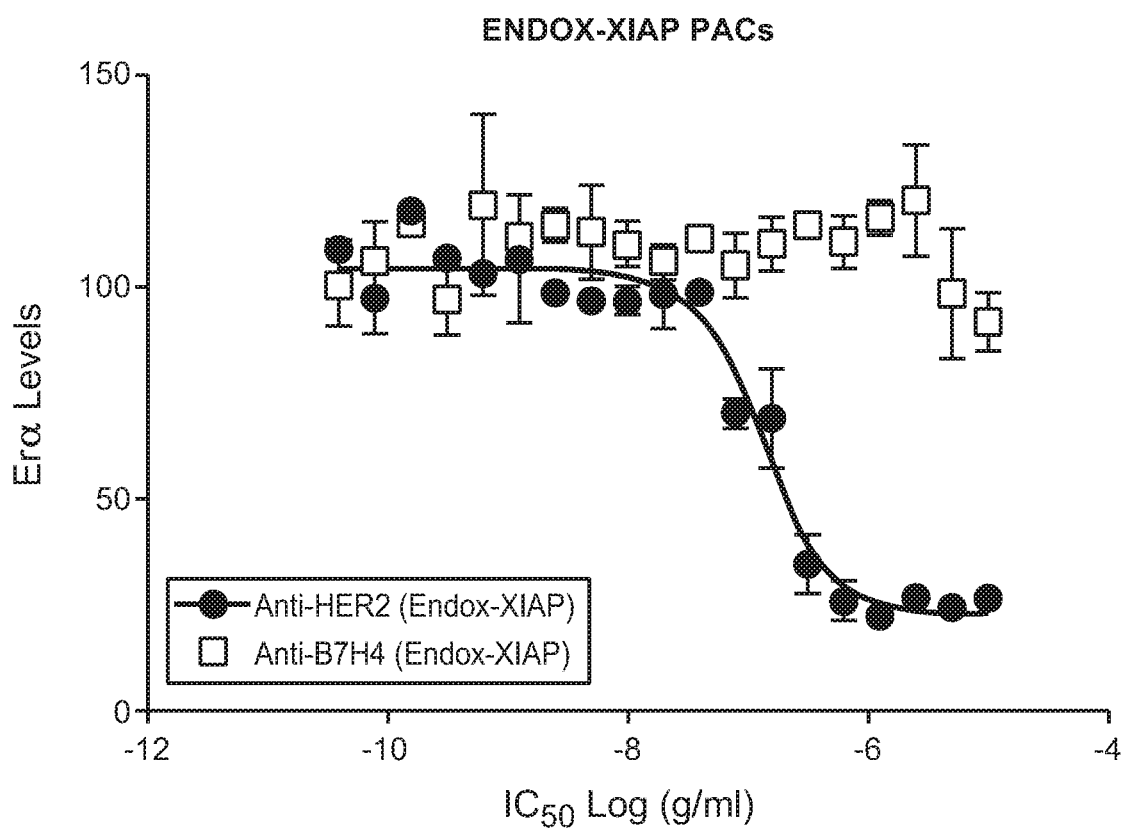
FIG. 2 depicts the quantitation of ERα as determined by fluorescence intensity for Endox-XIAP PACs treated for 3 days in an engineered HER2-MCF7 line. Media: 10% CS-FBS in phenol red free-RPMI.

(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25): 14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1

(4) 0772P (CA125, MUC 16, Genbank accession no. AF361486)
J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); U.S. Pat. No. 798,959. Cross-references: GI:34501467; AAK74120.3; AF361486_1

(5) MPF (MPF, MSLN, SMR, megakaryocyte potentiating factor, mesothelin, Genbank accession no. NM_005823)
Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424)
J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);
Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)
Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);
Cross-references: GI:37182378; AAQ88991.1; AY358628_1

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, sl-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004; (10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6): 1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

(17) HER2 (ErbB2, Genbank accession no. M11730)

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4);

Accession: P04626; EMBL; M11767; AAA35808.1. EMBL; M11761; AAA35808.1.

(18) NCA (CEACAM6, Genbank accession no. M18728);

Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);

Accession: P40199; Q14920; EMBL; M29541; AAA59915.1. EMBL; M18728;
(19) MDP (DPEP1, Genbank accession no. BC017023)
Proc. Natl. Acad. Sci. U.S.A. 99 (26): 16899-16903 (2002)); WO2003016475 (Claim 1); WO200264798 (Claim 33; Page 85-87); JP05003790 (FIG. 6-8); WO9946284 (FIG. 9);
Cross-references: MIM: 179780; AAH17023.1; BCO 17023_1
(20) IL20Rα (IL20Ra, ZCYTOR7, Genbank accession no. AF184971);
Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.
(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);
(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);
Cross-references: MIM:600997; NP_004433.2; NM_004442_1
(23) ASLG659 (B7h, Genbank accession no. AX092328)
US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;
(24) PSCA (Prostate stem cell antigen precursor, Genbank accession no. AJ297436)
Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);
Accession: 043653; EMBL; AF043498; AAC39607.1.
(25) GEDA (Genbank accession No. AY260763);
AAP14954 lipoma HMGIC fusion-partner-like protein/pid=AAP14954.1—*Homo sapiens* Species: *Homo sapiens* (human)
WO2003054152 (Claim 20); WO2003000842 (Claim 1); WO2003023013 (Example 3, Claim 20); US2003194704 (Claim 45);
Cross-references: GI:30102449; AAP14954.1; AY260763_1
(26) BAFF-R (B cell-activating factor receptor, BLyS receptor 3, BR3, Genbank accession No. AF116456); BAFF receptor/pid=NP_443177.1—*Homo sapiens*
Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);
Cross-references: MIM:606269; NP_443177.1; NM_052945_1; AF132600
(27) CD22 (B-cell receptor CD22-B isoform, BL-CAM, Lyb-8, Lyb8, SIGLEC-2, FLJ22814, Genbank accession No. AK026467);
Wilson et al (1991) J. Exp. Med. 173:137-146; WO2003072036 (Claim 1; FIG. 1); Cross-references: MIM:107266; NP_001762.1; NM_001771_1
(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58);

WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2) Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) FCRH5 (IRTA2, Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1 WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952; WO 2013/17705;

(41) TMEM46 (shisa homolog 2 (*Xenopus laevis*); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs. 168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ1856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) J. Clin. Invest. 75:756-56; Andrews et al., (1986) Blood 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC 12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

In an aspect, the antibody of the PAC may be an antibody that is directed to a protein that is found on numerous cells or tissue types. Examples of such antibodies include gD and EpCAM. In other words, a PAC can be used to deliver a PROTAC to many cells or tissues rather than specific cell types or tissue types as when using a using a targeted antibody.

As described herein, a PAC may comprise an antibody, e.g., an antibody selected from:

Anti-Ly6E Antibodies

In certain embodiments, a PAC can comprise anti-Ly6E antibodies. Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice (Mao, et al. (1996) *Proc. Natl. Acad. Sci. U.S.A.* 93:5910-5914). In some embodiments, the subject matter described herein provides a PAC comprising an anti-Ly6E antibody described in PCT Publication No. WO 2013/177055.

In some embodiments, the subject matter described herein provides a PAC comprising an anti-Ly6E antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the subject matter described herein provides a PAC comprising an antibody that comprises at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the subject matter described herein provides a PAC comprising an antibody that comprises at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In one embodiment, the antibody comprises (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, a PAC comprises an antibody comprising (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, the subject matter described herein provides a PAC comprising an antibody that comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In any of the above embodiments, an anti-Ly6E antibody of a PAC is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO:8 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs). Optionally, the anti-Ly6E antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-Ly6E antibody of a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity to the amino acid sequence of SEQ ID NO:7 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-Ly6E antibody comprises the VL sequence of SEQ ID NO: 7, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, a PAC comprising an anti-Ly6E antibody is provided, wherein the antibody comprises a VH as in any of the embodiments provided above, and a VL as in any of the embodiments provided above.

In one embodiment, a PAC is provided, wherein the antibody comprises the VH and VL sequences in SEQ ID NO: 8 and SEQ ID NO: 7, respectively, including post-translational modifications of those sequences.

In a further aspect, provided herein are PACs comprising antibodies that bind to the same epitope as an anti-Ly6E antibody provided herein. For example, in certain embodiments, a PAC is provided comprising an antibody that binds to the same epitope as an anti-Ly6E antibody comprising a VH sequence of SEQ ID NO: 8 and a VL sequence of SEQ ID NO: 7, respectively.

In a further aspect, an anti-Ly6E antibody of a PAC according to any of the above embodiments is a monoclonal antibody, including a human antibody. In one embodiment, an anti-Ly6E antibody of a PAC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, a PAC comprises an anti-Ly6E antibody comprising a heavy chain and a light chain comprising the amino acid sequences of SEQ ID NO: 16 and 15, respectively.

TABLE 4

Ly6E Antibody Sequences.

| SEQ ID NO | Description | Sequence |
|---|---|---|
| 7 | anti-Ly6E antibody hu9B12 v12 light chain variable region | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK |
| 8 | anti-Ly6E antibody hu9B12 v12 heavy chain variable region | EVQLVESGPA LVKPTQTLTL TCTVSGFSLT GYSVNWIRQPPGKAL EWLGMIWGDG STDYNSALKS RLTISKDTSK NQVVLTMTNM DPVDTATYYC ARDYYFNYAS WFAYWGQGTL VTVSS |

TABLE 4-continued

Ly6E Antibody Sequences.

| SEQ ID NO | Description | Sequence |
|---|---|---|
| 9 | anti-Ly6E antibody hu9B12 v12 HVR-L1 | SASQGISNYLN |
| 10 | anti-Ly6E antibody hu9B12 v12 HVR-L2 | YTSNLHS |
| 11 | anti-Ly6E antibody hu9B12 v12 HVR-L3 | QQYSELPWT |
| 12 | anti-Ly6E antibody hu9B12 v12 HVR-H1 | GFSLTGYSVN |
| 13 | anti-Ly6E antibody hu9B12 v12 HVR-H2 | MIWGDGSTDY NSALKS |
| 14 | anti-Ly6E antibody hu9B12 v12 HVR-H3 | DYYVNYASWFAY |
| 15 | anti-Ly6E antibody hu9B12 v12 K149C kappa light chain | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK RTVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 16 | anti-Ly6E antibody hu9B12 v12 IgG1 heavy chain | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

Anti-HER2 Antibodies

In certain embodiments, PACs comprise anti-HER2 antibodies. In one embodiment, an anti-HER2 antibody of a PAC comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment, an anti-HER2 antibody of a PAC comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment, an anti-HER2 antibody of a PAC comprises a humanized 7C2 anti-HER2 antibody. A humanized 7C2 antibody is an anti-HER2 antibody.

In some embodiments, described herein are PACs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In some embodiments, described herein are PACs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, described herein are PACs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In one aspect, described herein are PACs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24. In a further embodiment, the antibody comprises (a) HVR-H1 comprising the amino acid sequence of SEQ ID NO: 68; (b) HVR-H2 comprising the amino acid sequence of SEQ ID NO: 23, 27, or 28; and (c) HVR-H3 comprising the amino acid sequence of SEQ ID NO: 24 or 29. In a further embodiment, the antibody comprises (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In another aspect, described herein are PACs comprising an antibody that comprises at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, a PAC comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, 27, or 28, and (iii) HVR-H3 comprising an amino acid sequence selected from SEQ ID NO: 24 or 29; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21. In another aspect, a PAC comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, and (iii) HVR-H3 comprising an amino acid sequence selected from SEQ ID NO: 24; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, described herein are PACs comprising an antibody that comprises (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In another aspect, described herein are PACs comprising an antibody that comprises (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-HER2 antibody of a PAC is humanized. In one embodiment, an anti-HER2 antibody of a PAC comprises HVRs as in any of the above embodiments, and further comprises a human acceptor framework, e.g. a human immunoglobulin framework or a human consensus framework.

In another aspect, an anti-HER2 antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-HER2 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 22, (b) HVR-H2 comprising the amino acid sequence of SEQ ID NO: 23, and (c) HVR-H3 comprising the amino acid sequence of SEQ ID NO: 24.

In another aspect, an anti-HER2 antibody of a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In certain embodiments, a VL sequence having at least 90%, 91%, 92%, 93%, 94%, 95%, 96%, 97%, 98%, or 99% identity to the amino acid sequence of SEQ ID NO: 17 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 17. In certain embodiments, a total of 1 to 5 amino acids have been substituted, inserted and/or deleted in SEQ ID NO: 17. In certain embodiments, the substitutions, insertions, or deletions occur in regions outside the HVRs (i.e., in the FRs). Optionally, the anti-HER2 antibody comprises the VL sequence of SEQ ID NO: 17, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, a PAC comprising an anti-HER2 antibody is provided, wherein the antibody comprises a VH as in any of the embodiments provided above, and a VL as in any of the embodiments provided above.

In one embodiment, a PAC comprising an antibody is provided, wherein the antibody comprises the VH and VL sequences in SEQ ID NO: 18 and SEQ ID NO: 17, respectively, including post-translational modifications of those sequences.

In one embodiment, a PAC comprising an antibody is provided, wherein the antibody comprises the humanized 7C2.v2.2.LA (hu7C2) K149C kappa light chain sequence of SEQ ID NO: 30

In one embodiment, a PAC comprising an antibody is provided, wherein the antibody comprises the Hu7C2 A118C IgG1 heavy chain sequence of SEQ ID NO: 31

In a further aspect, provided herein are PACs comprising antibodies that bind to the same epitope as an anti-HER2 antibody provided herein. For example, in certain embodiments, a PAC is provided, comprising an antibody that binds to the same epitope as an anti-HER2 antibody comprising a VH sequence of SEQ ID NO: 18 and a VL sequence of SEQ ID NO: 17, respectively.

In a further aspect, an anti-HER2 antibody of a PAC according to any of the above embodiments is a monoclonal antibody, including a human antibody. In one embodiment, an anti-HER2 antibody of a PAC is an antibody fragment, e.g., a Fv, Fab, Fab', scFv, diabody, or F(ab')$_2$ fragment. In another embodiment, a PAC comprises an antibody that is a substantially full length antibody, e.g., an IgG1 antibody, IgG2a antibody or other antibody class or isotype as defined herein.

TABLE 5

Humanized 7C2 anti-HER2 antibody sequences.

| SEQ. ID NO. | Description | Sequence |
|---|---|---|
| 17 | Humanized 7C2.v2.2.LA ("hu7C2") light chain variable region | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IK |
| 18 | Hu7C2 heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS |
| 19 | Hu7C2 HVR-L1 | RASQSVSGSRFTYMH |
| 20 | Hu7C2 HVR-L2 | YASILES |
| 21 | Hu7C2 HVR-L3 | QHSWEIPPWT |
| 22 | Hu7C2 HVR-H1 | GYWMN |
| 23 | Hu7C2 HVR-H2 (Hu7C2.v2.1.S53L, S55A HVR-H2) | MIHPLDAEIRANQKFRD |
| 24 | Hu7C2 HVR-H3 | GTYDGGFEY |
| 25 | Humanized 7C2.v2.2.LA (hu7C2) kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 26 | Hu7C2 IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |

TABLE 5-continued

Humanized 7C2 anti-HER2 antibody sequences.

| SEQ. ID NO. | Description | Sequence |
|---|---|---|
| 27 | Hu7C2.v2.1.S53M HVR-H2 | MIHPMDSEIRANQKFRD |
| 28 | Hu7C2.v2.1.S53L HVR-H2 | MIHPLDSEIRANQKFRD |
| 29 | Hu7C2.v2.1.E101K HVR-H3 | GTYDGGFKY |
| 30 | Humanized 7C2.v2.2.LA (hu7C2) K149C kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWCVDNALQ SGNSQESVTE QDSKDSTYSL SSTLTLSKAD YEKHKVYACE VTHQGLSSPV TKSFNRGEC |
| 31 | Hu7C2 A118C IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSCS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 98 | exemplary human HER2 precursor protein, with signal sequence | MELAALCRWG LLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVPQQGF FCPDDAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV |

Anti-MUC 16 Antibodies

In certain embodiments, PACs comprise anti-MUC16 antibodies.

In some embodiments, described herein are PACs comprising an anti-MUC 16 antibody comprising at least one, two, three, four, five, or six HVRs selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33 and (f) HVR-L3 comprising the amino acid sequence of SEQ ID NO: 34.

In one aspect, described herein are PACs comprising an antibody that comprises at least one, at least two, or all three VH HVR sequences selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37. In a further embodiment, the antibody comprises (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37.

In another aspect, described herein are PACs comprising an antibody that comprises at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, a PAC comprises an antibody comprising (a) a VH domain comprising at least one, at least two, or all three VH HVR sequences selected from (i) HVR-H1 comprising the amino acid sequence of SEQ ID NO: 35, (ii) HVR-H2 comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, described herein are PACs comprising an antibody that comprises (a) HVR-H1 comprising the amino acid sequence of SEQ ID NO: 35 (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In any of the above embodiments, an anti-MUC16 antibody of a PAC is humanized.

In one embodiment, an anti-MUC16 antibody comprises HVRs as in any of the above embodiments, and further comprises a human acceptor framework, e.g. a human immunoglobulin framework or a human consensus framework.

In another aspect, an anti-MUC16 antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In certain embodiments, a VH sequence having at least 90%, 91%, 92%, 93%, 94%, 95%, 96%, 97%, 98%, or 99% identity to the amino acid sequence of SEQ ID NO: 39 contains substitutions (e.g., conservative substitutions), insertions, or deletions relative to the reference sequence, but an anti-MUC16 antibody comprising that sequence retains the ability to bind to MUC 16. In certain embodiments, a total of 1 to 10 amino acids have been substituted, inserted and/or deleted in SEQ ID NO: 39. In certain embodiments, a total of 1 to 5 amino acids have been substituted, inserted and/or deleted in SEQ ID NO: 39. In certain embodiments, substitutions, insertions, or deletions occur in regions outside the HVRs (i.e., in the FRs). Optionally, the anti-MUC 16 antibody comprises the VH sequence of SEQ ID NO: 39, including post-translational modifications of that sequence. In a particular embodiment, the VH comprises one, two or three HVRs selected from: (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 37.

In another aspect, an anti-MUC 16 antibody of a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 38. In certain embodiments, a VL sequence having at least 90%, 91%, 92%, 93%, 94%, 95%, 96%, 97%, 98%, or 99% identity to the amino acid sequence of SEQ ID NO:38 contains substitutions (e.g., conservative substitutions), insertions, or deletions relative to the reference sequence, but an anti-MUC16 antibody comprising that sequence retains the ability to bind to MUC 16. In certain embodiments, a total of 1 to 10 amino acids have been substituted, inserted and/or deleted in SEQ ID NO: 38. In certain embodiments, a total of 1 to 5 amino acids have been substituted, inserted and/or deleted in SEQ ID NO: 38. In certain embodiments, the substitutions, insertions, or deletions occur in regions outside the HVRs (i.e., in the FRs). Optionally, the anti-MUC16 antibody comprises the VL sequence of SEQ ID NO: 38, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, a PAC comprising an anti-MUC16 antibody is provided, wherein the antibody comprises a VH as in any of the embodiments provided above, and a VL as in any of the embodiments provided above.

In one embodiment, a PAC is provided, wherein the antibody comprises the VH and VL sequences in SEQ ID NO: 39 and SEQ ID NO: 38, respectively, including post-translational modifications of those sequences.

In a further aspect, provided herein are PACs comprising antibodies that bind to the same epitope as an anti-MUC 16 antibody provided herein. For example, in certain embodiments, a PAC is provided comprising an antibody that binds to the same epitope as an anti-MUC16 antibody comprising a VH sequence of SEQ ID NO: 39 and a VL sequence of SEQ ID NO: 38, respectively.

In a further aspect, an anti-MUC16 antibody of a PAC according to any of the above embodiments is a monoclonal antibody, including a human antibody. In one embodiment, an anti-MUC16 antibody of a PAC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 6

MUC16 Antibody Sequences.

| SEQ ID NO: | Description | Sequence |
|---|---|---|
| 32 | Anti-Muc16 antibody HVR-L1 | KASDLIHNWL A |
| 33 | Anti-Muc16 antibody HVR-L2 | YGATSLET |
| 34 | Anti-Muc16 antibody HVR-L3 | QQYWTTPFT |
| 35 | Anti-Muc16 antibody HVR-H1 | GYSITNDYAW N |
| 36 | Anti-Muc16 antibody HVR-H2 | GYISYSGYTT YNPSLKS |
| 37 | Anti-Muc16 antibody HVR-H3 | ARWASGLDY |
| 38 | Anti-Muc16 antibody light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 39 | Anti-Muc16 antibody heavy chain variable region | EVQLVESGGG LVQPGGSLRL SCAASGYSIT NDYAWNWVRQ APGKGLEWVG YISYSGYTTY NPSLKSRFTI SRDTSKNTLY LQMNSLRAED TAVYYCARWA SGLDYWGQGT LVTVSS |

Anti-STEAP-1 Antibodies

In certain embodiments, PACs comprise anti-STEAP-1 antibodies.

In some embodiments, described herein are PACs comprising an anti-STEAP-1 antibody comprising at least one, two, three, four, five, or six HVRs selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44 and (f) HVR-L3 comprising the amino acid sequence of SEQ ID NO: 45.

In one aspect, described herein are PACs comprising an antibody that comprises at least one, at least two, or all three VH HVR sequences selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42. In a further embodiment, the antibody comprises (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42.

In another aspect, described herein are PACs comprising an antibody that comprises at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, a PAC comprises an antibody comprising (a) a VH domain comprising at least one, at least two, or all three VH HVR sequences selected from (i) HVR-H1 comprising the amino acid sequence of SEQ ID NO: 40, (ii) HVR-H2 comprising the amino acid sequence of SEQ ID NO: 41, and (iii) HVR-H3 comprising an amino acid sequence selected from SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (c) HVR-L3 comprising the amino acid sequence of SEQ ID NO: 45.

In another aspect, described herein are PACs comprising an antibody that comprises (a) HVR-H1 comprising the amino acid sequence of SEQ ID NO: 40 (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In any of the above embodiments, an anti-STEAP-1 antibody of a PAC is humanized. In one embodiment, an anti-STEAP-1 antibody comprises HVRs as in any of the above embodiments, and further comprises a human acceptor framework, e.g. a human immunoglobulin framework or a human consensus framework.

In another aspect, an anti-STEAP-1 antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 46. In certain embodiments, a VH sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 46. In certain embodiments, a total of 1 to 5 amino acids have been substituted, inserted and/or deleted in SEQ ID NO: 46. In certain embodiments, substitutions, insertions, or deletions occur in regions outside the HVRs (i.e., in the FRs). Optionally, the anti-STEAP-1 antibody comprises the VH sequence of SEQ ID NO: 46, including post-translational modifications of that sequence. In a particular embodiment, the VH comprises one, two or three HVRs selected from: (a) HVR-H1 comprising the amino acid sequence of SEQ ID NO: 40, (b) HVR-H2 comprising the amino acid sequence of SEQ ID NO: 41, and (c) HVR-H3 comprising the amino acid sequence of SEQ ID NO: 42.

In another aspect, an anti-STEAP-1 antibody of an a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 47. In certain embodiments, a VL sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 47 In certain embodiments, a total of 1 to 5 amino acids have been substituted, inserted and/or deleted in SEQ ID NO: 47. In certain embodiments, the substitutions, insertions, or deletions occur in regions outside the HVRs (i.e., in the FRs). Optionally, the anti-STEAP-1 antibody comprises the VL sequence of SEQ ID NO: 47, including post-translational modifications of that sequence. In a particular embodiment, the VL comprises one, two or three HVRs selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, a PAC comprising an anti-STEAP-1 antibody is provided, wherein the antibody comprises a VH as in any of the embodiments provided above, and a VL as in any of the embodiments provided above.

In one embodiment, a PAC is provided, wherein the antibody comprises the VH and VL sequences in SEQ ID NO: 46 and SEQ ID NO: 47, respectively, including post-translational modifications of those sequences.

In a further aspect, provided herein are PACs comprising antibodies that bind to the same epitope as an anti-STEAP-1 antibody provided herein. For example, in certain embodiments, a PAC is provided comprising an antibody that binds to the same epitope as an anti-STEAP-1 antibody comprising a VH sequence of SEQ ID NO: 46 and a VL sequence of SEQ ID NO: 47, respectively.

In a further aspect, an anti-STEAP-1 antibody of a PAC according to any of the above embodiments is a monoclonal antibody, including a human antibody. In one embodiment, an anti-STEAP-1 antibody of a PAC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 7

STEAP Antibody Sequences.

| SEQ ID NO: | Description | Sequence |
|---|---|---|
| 40 | Anti-STEAP-1 HVR-H1 | GYSITSDYAW N |
| 41 | Anti-STEAP-1 HVR-H2 | GYISNSGSTS YNPSLKS |
| 42 | Anti-STEAP-1 HVR-H3 | ERNYDYDDYY YAMDY |
| 43 | Anti-STEAP-1 HVR-L1 | KSSQSLLYRS NQKNYLA |
| 44 | Anti-STEAP-1 HVR-L2 | WASTRES |
| 45 | Anti-STEAP-1 HYR-L3 | QQYYNYPRT |
| 46 | Anti-STEAP1 heavy chain variable region | EVQLVESGGG LVQPGGSLRL SCAVSGYSIT SDYAWNWVRQ APGKGLEWVG YISNSGSTSY NPSLKSRFTI SRDTSKNTLY LQMNSLRAED TAVYYCARER NYDYDDYYA MDYWGQGTLV TVSS |
| 47 | Anti-STEAP1 light chain variable region | DIQMTQSPSS LSASVGDRVT ITCKSSQSLL YRSNQKNYLA WYQQKPGKAP KLLIYWASTR ESGVPSRFSG SGSGTDFTLT ISSLQPEDFA TYYCQQYYNY PRTFGQGTKV EIK |

Anti-NaPi2b Antibodies

In certain embodiments, a PAC comprises anti-NaPi2b antibodies.

In some embodiments, described herein are PACs comprising an anti-NaPi2b antibody comprising at least one, two, three, four, five, or six HVRs selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52 and (f) HVR-L3 comprising the amino acid sequence of SEQ ID NO: 53.

In one aspect, described herein are PACs comprising an antibody that comprises at least one, at least two, or all three VH HVR sequences selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50. In a further embodiment, the antibody comprises (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50.

In another aspect, described herein are PACs comprising an antibody that comprises at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, a PAC comprises an antibody comprising (a) a VH domain comprising at least one, at least two, or all three VH HVR sequences selected from (i) HVR-H1 comprising the amino acid sequence of SEQ ID NO: 48, (ii) HVR-H2 comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, described herein are PACs comprising an antibody that comprises (a) HVR-H1 comprising the amino acid sequence of SEQ ID NO: 48 (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In any of the above embodiments, an anti-NaPi2b antibody of a PAC is humanized. In one embodiment, an anti-NaPi2b antibody comprises HVRs as in any of the above embodiments, and further comprises a human acceptor framework, e.g. a human immunoglobulin framework or a human consensus framework.

In another aspect, an anti-NaPi2b antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 54. In certain embodiments, a VH sequence having at least 90%, 91%, 92%, 93%, 94%, 95%, 96%, 97%, 98%, or 99% identity to the amino acid sequence of SEQ ID NO: 54 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO: 54. In certain embodiments, a total of 1 to 5 amino acids have been substituted, inserted and/or deleted in SEQ ID NO: 54. In certain embodiments, substitutions, insertions, or deletions occur in regions outside the HVRs (i.e., in the FRs). Optionally, the anti-NaPi2b antibody comprises the VH sequence of SEQ ID NO: 54, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-NaPi2b antibody of a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, or 99% identity to the amino acid sequence of SEQ ID NO: 55 contains substitutions (e.g., conservative substitutions), insertions, or deletions relative to the reference sequence, but an anti-NaPi2b antibody comprising that sequence retains the ability to bind to anti-NaPi2b. In certain embodiments, a total of 1 to 10 amino acids have been substituted, inserted and/or deleted in SEQ ID NO: 55. In certain embodiments, a total of 1 to 5 amino acids have been substituted, inserted and/or deleted in SEQ ID NO: 55. In certain embodiments, the substitutions, insertions, or deletions occur in regions outside the HVRs (i.e., in the FRs). Optionally, the anti-NaPi2b antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, a PAC comprising an anti-NaPi2b antibody is provided, wherein the antibody comprises a VH as in any of the embodiments provided above, and a VL as in any of the embodiments provided above.

In one embodiment, a PAC is provided, wherein the antibody comprises the VH and VL sequences in SEQ ID NO: 54 and SEQ ID NO: 55, respectively, including post-translational modifications of those sequences.

In a further aspect, provided herein are PACs comprising antibodies that bind to the same epitope as an anti-NaPi2b antibody provided herein. For example, in certain embodiments, a PAC is provided comprising an antibody that binds to the same epitope as an anti-NaPi2b antibody comprising a VH sequence of SEQ ID NO: 54 and a VL sequence of SEQ ID NO: 55, respectively.

In a further aspect, an anti-NaPi2b antibody of a PAC according to any of the above embodiments is a monoclonal antibody, including a human antibody. In one embodiment, an anti-NaPi2b antibody of a PAC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 8

NaPi2b Antibody Sequences.

| SEQ ID NO: | Description | Sequence |
|---|---|---|
| 48 | Anti-NaPi2b HVR-H1 10H1.11.4B | GFSFSDFAMS |
| 49 | Anti-NaPi2b HVR-H2 10H1.11.4B | ATIGRVAFHTYYPDSMKG |
| 50 | Anti-NaPi2b HVR-H3 10H1.11.4B | ARHRGFDVGHFDF |
| 51 | Anti-NaPi2b HVR-L1 10H1.11.4B | RSSETLVHSSGNTYLE |
| 52 | Anti-NaPi2b HVR-L2 | RVSNRFS |
| 53 | Anti-NaPi2b HVR-L3 10H1.11.4B | FQGSFNPLT |
| 54 | Anti-NaPi2b heavy chain variable region 10H1.11.4B $V_H$ | EVQLVESGGGLVQPGGSLRLSCAASGFSFSDFAMSWVRQAP GKGLEWVATIGRVAFHTYYPDSMKGRFTISRDNSKNTLYLQ MNSLRAEDTAVYYCARHRGFDVGHFDFWGQGTLVTVSS |
| 55 | Anti-NaPi2b light chain variable region 10H1.11.4B $V_L$ | DIQMTQSPSSLSASVGDRVTITCRSSETLVHSSGNTYLEWY QQKPGKAPKLLIYRVSNRFSGVPSRFSGSGSGTDFTLTISS LQPEDFATYYCFQGSFNPLTFGQGTKVEIKR |
| 64 | 10H1.11.4B Light Chain | DIQMTQSPSSLSASVGDRVTITCRSSETLVHSSGNTYLEWY QQKPGKAPKLLIYRVSNRFSGVPSRFSGSGSGTDFTLTISS LQPEDFATYYCFQGSFNPLTFGQGTKVEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGEC |
| 65 | 10H1.11.4B Heavy Chain | EVQLVESGGGLVQPGGSLRLSCAASGFSFSDFAMSWVRQAP GKGLEWVATIGRVAFHTYYPDSMKGRFTISRDNSKNTLYLQ MNSLRAEDTAVYYCARHRGFDVGHFDFWGQGTLVTVSSCST KGPSVFPLAPSSKSTSGGTAALGCLVKDYFPEPVTVSWNSG ALTSGVHTFPAVLQSSGLYSLSSVVTVPSSSLGTQTYICNV NHKPSNTKVDKKVEPKSCDKTHTCPPCPAPELLGGPSVFLF PPKPKDTLMISRTPEVTCVVVDVSHEDPEVKFNWYVDGVEV HNAKTKPREEQYNSTYRVVSVLTVLHQDWLNGKEYKCKVSN KALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGK |

Anti-CD79b Antibodies

In certain embodiments, PACs comprise anti-CD79b antibodies.

In some embodiments, described herein are PACs comprising an anti-CD79b antibody comprising at least one, two, three, four, five, or six HVRs selected from (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, described herein are PACs comprising an antibody that comprises at least one, at least two, or all three VH HVR sequences selected from (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60. In a further embodiment, the antibody comprises (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60.

In another aspect, described herein are PACs comprising an antibody that comprises at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, a PAC comprises an antibody comprising (a) a VH domain comprising at least one, at least two, or all three VH HVR sequences selected from (i) HVR-H1 comprising the amino acid sequence of SEQ ID NO: 58, (ii) HVR-H2 comprising the amino acid sequence of SEQ ID NO: 59, and (iii) HVR-H3 comprising an amino acid sequence selected from SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (c) HVR-L3 comprising the amino acid sequence of SEQ ID NO: 63.

In another aspect, described herein are PACs comprising an antibody that comprises (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In any of the above embodiments, an anti-CD79b antibody of a PAC is humanized. In one embodiment, an anti-CD79b antibody comprises HVRs as in any of the above embodiments, and further comprises a human acceptor framework, e.g. a human immunoglobulin framework or a human consensus framework.

In another aspect, an anti-CD79b antibody of a PAC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 56. In certain embodiments, a VH sequence having at least 90%, 91%, 92%, 93%, 94%, 95%, 96%, 97%, 98%, or 99% identity to the amino acid sequence of SEQ ID NO: 56 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 56. In certain embodiments, a total of 1 to 5 amino acids have been substituted, inserted and/or deleted in SEQ ID NO: 56. In certain embodiments, substitutions, insertions, or deletions occur in regions outside the HVRs (i.e., in the FRs). Optionally, the anti-CD79b antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 58, (b) HVR-H2 comprising the amino acid sequence of SEQ ID NO: 59, and (c) HVR-H3 comprising the amino acid sequence of SEQ ID NO: 60.

In another aspect, an anti-CD79b antibody of a PAC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, or 99% identity to the amino acid sequence of SEQ ID NO: 57 contains substitutions (e.g., conservative substitutions), insertions, or deletions relative to the reference sequence, but an anti-Ly6E antibody comprising that sequence retains the ability to bind to CD79b. In certain embodiments, a total of 1 to 10 amino acids have been substituted, inserted and/or deleted in SEQ ID NO: 57. In certain embodiments, a total of 1 to 5 amino acids have been substituted, inserted and/or deleted in SEQ ID NO: 57. In certain embodiments, the substitutions, insertions, or deletions occur in regions outside the HVRs (i.e., in the FRs). Optionally, the anti-CD79b antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, described herein are PACs comprising an anti-CD79b antibody is provided, wherein the antibody comprises a VH as in any of the embodiments provided above, and a VL as in any of the embodiments provided above.

In one embodiment, a PAC is provided, wherein the antibody comprises the VH and VL sequences in SEQ ID NO: 56 and SEQ ID NO: 57, respectively, including post-translational modifications of those sequences.

In a further aspect, provided herein are PACs comprising antibodies that bind to the same epitope as an anti-CD79b antibody provided herein. For example, in certain embodiments, a PAC is provided comprising an antibody that binds to the same epitope as an anti-CD79b antibody comprising a VH sequence of SEQ ID NO: 56 and a VL sequence of SEQ ID NO: 57, respectively.

In a further aspect, an anti-CD79b antibody of a PAC according to any of the above embodiments is a monoclonal antibody, including a human antibody. In one embodiment, an anti-CD79b antibody of a PAC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 9

CD79b Antibody Sequences.

| SEQ ID NO: | Description | Sequence |
|---|---|---|
| 56 | anti-CD79b huMA79bv28 heavy chain variable region | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSS |
| 57 | anti-CD79b huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |

TABLE 9-continued

CD79b Antibody Sequences.

| SEQ ID NO: | Description | Sequence |
|---|---|---|
| 58 | anti-CD79b huMA79bv28 HVR H1 | GYTFSSYWIE |
| 59 | anti-CD79b huMA79bv28 HVR H2 | GEILPGGGDTNYNEIFKG |
| 60 | anti-CD79b huMA79bv28 HVR H3 | TRRVPIRLDY |
| 61 | anti-CD79b huMA79bv28 HVR L1 | KASQSVDYEGDSFLN |
| 62 | anti-CD79b huMA79bv28 HVR L2 | AASNLES |
| 63 | anti-CD79b huMA79bv28 HVR L3 | QQSNEDPLT |

Anti-CD22 Antibodies

In certain embodiments, a PAC can comprise anti-CD22 antibodies, which comprise three light chain hypervariable regions (HVR-L1, HVR-L2 and HVR-L3) and three heavy chain hypervariable regions (HVR-H1, HVR-H2 and HVR-H3). In one embodiment, the anti-CD22 antibody of a PAC comprises three light chain hypervariable regions and three heavy chain hypervariable regions (SEQ ID NO: 66-71), the sequences of which are shown below. In one embodiment, the anti-CD22 antibody of a PAC comprises the variable light chain sequence of SEQ ID NO: 72 and the variable heavy chain sequence of SEQ ID NO: 73. In one embodiment, the anti-CD22 antibody of PACs of the present invention comprises the light chain sequence of SEQ ID NO: 74 and the heavy chain sequence of SEQ ID NO: 75:

TABLE 10

Anti-CD22 Antibodies.

| | | | |
|---|---|---|---|
| h10F4.V3.K149C HVR-L1 | RSSQSIVHSVGNTFLE | Seq ID No: 66 | |
| h10F4.V3.K149C HVR-L2 | KVSNRFS | Seq ID No: 67 | |
| h10F4.V3.K149C HVR-L3 | FQGSQFPYT | Seq ID No: 68 | |
| h10F4.V3.K149C HVR-H1 | GYEFSRSWMN | Seq ID No: 69 | |
| h10F4.V3.K149C HVR-H2 | RIYPGDGDTNYSGKFKG | Seq ID No: 70 | |
| h10F4.V3.K149C HVR-H3 | DGSSWDWYFDV | Seq ID No: 71 | |
| h10F4.V3.K149C $V_L$ | DIQMTQSPSSLSASVGDRVTITCRSSQSIVHSVGNTFLEWYQQK PGKAPKLLIYKVSNRFSGVPSRFSGSGSGTDFTLTISSLQPEDF ATYYCFQGSQFPYTFGQGTKVEIKR | Seq ID NO: 72 | |
| h10F4.V3.K149C $V_H$ | EVQLVESGGGLVQPGGSLRLSCAASGYEFSRSWMNWVRQAPGKG LEWVGRIYPGDGDTNYSGKFKGRFTISADTSKNTAYLQMNSLRA EDTAVYYCARDGSSWDWYFDVWGQGTLVTVSS | Seq ID NO: 73 | |
| h10F4.V3.K149C Light Chain | DIQMTQSPSSLSASVGDRVTITCRSSQSIVHSVGNTFLEWYQQK P GKAPKLLIYKVSNRFSGVPSRFSGSGSGTDFTLTISSLQPEDFA TYYCFQGSQFPYTFGQGTKVEIKRTVAAPSVFIFPPSDEQLKSG TASVVCLLNNFYPREAKVQWCVDNALQSGNSQESVTEQDSKDST YSLSSTLTLSKADYEKHKVYACEVTHQGLSSPVTKSFNRGEC | Seq ID NO: 74 | |

TABLE 10-continued

Anti-CD22 Antibodies.

| | | |
|---|---|---|
| h10F4.V3.K149C Heavy Chain | EVQLVESGGGLVQPGGSLRLSCAASGYEFSRSWMNWVRQAPGKG LEWVGRIYPGDGDTNYSGKFKGRFTISADTSKNTAYLQMNSLRA EDTAVYYCARDGSSWDWYFDVWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVY TLPPSREEMTKNQVSLTCLVKGFYPSDIAVEWESNGQPENNYKT TPPVLDSDGSFFLYSKLTVDKSRW QQGNVFSCSVMHEALHNHYTQKSLSLSPGK | SEQ ID NO: 75 |

Anti-CD33 Antibodies

In certain embodiments, a PAC can comprise anti-CD33 antibodies, which comprise three light chain hypervariable regions and three heavy chain hypervariable regions, the sequences (SEQ ID NO:76-81) of which are shown below. In one embodiment, the anti-CD33 antibody of a PAC comprises the variable light chain sequence of SEQ ID NO: 82 and the variable heavy chain sequence of SEQ ID NO: 83.

TABLE 11

| | | |
|---|---|---|
| 15G15.33- HVR L1 | RSSQSLLHSNGYNYLD | SEQ ID NO: 76 |
| 15G15.33- HVR L2 | LGVNSVS | SEQ ID NO: 77 |
| 15G15.33- HVR L3 | MQALQTPWT | SEQ ID NO: 78 |
| 15G15.33- HVR H1 | NHAIS | SEQ ID NO: 79 |
| 15G15.33- HVR H2 | GIIPIFGTANYAQKFQG | SEQ ID NO: 80 |
| 15G15.33- HVR H3 | EWADVFDI | SEQ ID NO: 81 |
| 15G15.33 $V_L$ | EIVLTQSPLSLPVTPGEPASISCRSSQSLLHSNGYNYLDWYLQKPGQS PQLLIYLGVNSVSGVPDRFSGSGSGTDFTLKISRVEAEDVGVYYCMQA LQTPWTFGQGTKVEIK | SEQ ID NO: 82 |
| 15G15.33 $V_H$ | QVQLVQSGAEVKKPGSSVKVSCKASGGIFSNHAISWVRQAPGQGLEWM GGIIPIFGTANYAQKFQGRVTITADESTSTAFMELSSLRSEDTAVYYC AREWADVFDIWGQGTMVIVSS | SEQ ID NO: 83 |

In one embodiment, the anti-CD33 antibody of a PAC comprises the light chain sequence of SEQ ID NO: 84 and the heavy chain sequence of SEQ ID NO: 85. In one embodiment, the anti-CD33 antibody of a PAC comprises three light chain hypervariable regions and three heavy chain hypervariable regions, the sequences (Seq ID NO: 84-89) of which are shown below. In one embodiment, the anti-CD33 antibody of a PAC comprises the variable light chain sequence of SEQ ID NO: 90 and the variable heavy chain sequence of SEQ ID NO: 91. In one embodiment, the anti-CD33 antibody of PAC comprises the variable light chain sequence of SEQ ID NO: 92 and the variable heavy chain sequence of SEQ ID NO: 93. In one embodiment, the anti-CD33 antibody of the present invention comprises the variable light chain sequence of SEQ ID NO: 94 and the variable heavy chain sequence of SEQ ID NO: 95. In one embodiment, the anti-CD33 antibody of the present invention comprises the variable light chain sequence of SEQ ID NO: 96 and the variable heavy chain sequence of SEQ ID NO: 97.

TABLE 12

| | | |
|---|---|---|
| 9C3-HVR L1 | RASQGIRNDLG | Seq ID NO: 84 |
| 9C3-HVR L2 | AASSLQS | Seq ID NO: 85 |

TABLE 12-continued

| | | |
|---|---|---|
| 9C3-HVR L3 | LQHNSYPWT | Seq ID NO: 86 |
| 9C3-HVR H1 | GNYMS | Seq ID NO: 87 |
| 9C3-HVR H2 | LIYSGDSTYYADSVKG | Seq ID NO: 88 |
| 9C3-HVR H3 | DGYYVSDMVV | Seq ID NO: 89 |
| 9C3 $V_L$ | DIQMTQSPSSLSASVGDRVTITCRASQGIRNDLGWYQQKP GKAPKRLIYAASSLQSGVPSRFSGSGSGTEFTLTISSLQP EDFATYYCLQHNSYPWTFGQGTKLEIK | Seq ID NO: 90 |
| 9C3 $V_H$ | EVQLVESGGALIQPGGSLRLSCVASGFTISGNYMSWVRQA PGKGLEWVSLIYSGDSTYYADSVKGRFNISRDISKNTVYL QMNSLRVEDTAVYYCVRDGYYVSDMVVWGKGTTVTVSS | Seq ID NO: 91 |
| 9C3.2 $V_L$ | DIQMTQSPSSLSASVGDRVTITCRASQGIRNDLGWYQQKP GKAPKRLIYAASSLQSGVPSRFSGSGSGTEFTLTISSLQP EDFATYYCLQHNSYPWTFGQGTKLEIK | Seq ID NO: 92 |
| 9C3.2 $V_H$ | EVQLVESGGALIQPGGSLRLSCVASGFTISGNYMSWVRQA PGKGLEWVSLIYSGDSTYYADSVKGRFTISRDISKNTVYL QMNSLRVEDTAVYYCVRDGYYVSDMVVWGKGTTVTVSS | Seq ID NO: 93 |
| 9C3.3 $V_L$ | DIQMTQSPSSLSASVGDRVTITCRASQGIRNDLGWYQQKP GKAPKRLIYAASSLQSGVPSRFSGSGSGTEFTLTISSLQP EDFATYYCLQHNSYPWTFGQGTKLEIK | Seq ID NO: 94 |
| 9C3.3 $V_H$ | EVQLVESGGALIQPGGSLRLSCVASGFTISGNYMSWVRQA PGKGLEWVSLIYSGDSTYYADSVKGRFSISRDISKNTVYL QMNSLRVEDTAVYYCVRDGYYVSDMVVWGKGTTVTVSS | Seq ID NO: 95 |
| 9C3.4 $V_L$ | DIQMTQSPSSLSASVGDRVTITCRASQGIRNDLGWYQQKP GKAPKRLIYAASSLQSGVPSRFSGSGSGTEFTLTISSLQP EDFATYYCLQHNSYPWTFGQGTKLEIK | Seq ID NO: 96 |
| 9C3.4 $V_H$ | EVQLVESGGALIQPGGSLRLSCVASGFTISGNYMSWVRQA PGKGLEWVSLIYSGDSTYYADSVKGRFAISRDISKNTVYL QMNSLRVEDTAVYYCVRDGYYVSDMVVWGKGTTVTVSS | Seq ID NO: 97 |

Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20 TM; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Linkers (L1)

As described herein, a "linker" (L1) is a bifunctional or multifunctional moiety that can be used to link one or more PROTAC moieties (D) to an antibody (Ab) to form a PAC. In some embodiments, PACs can be prepared using a L1 having reactive functionalities for covalently attaching to the PROTAC and to the antibody. For example, in some embodiments, a cysteine thiol of an antibody (Ab) can form a bond with a reactive functional group of a linker or a linker L-PROTAC group to make a PAC. Particularly, the chemical structure of the linker can have significant impact on both the efficacy and the safety of a PAC (Ducry & Stump, Bioconjugate Chem, 2010, 21, 5-13). Choosing the right linker influences proper drug delivery to the intended cellular compartment of target cells.

Linkers can be generally divided into two categories: cleavable (such as peptide, hydrzone, or disulfide) or non-cleavable (such as thioether). Peptide linkers, such as Valine-Citrulline (Val-Cit), that can be hydrolyzed by lysosomal enzymes (such as Cathepsin B) have been used to connect the drug with the antibody (U.S. Pat. No. 6,214,345). They have been particularly useful, due in part to their relative stability in systemic circulation and the ability to efficiently release the drug in tumor. However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for linker L1 that can be cleaved by lysosomal enzymes.

a. Peptidomimetic Linkers

Provided herein are different types of non-peptide, peptidomimetic linkers for PAC that are cleavable by lysosomal enzymes. For example, the amide bond in the middle of a dipeptide (e.g. Val-Cit) was replaced with an amide mimic; and/or entire amino acid (e.g., valine amino acid in Val-Cit dipeptide) was replaced with a non-amino acid moiety (e.g., cycloalkyl dicarbonyl structures (for example, ring size=4 or 5)).

When L1 is a peptidomimetic linker, it is represented by the following formula

-Str-(PM)-Sp-, wherein:
Str is a stretcher unit covalently attached to Ab;
Sp is a bond or spacer unit covalently attached to a PROTAC moiety; and PM is a non-peptide chemical moiety selected from the group consisting of:

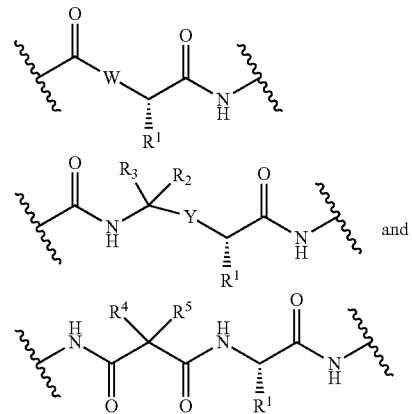
and

W is —NH-heterocycloalkyl- or heterocycloalkyl;
Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;
each $R^1$ is independently $C_1$-$C_{10}$alkyl, $C_1$-$C_{10}$alkenyl, ($C_1$-$C_{10}$alkyl)NHC(NH)$NH_2$ or ($C_1$-$C_{10}$alkyl)NHC(O)$NH_2$;
$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and
$R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ may form a $C_3$-$C_7$cycloalkyl ring.

It is noted that L1 may be connected to the PROTAC through any of the E3LB, L2, or PB groups.

In embodiments, Y is heteroaryl; $R^4$ and $R^5$ together form a cyclobutyl ring.

In embodiments, Y is a moiety selected from the group consisting of:

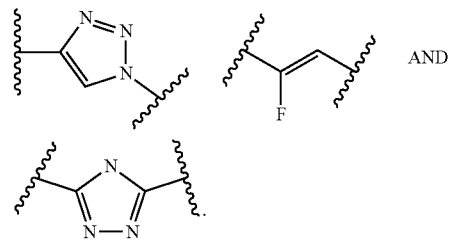

AND

In embodiments, Str is a chemical moiety represented by the following formula:

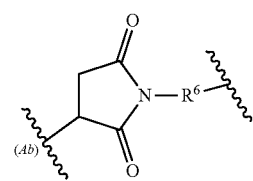

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-

$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

In embodiments, Str has the formula:

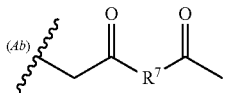

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) and N($R^c$)—($C_2$-$C_6$alkylene); where each $R^c$ is independently H or $C_1$-$C_6$ alkyl; Sp is —Ar—$R^b$—, wherein Ar is aryl or heteroaryl, $R^b$ is ($C_1$-$C_{10}$alkylene)O— or Sp-$C_1$-$C_6$alkylene-C(O)NH—.

In embodiments, L1 is a non-peptide chemical moiety represented by the following formula

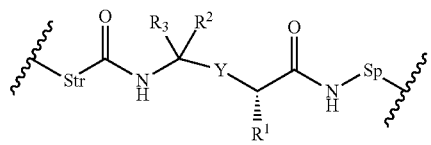

$R^1$ is $C_1$-$C_6$alkyl, $C_1$-$C_6$alkenyl, ($C_1$-$C_6$alkyl)NHC(NH)NH$_2$ or ($C_1$-$C_6$alkyl)NHC(O)NH$_2$;
$R^3$ and $R^2$ are each independently H or $C_1$-$C_{10}$alkyl.

In embodiments, L1 is a non-peptide chemical moiety represented by the following formula

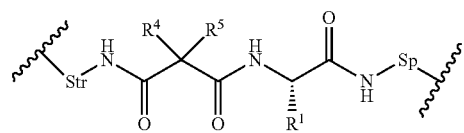

$R^1$ is $C_1$-$C_6$ alkyl, ($C_1$-$C_6$alkyl)NHC(NH)NH$_2$ or ($C_1$-$C_6$alkyl)NHC(O)NH$_2$;
$R^4$ and $R^5$ together form a $C_3$-$C_7$cycloalkyl ring.

In embodiments, L1 is a non-peptide chemical moiety represented by the following formula

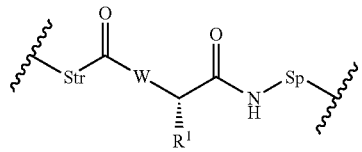

$R^1$ is $C_1$-$C_6$alkyl, ($C_1$-$C_6$alkyl)NHC(NH)NH$_2$ or ($C_1$-$C_6$alkyl)NHC(O)NH$_2$ and W is as defined above.

In some embodiments, the linker may be a peptidomimetic linker such as those described in WO2015/095227, WO2015/095124 or WO2015/095223.

b. Non-Peptidomimetic Linkers

In an aspect, a Linker L1 forms a disulfide bond with the antibody. In an aspect, the linker has the structure:

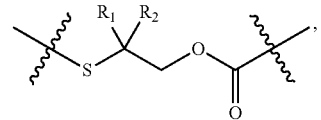

wherein, $R^1$ and $R^2$ are independently selected from H and $C_1$-$C_6$ alkyl, or $R^1$ and $R^2$ form a 3, 4, 5, or 6-membered cycloalkyl or heterocyclyl group. The linker is covalently bound to an antibody and a PROTAC as follows:

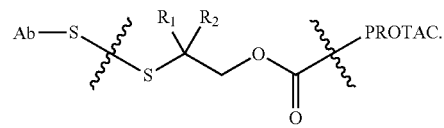

In one aspect the carbonyl group of the linker is connected to an amine group in the PROTAC. It is also noted that the sulfur atom connected to Ab is a sulfur group from a cysteine in the antibody. In another aspect, a linker L1 has a functionality that is capable of reacting with a free cysteine present on an antibody to form a covalent bond. Nonlimiting examples of such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Examples of such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting examples of such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a PROTAC. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula:

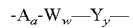

wherein A is a "stretcher unit", and a is an integer from 0 to 1; W is an "amino acid unit", and w is an integer from 0 to 12; Y is a "spacer unit", and y is 0, 1, or 2. Exemplary embodiments of such linkers are described in U.S. Pat. No. 7,498,298.

In some embodiments, a linker component comprises a "stretcher unit" that links an antibody to another linker component or to a PROTAC moiety. Nonlimiting exemplary stretcher units are shown below (wherein the wavy line indicates sites of covalent attachment to an antibody, PROTAC, or additional linker components):

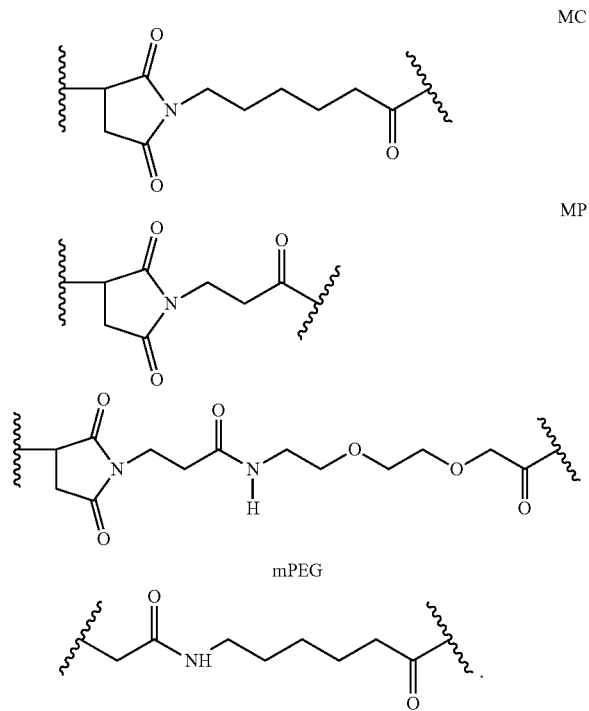

3. PROTAC ("D")

Useful PROTACs have the general formula described above. Particular PROTACs are described in U.S. Pat. No. 7,208,157, WO2013/106643, WO2013/106646, and WO2015/160845. PROTACs include those having the following components.

a. E3 Ubiquitin Ligases Binding Groups (E3LB)

E3 ubiquitin ligases (of which over 600 are known in humans) confer substrate specificity for ubiquitination. There are known ligands which bind to these ligases. As described herein, an E3 ubiquitin ligase binding group is a peptide or small molecule that can bind an E3 ubiquitin ligase.

Specific E3 ubiquitin ligases include: von Hippel-Lindau (VHL); cereblon, XIAP, E3A; MDM2; Anaphase-promoting complex (APC); UBR5 (EDD1); SOCS/BC-box/eloBC/CUL5/RING; LNXp80; CBX4; CBLL1; HACE1; HECTD1; HECTD2; HECTD3; HECW1; HECW2; HERC1; HERC2; HERC3; HERC4; HUWE1; ITCH; NEDD4; NEDD4L; PPIL2; PRPF19; PIAS1; PIAS2; PIAS3; PIAS4; RANBP2; RNF4; RBX1; SMURF1; SMURF2; STUB1; TOPOR5; TRIP12; UBE3A; UBE3B; UBE3C; UBE4A; UBE4B; UBOX5; UBR5; WWP1; WWP2; Parkin; A20/TNFAIP3; AMFR/gp78; ARA54; beta-TrCP1/BTRC; BRCA1; CBL; CHIP/STUB1; E6; E6AP/UBE3A; F-box protein 15/FBXO15; FBXW7/Cdc4; GRAIL/RNF128; HOIP/RNF31; cIAP-1/HIAP-2; cIAP-2/HIAP-1; cIAP (pan); ITCH/AIP4; KAP1; MARCH8; Mind Bomb 1/MIB1; Mind Bomb 2/MIB2; MuRF1/TRIM63; NDFIP1; NEDD4; NleL; Parkin; RNF2; RNF4; RNF8; RNF168; RNF43; SART1; Skp2; SMURF2; TRAF-1; TRAF-2; TRAF-3; TRAF-4; TRAF-5; TRAF-6; TRIM5; TRIM21; TRIM32; UBR5; and ZNRF3.

The following Tables 13-27 list certain E3 ligases.

TABLE 13

E3 Ligases, HECT type.
HECT

| Name | UniProt | Type | Genbank | LL | Refseq | Unigene | Domains |
|---|---|---|---|---|---|---|---|
| EDD/HYD | O95071 | HECT | AF006010 | 51366 | NM_015902 | Hs.492445 | HECT; UBA; ZF_UBR1; pab |
| FLJ21156 | Q5T447 | HECT | AK096462 | 79654 | NM_024602 | Hs.525084 | DOC1; HECT |
| HACE1/KIAA1320 | Q5VU99 | HECT | BC034982 | 57531 | NM_020771 | Hs.434340 | Ank; HECT |
| HECTD1 | Q9ULT8 | HECT | BC011658 | 25831 | NM_015382 | Hs.210850 | HECT; MIB_HERC2; |
| HECTD2 | Q5U5R9 | HECT | BC040187 | 143279 | NM_182765; NM_173497 | Hs.66378 | HECT |
| HECW1/NEDL1 | Q9HCC7 | HECT | AB048365 | 23072 | NM_015052 | Hs.164453 | C2; HECT; WW |
| HECW2/KIAA1301 | Q9P2P5 | HECT | AB037722 | 57520 | NM_020760 | Hs.314436 | C2; HECT; WW |
| HERC1/P532 | Q15751 | HECT | U50078 | 8925 | NM_003922 | Hs.210385 | HECT; SPRY; WD; RCC |
| HERC2 | O95714 | HECT | AF071172 | 8924 | NM_004667 | Hs.434890 | DOC1; HECT; HERC2; MIB_HERC2; UBA; ZZ; RCC |
| HERC3 | Q15034 | HECT | D25215 | 8916 | NM_014606 | Hs.35804 | HECT; RCC |
| HERC4 | Q5VXS9 | HECT | BC039600 | 26091 | NM_015601 | Hs.51891 | HECT; RCC |
| HERC5/CEBP1 | Q9UII4 | HECT | AB027289 | 51191 | NM_016323 | Hs.26663 | HECT; RCC |
| HERC6 | Q8IVU3 | HECT | BC042047 | 55008 | NM_017912 | Hs.529317 | HECT; RCC |
| ITCH | Q96J02 | HECT | AB056663 | 83737 | NM_031483 | Hs.472509 | C2; HECT; WW |
| KIAA0317 | O15033 | HECT | AB002315 | 9870 | NM_014821 | Hs.497417 | HECT |
| KIAA0614/FLJ30092 | Q9Y4D8 | HECT | AB014514 | none | XM_497354 | Hs.7314 | HECT; SPRY |
| KIAA1333/FLJ20333 | Q9NXC0 | HECT | AK000340 | 55632 | NM_017769 | Hs.509008 | HECT; RF |
| NEDD4 | P46934 | HECT | D42055 | 4734 | NM_198400; NM_006154 | Hs.1565 | C2; HECT; WW |
| NEDD4L | Q7Z5F1 | HECT | AY112985 | 23327 | NM_015277 | Hs.185677 | C2; HECT; WW |

TABLE 13-continued

E3 Ligases, HECT type.
HECT

| Name | UniProt | Type | Genbank | LL | Refseq | Unigene | Domains |
|---|---|---|---|---|---|---|---|
| SMURF1 | Q9HCE7 | HECT | AF199364 | 57154 | NM_020429; NM_181349 | Hs.189329 | C2; HECT; WW |
| SMURF2 | Q9HAU4 | HECT | AF310676 | 64750 | NM_022739 | Hs.515011 | C2; HECT; WW |
| TRIP12 | Q14669 | HECT | D28476 | 9320 | NM_004238 | Hs.368985 | HEAT/ARM; HECT; WWE |
| UBE3A/E6AP | Q05086 | HECT | X98031 | 7337 | NM_000462; NM_130838; NM_130839 | Hs.22543 | HECT |
| UBE3B | Q9BXZ4 | HECT | AF251046 | 89910 | NM_130466; NM_183415; NM_183414 | Hs.374067 | HECT; IQ |
| UBE3C/KIAA0010 | Q15386 | HECT | D13635 | 9690 | NM_014671 | Hs.118351 | HECT; IQ; IRF3CT |
| UREB1/LASU1 | Q7Z6Z7 | HECT | CR456813 | none | NM_031407 | Hs.136905 | HECT; UBA; UIM; WWE |
| WWP1 | Q9H0M0 | HECT | AY043361 | 11059 | NM_007013 | Hs.533440 | C2; HECT; WW |
| WWP2 | O00308 | HECT | BC064531 | 11060 | NM_007014; NM_199423; NM_199424 | Hs.408458 | HECT; WW |

TABLE 14

E3 Ligases, RING type.

| Name | UniProt | Type | Genbank | LL | Refseq | Unigene | Domains |
|---|---|---|---|---|---|---|---|
| AMFR | Q9UKV5 | RING | AF124145 | 267 | NM_138958; NM_001144 | Hs.295137 | RF; CUE1; DER3 |
| ANAPC11 | Q9NYG5 | RING | AF247565 | 51529 | NM_001002249; NM_016476; NM_001002246; NM_001002248; NM_001002244; NM_001002247; NM_001002245 | Hs.534456 | RF |
| BARD1 | Q99728 | RING | U76638 | 580 | NM_000465 | Hs.54089 | RF; Ank; BRCT |
| BFAR/BAR | Q9NZS9 | RING | BC003054 | 51283 | NM_016561 | Hs.435556 | RF; SAM |
| BIRC2/cIAP1 | Q13490 | RING | BC016174 | 329 | NM_001166 | Hs.503704 | RF; BIR; CARD |
| BIRC3/cIAP2 | Q13489 | RING | U37546 | 330 | NM_001165 | Hs.127799 | RF; BIR; CARD |
| BIRC4/XIAP | P98170 | RING | U45880 | 331 | NM_001167 | Hs.356076 | RF; BIR |
| BIRC7/Livin | Q96CA5 | RING | BC014475 | 79444 | NM_139317 | Hs.256126 | RF; BIR |
| BIRC8/ILP2 | Q96P09 | RING | AF164682 | 112401 | NM_033341 | Hs.348263 | RF; BIR |
| BRAP | Q7Z569 | RING | AF035620 | 8315 | NM_006768 | Hs.530940 | RF; ZFu |
| BRCA1 | P38398 | RING | U14680 | 672 | NM_007294; NM_007299; NM_007300; NM_007302; NM_007306; NM_007296; NM_007301; NM_007305; NM_007297; NM_007303; NM_007295; NM_007298 | Hs.194143 | RF; BRCT |
| C13orf7 | Q5W0B1 | RING | BC028586 | 79596 | NM_024546 | Hs.93956 | RF |
| C16orf28/FLJ12623 | Q9H9P5 | RING | AK022685 | 65259 | NM_023076 | Hs.161279 | RF |
| C17orf29 | Q63HN8 | RING | BX647946 | 57674 | NM_020914 | Hs.195642 | RF |
| C18orf23/FLJ45559 | Q6ZSG1 | RING | AK127467 | 147341 | NM_152470 | Hs.501114 | RF |
| CBL | P22681 | RING | X57110 | 867 | NM_005188 | Hs.504096 | RF; UBA |
| CBLB | Q13191 | RING | U26710 | 868 | NM_170662 | Hs.430589 | RF; UBA |
| CBLC | Q9ULV8 | RING | AF117646 | 23624 | NM_012116 | Hs.466907 | RF |
| CBLL1 | Q8TAJ4 | RING | BC027460 | 79872 | NM_024814 | Hs.432792 | RF |
| CGRRF1 | Q99675 | RING | U66469 | 10668 | NM_006568 | Hs.59106 | RF |
| CHFR | Q96EP1 | RING | AF170724 | 55743 | NM_018223 | Hs.507336 | RF; FHA |
| CNOT4 | O95628 | RING | U71267 | 4850 | NM_013316; NM_001008225 | Hs.490224 | RF; RBD |
| DKFZp547C195 | Q6P2E0 | RING | BC064581 | 257160 | NM_207343 | Hs.380110 | RF |
| DKFZp761H1710 | Q9H0X6 | RING | AL136540 | 83459 | NM_031297 | Hs.512767 | RF |
| DTX1 | Q86Y01 | RING | BC048216 | 1840 | NM_004416 | Hs.372152 | RF; WWE |
| DTX2 | Q86UW9 | RING | AK023924 | 113878 | NM_020892 | Hs.187058 | RF; WWE |
| DTX3 | Q8N9I9 | RING | AK092085 | 196403 | NM_178502 | Hs.32374 | RF |
| DTX3L/BBAP | Q8TDB6 | RING | BC060509 | 151636 | NM_138287 | Hs.518201 | RF |

TABLE 14-continued

E3 Ligases, RING type.

| Name | UniProt | Type | Genbank | LL | Refseq | Unigene | Domains |
|---|---|---|---|---|---|---|---|
| DTX4/KIAA0937 | Q9Y2E6 | RING | AB023154 | none | XM_166213 | Hs.523696 | RF; WWE |
| DZIP3 | Q86Y13 | RING | AB014575 | 9666 | NM_014648 | Hs.409210 | RF |
| FLJ10520 | Q5XKR3 | RING | BC002574 | none | none | Hs.77510 | RF |
| FLJ12270/KIAA1923 | Q96PW5 | RING | AB067510 | 79726 | NM_030581 | Hs.280951 | RF; GlUEV; WD |
| FLJ12875 | Q969V5 | RING | BC014010 | 79594 | NM_024544 | Hs.10101 | RF |
| FLJ16581 | Q62W19 | RING | AK122906 | none | XM_498131 | Hs.448264 | RF; SPRY |
| FLJ20225 | Q9NXI6 | RING | AK000232 | 54546 | NM_019062 | Hs.124835 | RF |
| FLJ20315/URCC | Q65ZA4 | RING | AB081837 | 54894 | NM_017763 | Hs.500398 | RF |
| FLJ23749 | Q8TEA0 | RING | AK074329 | 91694 | NM_152271 | Hs.180178 | RF |
| FLJ31951 | Q8IVP7 | RING | BC042684 | 153830 | NM_144726 | Hs.349306 | RF; DER3 |
| FLJ35757 | Q8NA82 | RING | AK093076 | 162333 | NM_152598 | Hs.446268 | RF |
| FLJ36180 | Q8N9V2 | RING | AK093499 | 339976 | NM_178556 | Hs.348618 | RF; BBOX; SPRY |
| FLJ38628 | Q96Gf1 | RING | BC009504 | 91445 | NM_152267 | Hs.517553 | RF |
| FLJ45273 | Q6ZSR4 | RING | AK127206 | 164832 | NM_198461 | Hs.30646 | RF |
| FLJ46380 | Q6ZRF8 | RING | AK128246 | 388591 | NM_207396 | Hs.512336 | RF |
| HOZFP | Q86VG1 | RING | BC051193 | 152518 | NM_152995 | Hs.351839 | RF |
| KIAA0804 | O94896 | RING | AB018347 | 23355 | NM_015303; NM_001009921 | Hs.269263 | RF |
| KIAA1333/FLJ20333 | Q9NXC0 | RING | AK000340 | 55632 | NM_017769 | Hs.509008 | RF; HECT |
| KIAA1404 | Q9P2E3 | RING | AK002139 | 57169 | NM_021035 | Hs.371794 | RF; SEN1 |
| KIAA1542 | Q9P1Y6 | RING | AB040975 | 57661 | NM_020901 | Hs.325838 | RF |
| KIAA1972 | Q96DX4 | RING | BC013173 | 89970 | NM_133368 | Hs.460885 | RF; SPRY |
| KIAA1991 | Q8NCN4 | RING | AB082522 | none | XM_495886 | Hs.369437 | RF |
| LNX | Q8TBB1 | RING | BC022983 | 84708 | NM_032622 | Hs.407755 | RF; PDZ |
| LNX2 | Q8N448 | RING | BC036755 | 222484 | NM_153371 | Hs.132359 | RF; PDZ |
| LOC149603 | Q6PJR0 | RING | BC012758 | none | XM_047499 | Hs.356377 | RF |
| LOC285498 | Q8IY99 | RING | BC036250 | 285498 | NM_194439 | Hs.248290 | RF |
| LOC493829 | Q8N4X6 | RING | BC033211 | 493829 | NM_001008274 | Hs.535455 | RF; BBOX |
| LOC51136/FLJ25783 | Q8N7D0 | RING | AK098649 | 51136 | NM_016125 | Hs.531701 | RF |
| LOC51255 | Q9P0P0 | RING | AF151072 | 51255 | NM_016494 | Hs.11156 | RF |
| LRSAM1/TAL | Q6UWE0 | RING | AY358830 | 90678 | NM_138361; NM_001005373; NM_001005374 | Hs.495188 | RF; LRR; SAM |
| M96/MTF2 | Q9Y483 | RING | AJ010014 | 22823 | NM_007358 | Hs.31016 | RF |
| MAP3K1 | Q13233 | RING | AF042838 | none | XM_042066 | Hs.508461 | RF; kinase |
| MARCH1 | Q8TCQ1 | RING | AL713759 | 55016 | NM_017923 | Hs.136900 | RF |
| MARCH2/MARCH-II | Q9P0N8 | RING | AF151074 | 51257 | NM_016496; NM_001005416; NM_001005415 | Hs.445113 | RF |
| MARCH3/MARCH-III | Q86UD3 | RING | BC047569 | 115123 | NM_178450 | Hs.132441 | RF |
| MARCH5/RNF153 | Q9NX47 | RING | AK000452 | 54708 | NM_017824 | Hs.549165 | RF |
| MARCH6/KIAA0597 | O60337 | RING | AB011169 | 10299 | NM_005885 | Hs.432862 | RF |
| MARCH7/AXOT | Q9H992 | RING | BC065014 | 64844 | NM_022826 | Hs.529272 | RF |
| MARCH8/MIR | Q8TC72 | RING | BC025394 | 220972 | NM_001002265; NM_145021; NM_001002266 | Hs.494489 | RF |

TABLE 14-continued

E3 Ligases, RING type.

RING

| Name | UniProt | Type | Genbank | LL | Refseq | Unigene | Domains |
|---|---|---|---|---|---|---|---|
| MARCH9/MARCH-IX | Q86VN5 | RING | BC050397 | 92979 | NM_138396 | Hs.65377 | RF; RGG |
| MDM2 | Q00987 | RING | M92424 | 4193 | NM_006878; NM_006881; NM_006880; NM_002392; NM_006882; NM_006879 | Hs.369849 | RF; MBL; NZF; ZFrn |
| MDM4 | O15151 | RING | AF007111 | 4194 | NM_002393 | Hs.497492 | RF; MBL; NZF; ZFrn |
| MGC4734 | Q96D59 | RING | BC013036 | 138065 | NM_145051 | Hs.211374 | RF |
| MGRN1 | Q86W76 | RING | BC050389 | 23295 | NM_015246 | Hs.526494 | RF |
| MIB1/MIB | Q86YT6 | RING | AY149908 | 57534 | NM_020774 | Hs.140903 | RF; Ank; MIBOREP; MIB_HERC2; ZZ |
| MID1 | O15344 | RING | Y13667 | 4281 | NM_000381; NM_033290; NM_033291 | Hs.27695 | RF; POSTRFBBOX; SPRY |
| MID2 | Q9UJV3 | RING | Y18880 | 11043 | NM_052817; NM_012216 | Hs.12256 | RF; POSTRFBBOX; SPRY |
| MKRN1 | Q9UHC7 | RING | BC025955 | 23608 | NM_013446 | Hs.490347 | RF; ZF_MAKORIN |
| MKRN2 | Q9H000 | RING | BC015715 | 23609 | NM_014160 | Hs.279474 | RF; ZF_MAKORIN |
| MKRN3 | Q13064 | RING | U19107 | 7681 | NM_005664 | Hs.72964 | RF; ZF_MAKORIN |
| MNAB/MASNAB | Q9HBD2 | RING | AF255303 | 54542 | NM_018835 | Hs.533499 | RF; ZF_CCCH |
| MNAT1 | P51948 | RING | X87843 | 4331 | NM_002431 | Hs.509523 | RF |
| MYCBP2 | Q6PIB6 | RING | BC037971 | 23077 | NM_015057 | Hs.151411 | RF |
| MYLIP | Q8WY64 | RING | AF006003 | 29116 | NM_013262 | Hs.484738 | RF; BAND_41 |
| NEURL | O76050 | RING | U87864 | 9148 | NM_004210 | Hs.549085 | RF; NEURALIZED |
| NFX1 | Q12986 | RING | U15306 | 4799 | NM_002504; NM_147133; NM_147134 | Hs.413074 | RF; DNABIND_JAG |
| NHLRC1/Malin | Q6VVB1 | RING | BK001510 | 378884 | NM_198586 | Hs.348351 | RF |
| NSMCE1/NSE1 | Q8WV22 | RING | BC018938 | 197370 | NM_145080 | Hs.284295 | RF |
| PCGF1/NSPC1 | Q9BSM1 | RING | BC004952 | 84759 | NM_032673 | Hs.316750 | RF |
| PCGF2/RNF110 | P35227 | RING | D13969 | 7703 | NM_007144 | Hs.371617 | RF |
| PCGF4/BMI1 | P35226 | RING | L13689 | 648 | NM_005180 | Hs.380403 | RF |
| PCGF5 | Q86SE9 | RING | BC051845 | 84333 | NM_032373 | Hs.500512 | RF |
| PCGF6/hMBLR | Q9BYE7 | RING | AB047006 | 84108 | NM_032154 | Hs.335808 | RF |
| PDZRN3/KIAA1095 | Q9UPQ7 | RING | AB029018 | 23024 | NM_015009 | Hs.434900 | RF; PDZ; ZFt |
| PEX10 | O60683 | RING | AF060502 | 5192 | NM_153818; NM_002617 | Hs.546273 | RF |
| PEX12 | O00623 | RING | U91521 | 5193 | NM_000286 | Hs.270532 | RF |
| PHF7 | Q9NSX7 | RING | BC022002 | 51533 | NM_173341; NM_016483 | Hs.372719 | RF |
| PJA1 | Q8NG27 | RING | AF262024 | 64219 | NM_022368; NM_145119 | Hs.522679 | RF |
| PJA2 | Q8N1G5 | RING | BC030826 | 9867 | NM_014819 | Hs.483036 | RF |
| PML | P29590 | RING | AF230401 | 5371 | NM_033246; NM_033239; NM_033240; NM_033242; | Hs.526464 | RF; BBOX |

TABLE 14-continued

E3 Ligases, RING type.

RING

| Name | UniProt | Type | Genbank | LL | Refseq | Unigene | Domains |
|---|---|---|---|---|---|---|---|
| PXMP3 | P28328 | RING | M86852 | 5828 | NM_033247; NM_033238; NM_033244; NM_002675; NM_033250; NM_033249; NM_033245 | Hs.437966 | RF |
| RAD18 | Q9NS91 | RING | AB035274 | 56852 | NM_000318 | Hs.375684 | RF; SAF; ZF_RAD18 |
| RAG1 | P15918 | RING | M29474 | 5896 | NM_020165 | Hs.73958 | RF |
| RAPSN | Q13702 | RING | Z33905 | 5913 | NM_000448 NM_005055; NM_032645 | Hs.81218 | RF; TPR |
| RBBP6 | Q7Z6E9 | RING | AB112074 | 5930 | NM_032626; NM_018703; NM_006910 | Hs.185553 | RF; ZFc |
| RBX1 | P62877 | RING | AF142059 | 9978 | NM_014248 | Hs.474949 | RF |
| RCHY1 | Q96PM5 | RING | AF247041 | 25898 | NM_015436; NM_001009922; NM_001008925 | Hs.48297 | RF; ZF_CHYCT; ZF_HOT13 |
| RFFL | Q8TBY7 | RING | BC028424 | 117584 | NM_057178 | Hs.13680 | RF; FYVE |
| RFP | P14373 | RING | J03407 | 5987 | NM_006510; NM_030950 | Hs.440382 | RF; BBOX; SPRY |
| RFP2 | O60858 | RING | AJ224819 | 10206 | NM_213590; NM_052811; NM_001007278; NM_005798 | Hs.436922 | RF; BBOX |
| RFPL1 | O75677 | RING | AJ010228 | 5988 | NM_021026 | Hs.167750 | RF; SPRY |
| RFPL2 | O75678 | RING | BC051910 | 10739 | NM_006605 | Hs.157427 | RF; SPRY |
| RFPL3 | O75679 | RING | AJ010232 | 10738 | NM_006604 | Hs.167751 | RF; SPRY |
| RFWD2/COP1 | Q8NHY2 | RING | AF508940 | 64326 | NM_001001740; NM_022457 | Hs.523744 | RF; WD |
| RING1 | Q06587 | RING | Z14000 | 6015 | NM_002931 | Hs.202430 | RF |
| RKHD1 | Q86XN8 | RING | AB107353 | 399664 | NM_203304 | Hs.436495 | RF; KH |
| RKHD2 | Q5U5Q3 | RING | BC041122 | 51320 | NM_016626 | Hs.465144 | RF |
| RKHD3/KIAA2009 | Q8IVG2 | RING | AB095929 | 84206 | NM_032246 | Hs.104744 | RF; KH |
| RNF10/RIE2 | Q9ULW4 | RING | AB027196 | 9921 | NM_014868 | Hs.442798 | RF |
| RNF103 | O00237 | RING | D76444 | 7844 | NM_005667 | Hs.469199 | RF |
| RNF11 | Q9Y3C5 | RING | AB024703 | 26994 | NM_014372 | Hs.309641 | RF |
| RNF111 | Q6P9A4 | RING | BC060862 | 54778 | NM_017610 | Hs.404423 | RF |
| RNF12 | Q9NVW2 | RING | AJ271670 | 51132 | NM_016120; NM_183353 | Hs.122121 | RF |
| RNF121 | Q96DB4 | RING | BC009672 | 55298 | NM_194453; NM_194452; NM_018320 | Hs.368554 | RF |

TABLE 14-continued

E3 Ligases, RING type.
RING

| Name | UniProt | Type | Genbank | LL | Refseq | Unigene | Domains |
|---|---|---|---|---|---|---|---|
| RNF122/FLJ12526 | Q9H9V4 | RING | AK022588 | 79845 | NM_024787 | Hs.151237 | RF |
| RNF123/KPC1 | Q5XPI4 | RING | AY744152 | 63891 | NM_022064 | Hs.517970 | RF; SPRY |
| RNF125 | Q96EQ8 | RING | BC012021 | 54941 | NM_017831 | Hs.272800 | RF; ZF_ZNF313 |
| RNF126 | Q9BV68 | RING | BC001442 | 55658 | NM_017876; NM_194460 | Hs.69554 | RF; ZF_CIP8 |
| RNF127/FLJ34458 | Q8NB00 | RING | AK091777 | 79836 | NM_024778 | Hs.144266 | RF; TPR |
| RNF128/GRAIL | Q96RF3 | RING | AF394689 | 79589 | NM_194463; NM_024539 | Hs.496542 | RF; PA |
| RNF13 | O43567 | RING | AF037204 | 11342 | NM_183381; NM_183384; NM_007282; NM_183383; NM_183382 | Hs.12333 | RF; PA |
| RNF130 | Q86XS8 | RING | AY083998 | 55819 | NM_018434 | Hs.484363 | RF; PA |
| RNF133 | Q8WVZ7 | RING | BC022038 | 168433 | NM_139175 | Hs.549267 | RF; PA |
| RNF135/MGC13061 | Q8IUD6 | RING | AY598332 | 84282 | NM_032322; NM_197939 | Hs.29874 | RF; SPRY |
| RNF138 | Q8WVD3 | RING | BC018107 | 51444 | NM_198128; NM_016271 | Hs.302408 | RF; ZF_ZNF313 |
| RNF139/TRC8 | O75485 | RING | AF064801 | 11236 | NM_007218 | Hs.492751 | RF; DER3 |
| RNF141 | Q8WVD5 | RING | BC018104 | 50862 | NM_016422 | Hs.44685 | RF |
| RNF146/Dactylidin | Q9NTX7 | RING | AK027558 | 81847 | NM_030963 | Hs.267120 | RF; WWE |
| RNF148 | Q8N308 | RING | BC029264 | 378925 | NM_198085 | Hs.529656 | RF; PA |
| RNF149 | Q8NC42 | RING | AK074985 | 284996 | NM_173647 | Hs.171802 | RF; PA |
| RNF150/KIAA1214 | Q9ULK6 | RING | AB033040 | 57484 | NM_020724 | Hs.480825 | RF |
| RNF151 | Q8NHS5 | RING | BC029501 | none | XM_370927 | Hs.99354 | RF; ZFt |
| RNF152 | Q8N8N0 | RING | AK096495 | 220441 | NM_173557 | Hs.465316 | RF |
| RNF157/KIAA1917 | Q96PX1 | RING | AB067504 | 114804 | NM_052916 | Hs.269891 | RF; ZF_ZNF313 |
| RNF166 | Q96A37 | RING | BC017226 | 115992 | NM_178841 | Hs.513804 | RF; PA |
| RNF167 | Q9H6Y7 | RING | AK025329 | 26001 | NM_015528 | Hs.7158 | RF |
| RNF168/FLJ35794 | Q8IYW5 | RING | BC033791 | 165918 | NM_152617 | Hs.518396 | RF |
| RNF170 | Q86YC0 | RING | BC044566 | 81790 | NM_030954 | Hs.491626 | RF |
| RNF175/LOC285533 | Q8N4F7 | RING | BC034385 | 285533 | NM_173662 | Hs.388364 | RF |
| RNF180 | Q86T96 | RING | AL832580 | 285671 | NM_178532 | Hs.98890 | RF |
| RNF182/MGC33993 | Q8N6D2 | RING | BC030666 | 221687 | NM_152737 | Hs.111164 | RF |
| RNF2/DING | Q99496 | RING | Y10571 | 6045 | NM_007212 | Hs.124186 | RF |
| RNF20 | Q5VTR2 | RING | BC063115 | 56254 | NM_019592 | Hs.168095 | RF |
| RNF24 | Q9Y225 | RING | AL096778 | 11237 | NM_007219 | Hs.114180 | RF |
| RNF25 | Q96BH1 | RING | BC015612 | 64320 | NM_022453 | Hs.471403 | RF; GIUEV |
| RNF26 | Q9BY78 | RING | AB055622 | 79102 | NM_032015 | Hs.524084 | RF |
| RNF32 | Q6FIB3 | RING | CR533513 | 140545 | NM_030936 | Hs.490715 | RF; IQ |
| RNF34 | Q969K3 | RING | AF306709 | 80196 | NM_194271; NM_025126 | Hs.292804 | RF; FYVE |
| RNF36 | Q86WT6 | RING | BC047945 | 140691 | NM_080745; NM_182985 | Hs.169810 | RF; POSTBBOX; SPRY |

TABLE 14-continued

E3 Ligases, RING type. RING

| Name | UniProt | Genbank | Type | LL | Refseq | Unigene | Domains |
|---|---|---|---|---|---|---|---|
| RNF38 | Q9H0F5 | AF394047 | RING | 152006 | NM_194330; NM_022781; NM_194328; NM_194331; NM_194329; NM_194332 | Hs.333503 | RF |
| RNF39/HCGV | Q96QB5 | AF238315 | RING | 80352 | NM_025236; NM_170769; NM_170770 | Hs.121178 | RF; SPRY |
| RNF3A | O15262 | AJ001019 | RING | 10336 | NM_006315 | Hs.144309 | RF |
| RNF4 | P78317 | AB000468 | RING | 6047 | NM_002938 | Hs.66394 | RF |
| RNF40/KIAA0661 | O75150 | AB014561 | RING | 9810 | NM_194352; NM_014771 | Hs.65238 | RF |
| RNF41 | O75598 | AF077599 | RING | 10193 | NM_194358; NM_194359; NM_005785 | Hs.524502 | RF |
| RNF44 | Q7L0R7 | BC039833 | RING | 22838 | NM_014901 | Hs.434888 | RF |
| RNF5/HsRma1 | Q99942 | AB056869 | RING | 6048 | NM_006913 | Hs.534342 | RF |
| RNF6 | Q9Y252 | AJ010347 | RING | 6049 | NM_183044; NM_005977; NM_183043; NM_183045 | Hs.136885 | RF |
| RNF7/ROC2 | Q9UBF6 | AF164679 | RING | 9616 | NM_183237; NM_183063; NM_014245 | Hs.134623 | RF |
| RNF8 | O76064 | AB012770 | RING | 9025 | NM_003958; NM_183078 | Hs.485278 | RF; FHA |
| RP11-307C12.10 | Q5T197 | AK057347 | RING | 149095 | NM_152494 | Hs.351431 | RF |
| RP4-678E16.1 | Q5VTB9 | BC034221 | RING | 55182 | NM_018150 | Hs.456557 | RF |
| RP5-1198E17.5 | Q5TC82 | AB095945 | RING | none | XM_086409 | Hs.495097 | RF; ZF_CCCH |
| SH3MD2 | Q7Z6J0 | BC053671 | RING | 57630 | NM_020870 | Hs.301804 | RF; SH3 |
| SH3RF2/FLJ23654 | Q8TEC5 | AK074234 | RING | 153769 | NM_152550 | Hs.443728 | RF; SH3 |
| SIAH1 | Q8IUQ4 | U63295 | RING | 6477 | NM_001006610; NM_003031; NM_001006611 | Hs.295923 | RF |
| SIAH2 | O43255 | Y15268 | RING | 6478 | NM_005067 | Hs.477959 | RF |
| SMARCA3/HIP116 | Q14527 | L34673 | RING | 6596 | NM_139048; NM_003071 | Hs.3068 | RF |
| SYVN1/HRD1 | Q8NGE8 | BC030530 | RING | 84447 | NM_172230; NM_032431 | Hs.321535 | RF; DER3 |
| TOPORS | Q9UNR9 | AF098300 | RING | 10210 | NM_005802 | Hs.535961 | RF; ICP0 |
| TRAF2 | Q12933 | BC032410 | RING | 7186 | NM_021138 | Hs.522506 | RF; ZFt; TRAF |
| TRAF3 | Q13114 | U21092 | RING | 7187 | NM_145725; NM_003300; NM_145726 | Hs.510528 | RF; ZFt; TRAF |
| TRAF4 | Q9BUZ4 | BC001769 | RING | 9618 | NM_004295; NM_145751 | Hs.8375 | RF; ZFt; TRAF |

TABLE 14-continued

E3 Ligases, RING type.
RING

| Name | UniProt | Genbank | Type | LL | Refseq | Unigene | Domains |
|---|---|---|---|---|---|---|---|
| TRAF5 | O00463 | AB000509 | RING | 7188 | NM_145759; NM_004619 | Hs.523930 | RF; ZFt; TRAF |
| TRAF6 | Q9Y4K3 | U78798 | RING | 7189 | NM_145803; NM_004620 | Hs.444172 | RF; ZFt; TRAF |
| TRAF7 | Q6Q0C0 | AY569455 | RING | 84231 | NM_032271; NM_206835 | Hs.334479 | RF; ZFt; WD |
| TRIM10 | Q9UDY6 | AF220122 | RING | 10107 | NM_052828; NM_006778 | Hs.274295 | RF; BBOX; POSTBBOX; SPRY |
| TRIM11 | Q96F44 | AF327056 | RING | 81559 | NM_145214 | Hs.13543 | RF; BBOX; POSTBBOX; SPRY |
| TRIM15 | Q9C019 | AF220132 | RING | 89870 | NM_033229; NM_052812 | Hs.309602 | RF; BBOX; POSTBBOX; SPRY |
| TRIM17 | Q9Y577 | AF156271 | RING | 51127 | NM_016102 | Hs.121748 | RF; BBOX; POSTBBOX; SPRY |
| TRIM2 | Q9C040 | AF220018 | RING | 23321 | NM_015271 | Hs.435711 | RF; BBOX; POSTBBOX |
| TRIM21 | P19474 | M34551 | RING | 6737 | NM_003141 | Hs.532357 | RF; BBOX; POSTBBOX; SPRY |
| TRIM22 | Q8IYM9 | BC035582 | RING | 10346 | NM_006074 | Hs.501778 | RF; BBOX; POSTBBOX; SPRY |
| TRIM23 | P36406 | L04510 | RING | 373 | NM_033227; NM_001656; NM_033228 | Hs.792 | RF; BBOX; GTPase |
| TRIM25 | Q14258 | D21205 | RING | 7706 | NM_005082 | Hs.534366 | RF; SPRY |
| TRIM26 | Q12899 | U09825 | RING | 7726 | NM_003449 | Hs.485041 | RF; BBOX; POSTBBOX; SPRY |
| TRIM3 | O75382 | AF045239 | RING | 10612 | NM_006458; NM_033278 | Hs.159408 | RF; BBOX; POSTBBOX |
| TRIM31 | Q9BZY9 | AF230386 | RING | 11074 | NM_007028; NM_052816 | Hs.493275 | RF; BBOX; POSTBBOX |
| TRIM32 | Q13049 | AL133284 | RING | 22954 | NM_012210 | Hs.209217 | RF; BBOX |
| TRIM34 | Q9BY14 | AB039902 | RING | 53840 | NM_001003827; NM_021616; NM_130390; NM_130389 | Hs.125300 | RF; BBOX; POSTBBOX; SPRY |
| TRIM35 | Q9UPQ4 | AF492463 | RING | 23087 | NM_015066; NM_171982 | Hs.104223 | RF; BBOX; SPRY |
| TRIM36 | Q9NQ86 | AJ272269 | RING | 55521 | NM_018700 | Hs.519514 | RF; BBOX; POSTBBOX; SPRY |
| TRIM37 | O94972 | AB020705 | RING | 4591 | NM_001005207; NM_015294 | Hs.412767 | RF; BBOX; TRAF |
| TRIM38 | O00635 | U90547 | RING | 10475 | NM_006355 | Hs.202510 | RF; BBOX; POSTBBOX; SPRY |
| TRIM39/RNF23 | Q9HCM9 | AB046381 | RING | 56658 | NM_172016; NM_021253 | Hs.413493 | RF; BBOX; POSTBBOX; SPRY |

TABLE 14-continued

E3 Ligases, RING type.

| Name | UniProt | Type | Genbank | LL | Refseq | Unigene | Domains |
|---|---|---|---|---|---|---|---|
| TRIM4 | Q9C037 | RING | AF220023 | 89122 | NM_057096; NM_057095; NM_022820; NM_033091; NM_033017 | Hs.50749 | RF; BBOX; POSTBBOX; SPRY |
| TRIM40/RNF35 | Q6P9F5 | RING | BC060785 | 135644 | NM_138700 | Hs.509439 | RF; BBOX |
| TRIM41 | Q8WV44 | RING | AB100366 | 90933 | NM_033549; NM_201627 | Hs.441488 | RF; BBOX; POSTBBOX; SPRY |
| TRIM42 | Q8IWZ5 | RING | AF521868 | 287015 | NM_152616 | Hs.343487 | RF; BBOX; POSTBBOX |
| TRIM43 | Q96BQ3 | RING | BC015353 | 129868 | NM_138800 | Hs.232026 | RF; BBOX; SPRY |
| TRIM45 | Q9H8W5 | RING | AY669488 | 80263 | NM_025188 | Hs.301526 | RF; BBOX; POSTBBOX |
| TRIM46 | Q7Z4K8 | RING | AY251386 | 80128 | NM_025058 | Hs.287735 | RF; BBOX; POSTBBOX; SPRY |
| TRIM47 | Q96LD4 | RING | AY026763 | 91107 | NM_033452 | Hs.293660 | RF; BBOX; SPRY |
| TRIM48 | Q8IWZ4 | RING | AF521869 | 79097 | NM_024114 | Hs.195715 | RF; BBOX; SPRY |
| TRIM49/RNF18 | Q9NS80 | RING | AB037682 | 57093 | NM_020358 | Hs.534218 | RF; BBOX; SPRY |
| TRIM5 | Q9C035 | RING | AF220025 | 85363 | NM_033034; NM_033093; NM_033092 | Hs.370515 | RF; BBOX; POSTBBOX; SPRY |
| TRIM50A | Q86XT4 | RING | AY081948 | 135892 | NM_178125 | Hs.404810 | RF; BBOX; SPRY |
| TRIM50B | Q86UV7 | RING | AF498998 | none | XM_353628 | Hs.511015 | RF; BBOX |
| TRIM50C | Q86UV6 | RING | AF498999 | 378108 | NM_198853 | Hs.534009 | RF; BBOX; ZF_RAD18 |
| TRIM52 | Q96A61 | RING | AK054802 | 84851 | NM_032765 | Hs.458412 | RF; BBOX |
| TRIM54/RNF30 | Q9BYV2 | RING | AJ291714 | 57159 | NM_187841; NM_032546 | Hs.516036 | RF; BBOX; POSTBBOX |
| TRIM55/RNF29 | Q9BYV6 | RING | BC007750 | 84675 | NM_184087; NM_184085; NM_184086; NM_033058 | Hs.85524 | RF; BBOX; POSTBBOX |
| TRIM56 | Q9BRZ2 | RING | BC005847 | 81844 | NM_030961 | Hs.521092 | RF; BBOX; POSTBBOX |
| TRIM58/BIA2 | Q8NG06 | RING | AK096188 | 25893 | NM_015431 | Hs.323858 | RF; POSTBBOX; SPRY |
| TRIM59/TSBF1 | Q8IWR1 | RING | AY159379 | 286827 | NM_173084 | Hs.212957 | RF; BBOX |
| TRIM6 | Q9C030 | RING | AF220030 | 117854 | NM_058166; NM_001003818 | Hs.350518 | RF; BBOX; POSTBBOX; SPRY |
| TRIM60/FLJ35882 | Q8NA35 | RING | AK093201 | 166655 | NM_152620 | Hs.368004 | RF; BBOX; POSTBBOX; SPRY |
| TRIM61 | Q5EBN2 | RING | BC089393 | 391712 | NM_001012414 | Hs.529351 | RF; BBOX |
| TRIM62 | Q9BVG3 | RING | BC001222 | 55223 | NM_018207 | Hs.404997 | RF; BBOX; POSTBBOX; SPRY |
| TRIM63/RNF28 | Q969Q1 | RING | AF353673 | 84676 | NM_032588 | Hs.279709 | RF; BBOX; POSTBBOX |
| TRIM65 | Q6PJ69 | RING | BC021259 | 201292 | NM_173547 | Hs.189823 | RF; BBOX; SPRY |
| TRIM67/TNL | Q7Z4K7 | RING | AY253917 | 440730 | NM_001004342 | Hs.131295 | RF; BBOX; POSTBBOX; SPRY |

TABLE 14-continued

E3 Ligases, RING type.

RING

| Name | UniProt | Type | Genbank | LL | Refseq | Unigene | Domains |
|---|---|---|---|---|---|---|---|
| TRIM68 | Q6AZZ1 | RING | BC075058 | 55128 | NM_018073 | Hs.523438 | RF; BBOX; SPRY |
| TRIM7 | Q9C029 | RING | AF396651 | 81786 | NM_203295; NM_203297; NM_203294; NM_203293; NM_033342; NM_203296 | Hs.487412 | RF; BBOX; POSTBBOX; SPRY |
| TRIM8 | Q9BZR9 | RING | AF220034 | 81603 | NM_030912 | Hs.336810 | RF; POSTRF; BBOX |
| TRIM9 | Q9C026 | RING | AF220037 | 114088 | NM_052978; NM_015163 | Hs.368928 | RF; BBOX; POSTBBOX; SPRY |
| TRIP/TRAIP | Q9BWF2 | RING | BC000310 | 10293 | NM_005879 | Hs.517972 | RF |
| TTC3 | P53804 | RING | D83077 | 7267 | NM_001001894; NM_003316 | Hs.368214 | RF; TPR |
| UBOX5/RNF37 | O94941 | RING + Ubox | AB020667 | 22888 | NM_199415; NM_014948 | Hs.129448 | RF |
| UBR1 | Q8IWV7 | RING | AY061886 | 197131 | NM_174916 | Hs.145209 | RF; CLPS; ZF_UBR1 |
| UBR2/UBR1L2 | Q8IWV8 | RING | AY061884 | 23304 | NM_015255 | Hs.529925 | RF; CLPS; ZF_UBR1 |
| UHRF1/FLJ21925 | Q9H6S6 | RING | AK025578 | 29128 | NM_013282 | Hs.108106 | RF |
| UHRF2 | Q659C8 | RING | AL137728 | 115426 | NM_152896; NM_152306 | Hs.493401 | RF |
| VPS11 | Q9H270 | RING | AF308800 | 55823 | NM_021729 | Hs.234282 | RF; Clath |
| VPS18 | Q9P253 | RING | AF308802 | 57617 | NM_020857 | Hs.23876 | RF; Clath |
| VPS41 | P49754 | RING | U87309 | 27072 | NM_014396; NM_080631 | Hs.148721 | RF; Clath |
| ZFPL1 | O95159 | RING | AF030291 | 7542 | NM_006782 | Hs.155165 | RF |
| ZNF179 | Q9ULX5 | RING | AB026054 | 7732 | NM_007148 | Hs.189482 | RF; GTPase |
| ZNF183 | O15541 | RING | X98253 | 7737 | NM_006978 | Hs.458365 | RF; ZF_CCCH |
| ZNF183L1 | Q8IZP6 | RING | BC017585 | 140432 | NM_178861 | Hs.296045 | RF; ZF_CCCH |
| ZNF294 | O94822 | RING | AB018257 | 26046 | NM_015565 | Hs.288773 | RF; GlUEV |
| ZNF313 | Q9Y508 | RING | AF265215 | 55905 | NM_018683 | Hs.144949 | RF; ZF_ZNF313 |
| ZNF364 | Q9Y4L5 | RING | AF419857 | 27246 | NM_014455 | Hs.523550 | RF; ZF_CIP8 |
| ZNF598 | Q86UK7 | RING | BC050477 | 90850 | NM_178167 | Hs.343828 | RF |
| ZNF645 | Q6DJY9 | RING | BC074910 | 158506 | NM_152577 | Hs.132485 | RF; BBOX |
| ZNF650/UBR1L1 | Q6ZT12 | RING | AK126998 | 130507 | NM_172070 | Hs.379548 | RF; UBR1CT |
| ZNRF1 | Q8ND25 | RING | AL834440 | 84937 | NM_032268 | Hs.427284 | RF; ZF_RAD18 |
| ZNRF2 | Q8NHG8 | RING | AF527533 | 223082 | NM_147128 | Hs.487869 | RF; ZF_RAD18 |
| ZNRF3/KIAA1133 | Q9ULT6 | RING | AB051436 | none | XM_290972 | Hs.134473 | RF |
| ZNRF4/LOC148066 | Q8WWF5 | RING | BC017592 | 148066 | NM_181710 | Hs.126496 | RF; PA |
| ZSWIM2 | Q8NEG5 | RING | BC031094 | 151112 | NM_182521 | Hs.375054 | RF; ZZ |
| ZZANK1/Skeletrophin | Q8NI59 | RING | AB074480 | 142678 | NM_080875 | Hs.135805 | RF; Ank; MIBOREP; MIBHERC2; ZZ |
| ENSP00000280266 | ENSP00000280266 | RING | ENST00000280266 | none | none | none | RF; BBOX; SPRY |
| ENSP00000344026 | ENSP00000344026 | RING | ENST00000344287 | none | XM_292796 | Hs.451647 | RF; SPRY |
| ENSP00000348371 | ENSP00000348371 | RING | ENST00000356071 | none | NM_373101 | Hs.356440 | RF; NEURALIZED |
| GENSCAN00000024511 | GENSCAN00000024511H | RING | GENSCAN00000024511 | none | XM_497353 | Hs.131991 | RF; SPRY |
| DKFZp434E1818 | ENSP00000343122 | RING | AL133632 | none | XM_372169 | Hs.512564 | RF |
| MKRN4 | Q13434 | pseudogene | U41315 | | | | RF; ZF_MAKORIN |

TABLE 15

E3 Ligases, PARKIN-Finger type.
PARKIN-Finger

| Name | UniProt | Type | Genbank | LL | Refseq | Unigene | Domains |
|---|---|---|---|---|---|---|---|
| ANKIB1 | Q9P2G1 | PF | AB037807 | none | XM_377955 | Hs.83293 | PF1; PF2; PF3; Ank; ARICT; ARINT; UIM |
| ARIH1/UBCH7BP | Q9Y4X5 | PF | BC051877 | 25820 | NM_005744 | Hs.268787 | PF1; PF2; PF3; ARICT; ARINT |
| ARIH2/TRIAD1 | O95376 | PF | AF099149 | 10425 | NM_006321 | Hs.241558 | PF1; PF2; PF3; ARICT; ARINT |
| IBRDC1 | Q8TC41 | PF | BC026087 | 154214 | NM_152553 | Hs.368639 | PF1; PF2; PF3 |
| IBRDC2 | Q7Z419 | PF | AB076367 | 255488 | NM_182757 | Hs.148741 | PF1; PF2; PF3 |
| IBRDC3 | Q6ZMZ0 | PF | AK131439 | 127544 | NM_153341 | Hs.546478 | PF1; PF2; PF3 |
| PARC | Q8IWT3 | PF | AJ318215 | 23113 | NM_015089 | Hs.485434 | PF1; PF2; PF3; ARICT; ARINT; CULLIN; DOC1; HERC2 |
| PARK2 | O60260 | PF | AB009973 | 5071 | NM_013987; NM_004562; NM_013988 | Hs.132954 | PF1; PF2; PF3; Ubiq |
| RNF14/ARA54 | Q9UBS8 | PF | AB022663 | 9604 | NM_183401; NM_183398; NM_183399; NM_183400; NM_004290 | Hs.508993 | PF1; PF2; PF3; GIUEV |
| RNF144 | P50876 | PF | D79983 | 9781 | NM_014746 | Hs.22146 | PF1; PF2; PF3 |
| RNF19 | Q9NV58 | PF | AB029316 | 25897 | NM_183419; NM_015435 | Hs.292882 | PF1; PF2; PF3 |
| RNF31 | Q96EP0 | PF | BC012077 | 55072 | NM_017999 | Hs.375217 | PF1; PF2; PF3; PUB; UBA; ZFm; NZF |
| UBCE7IP1/TRIAD3 | Q9NWF9 | PF | AF513717 | 54476 | NM_207116; NM_207111; NM_019011 | Hs.487458 | PF1; PF2; PF3 |
| UBCE7IP3/C20ORF18 | Q9BYM8 | PF | BC015219 | 10616 | NM_031229; NM_006462; NM_031227; NM_031228 | Hs.247280 | PF1; PF2; PF3; Ubiq; NZF |
| GENSCAN00000039330H | GENSCAN00000039330H | PF pseudogene | | | | | PF1; PF2; PF3 |

TABLE 16

E3 Ligases, RING-variants type.
RING-variants

| Name | UniProt | Type | Genbank | LL | Refseq | Unigene | Domains |
|---|---|---|---|---|---|---|---|
| C20orf43 | Q9BY42 | RINGvar | AF161518 | 51507 | NM_016407 | Hs.517134 | RFvar |
| FLJ13910 | Q9H871 | RINGvar | AK023972 | 64795 | NM_022780 | Hs.75277 | CTLH; RFvar; LISH |
| FLJ22318 | Q96G75 | RINGvar | AL713670 | 64777 | NM_022762 | Hs.519804 | CTLH; RFvar |
| MAEA | Q9BQ11 | RINGvar | BC006470 | 10296 | NM_005882 | Hs.139896 | CTLH; RFvar; LISH |
| NOSIP | Q96FD2 | RINGvar | BC011249 | 51070 | NM_015953 | Hs.7236 | RFvar |
| PPIL2 | Q13356 | RINGvar | U37219 | 23759 | NM_148175; NM_014337; NM_148176 | Hs.438587 | PPI2; RFvar |
| WDR59 | Q96PW5 | RINGvar | AB067510 | 79726 | NM_030581 | Hs.280951 | RFvar, WD, uev |
| FLJ20323 | Q7L551 | RINGvar | BC005883 | 54468 | NM_019005 | Hs.520215 | RFvar |
| JFP7 | Q96S15 | RINGvar | AL136863 | 84219 | NM_032259 | Hs.459632 | RFvar, WD |
| GTF2H2 | Q13888 | RINGvar | AF078847 | 2966 | NM_001515 | Hs.191356 | RFvar, vWFA |

TABLE 17

E3 Ligases, U-box type.
U-box

| Name | UniProt | Type | Genbank | LL | Refseq | Unigene | Domains |
|---|---|---|---|---|---|---|---|
| CHIP/STUB1 | Q9UNE7 | Ubox | AF129085 | 10273 | NM_005861 | Hs.533771 | Ubox; TPR |
| PRP19/SNEV | Q9UMS4 | Ubox | AJ131186 | 27339 | NM_014502 | Hs.502705 | Ubox; WD |
| UBE4A | Q14139 | Ubox | D50916 | 9354 | NM_004788 | Hs.75275 | Ubox |
| UBE4B/UFD2 | O95155 | Ubox | AF043117 | 10277 | NM_006048 | Hs.386404 | Ubox |

TABLE 17-continued

E3 Ligases, U-box type.
U-box

| Name | UniProt | Type | Genbank | LL | Refseq | Unigene | Domains |
|---|---|---|---|---|---|---|---|
| WDSAM1 | Q8N6N8 | Ubox | BC029520 | 151525 | NM_152528 | Hs.20848 | Ubox; SAM; WD |
| GENSCAN00000045262H | GENSCAN00000045262H | Ubox pseudogene | | | | | Ubox |

TABLE 18

E3 Ligases, A20-finger type.
A20-finger

| Name | UniProt | Type | Genbank | LL | Refseq | Unigene | Domains |
|---|---|---|---|---|---|---|---|
| C15orf16/Cezanne2 | Q8TE49 | A20 | AJ430383 | 161725 | NM_130901 | Hs.355236 | A20; OTU; UBAlike |
| RABGEF1/RABEX5 | Q9UJ41 | A20 | BC015330 | 27342 | NM_014504 | Hs.530053 | A20; VPS9_RIN |
| TEX27 | Q9H8U3 | A20 | AK023284 | 60685 | NM_021943 | Hs.36959 | A20; ZF_UF |
| TNFAIP3/A20 | P21580 | A20 | M59465 | 7128 | NM_006290 | Hs.211600 | A20; OTU |
| ZA20D1/Cezanne1 | Q6GQQ9 | A20 | AJ293573 | 56957 | NM_020205 | Hs.98322 | A20; OTU; UBAlike |
| ZA20D2 | O76080 | A20 | AF062346 | 7763 | NM_006007 | Hs.406096 | A20; ZF_UF |
| ZA20D3/AWP1 | Q9GZY3 | A20 | AF261138 | 54469 | NM_019006 | Hs.306329 | A20; ZF_UF |

TABLE 19

E3 Ligases, PIAS-finger type.
PIAS-finger

| Name | UniProt | Type | Genbank | LL | Refseq | Unigene | Domains |
|---|---|---|---|---|---|---|---|
| FLJ32440 | Q96MF7 | PIAS | AK057002 | 286053 | NM_173685 | Hs.388297 | PIAS |
| PIAS1 | O75925 | PIAS | AF167160 | 8554 | NM_016166 | Hs.162458 | PIAS; SAF |
| PIAS2/PIASx | O75928 | PIAS | AF077954 | 9063 | NM_004671; NM_173206 | Hs.514846 | PIAS; SAF |
| PIAS3 | Q9Y6X2 | PIAS | BC001154 | 10401 | NM_006099 | Hs.435761 | PIAS; SAF |
| PIAS4/PIASy | Q8N2W9 | PIAS | BC029874 | 51588 | NM_015897 | Hs.105779 | PIAS; SAF |
| RAI17 | Q9ULJ6 | PIAS | AY235683 | 57178 | NM_020338 | Hs.193118 | PIAS |
| ZIMP7/DKFZp76112123 | Q8NF64 | PIAS | AK090415 | 83637 | NM_174929; NM_031449 | Hs.77978 | PIAS |
| FLJ13517 | Q9H8K2 | Artefactual splice variant of RNF138 | | | | | |

TABLE 20

E3 Ligases, PHD-finger type.
PHD-finger

| Name | UniProt | Type | Genbank | LL | Refseq | Unigene | Domains |
|---|---|---|---|---|---|---|---|
| AIRE | O43918 | PHD | Z97990 | 326 | NM_000658; NM_000383; NM_000659 | Hs.129829 | PHD; SAND; SPC100 |
| other PHD fingers not assumed to be Ub-ligases | | | | | | | |

TABLE 21

E3 Ligases, Skp1-like type.
Skp1-like

| Name | UniProt | Type | Genbank | LL | Refseq | Unigene | Domains |
|---|---|---|---|---|---|---|---|
| SKP1A | P63208 | Skp1like | U33760 | 6500 | NM_170679; NM_006930 | Hs.171626 | Skp1 |
| TCEB1/Elongin C | Q15369 P78561 | Skp1like Skp1like pseudogene | L34587 L49176 | 6921 | NM_005648 | Hs.546305 | Skp1 Skp1 |

TABLE 21-continued

E3 Ligases, Skp1-like type.
Skp1-like

| Name | UniProt | Type | Genbank | LL | Refseq | Unigene | Domains |
|---|---|---|---|---|---|---|---|
|  | P78389 | Skp1like pseudogene | L49173 |  |  |  | Skp1 |
| RP1-254P11.1-001 | Q9H575 | Skp1like pseudogene | AL136318 |  |  |  | Skp1 |
| Fos39347_1 | O75863 | Skp1like pseudogene |  |  |  |  | Skp1 |

TABLE 22

E3 Ligases, Cullin type.
Cullin

| Name | UniProt | Type | Genbank | LL | Refseq | Unigene | Domains |
|---|---|---|---|---|---|---|---|
| ANAPC2 | Q9UJX6 | Cullin | BC032503 | 29882 | NM_013366 | Hs.533262 | CULLIN |
| CUL1 | Q13616 | Cullin | AF062536 | 8454 | NM_003592 | Hs.146806 | CULLIN |
| CUL2 | Q13617 | Cullin | AF126404 | 8453 | NM_003591 | Hs.82919 | CULLIN |
| CUL3 | Q13618 | Cullin | AF064087 | 8452 | NM_003590 | Hs.372286 | CULLIN |
| CUL4A | Q13619 | Cullin | AF077188 | 8451 | NM_003589; NM_001008895 | Hs.339735 | CULLIN |
| CUL4B | Q13620 | Cullin | AY365125 | 8450 | NM_003588 | Hs.102914 | CULLIN |
| CUL5 | Q93034 | Cullin | AF327710 | 8065 | NM_003478 | Hs.440320 | CULLIN |
| CUL7 | Q14999 | Cullin | D38548 | 9820 | NM_014780 | Hs.520136 | CULLIN; DOC1; HERC2 |
| PARC | Q8IWT3 | Cullin | AJ318215 | 23113 | NM_015089 | Hs.485434 | ARICT; ARINT; CULLIN; DOC1; HERC2; PF1; PF2; PF3 |

TABLE 23

E3 Ligases, F-box type.
F-box

| Name | UniProt | Type | Genbank | LL | Refseq | Unigene | Domains |
|---|---|---|---|---|---|---|---|
| FBXL1/SKP2 | Q13309 | Fbox | AB050979 | 6502 | NM_032637; NM_005983 | Hs.23348 | FBOX; LRR |
| FBXL10 | Q8NHM5 | Fbox | AJ459424 | 84678 | NM_001005366; NM_032590 | Hs.524800 | FBOX; LRR; PHD; JMJC; ZF_DNAMET |
| FBXL11 | Q9Y2K7 | Fbox | AB023221 | 22992 | NM_012308 | Hs.124147 | FBOX; LRR; PHD; JMJC; ZF_DNAMET |
| FBXL12 | Q9NXK8 | Fbox | AK000195 | 54850 | NM_017703 | Hs.12439 | FBOX; LRR |
| FBXL13 | Q8NEE6 | Fbox | AK097537 | 222235 | NM_145032 | Hs.434284 | FBOX; LRR |
| FBXL14 | Q8N1E6 | Fbox | BC028132 | 144699 | NM_152441 | Hs.367956 | FBOX; LRR |
| FBXL15/FBXO37 | Q9H469 | Fbox | CR592302 | none | XM_370575 | Hs.380081 | FBOX; LRR |
| FBXL16 | Q8N461 | Fbox weak | BC036680 | 146330 | NM_153350 | Hs.513244 | FBOX; LRR; |
| FBXL17/FBXO13 | Q9UF56 | Fbox | AK126722 | 64839 | NM_022824 | Hs.112143 | FBOX; LRR |
| FBXL18 | Q96ME1 | Fbox | AK057042 | 80028 | NM_024963 | Hs.487447 | FBOX; LRR |
| FBXL19 | Q6PCT2 | Fbox | AK098777 | 54620 | NM_019085 | Hs.152149 | FBOX; LRR; PHD; ZF_DNAMET |
| FBXL2 | Q9UKC9 | Fbox | AF176518 | 25827 | NM_012157 | Hs.475872 | FBOX; LRR |
| FBXL20 | Q96IG2 | Fbox | BC007557 | 84961 | NM_032875 | Hs.462946 | FBOX; LRR |
| FBXL21 | Q9UKT6 | Fbox | AF129533 | 26223 | NM_012159 | Hs.167877 | FBOX; LRR |
| FBXL22 | Q6P050 | Fbox | BC065833 | 283807 | NM_203373 | Hs.549302 | FBOX; LRR |
| FBXL3 | Q9UKT7 | Fbox | AF129532 | 26224 | NM_012158 | Hs.508284 | FBOX; LRR |
| FBXL4 | Q9UKA2 | Fbox | AF174590 | 26235 | NM_012160 | Hs.536850 | FBOX; LRR |
| FBXL5 | Q9UKA1 | Fbox | AF176700 | 26234 | NM_012161; NM_033535 | Hs.479208 | FBOX; LRR |
| FBXL6 | Q8N531 | Fbox | #NAME? | 26233 | NM_012162; NM_024555 | Hs.12271 | FBOX; LRR |
| FBXL7 | Q9UJT9 | Fbox | AF199356 | 23194 | NM_012304 | Hs.433057 | FBOX; LRR |
| FBXL8 | Q96CD0 | Fbox | AK002140 | 55336 | NM_018378 | Hs.75486 | FBOX; LRR |
| FBXL9/LRRC29 | Q8WV35 | Fbox | BC018785 | 26231 | NM_012163; NM_001004055 | Hs.461000 | FBOX; LRR |
| FBXO1/CCNF | P41002 | Fbox | BC012349 | 899 | NM_001761 | Hs.1973 | FBOX; CYCLIN; SEL1 |
| FBXO10 | Q9UK96 | Fbox | AF176705 | none | XM_291314 | none | FBOX |
| FBXO11 | Q86XK2 | Fbox | BC012728 | 80204 | NM_012167; NM_025133; NM_018693 | Hs.549201 | FBOX; ZF_UBR1 |

TABLE 23-continued

E3 Ligases, F-box type.
F-box

| Name | UniProt | Type | Genbank | LL | Refseq | Unigene | Domains |
|---|---|---|---|---|---|---|---|
| FBXO15 | Q8NCQ5 | Fbox | BC029579 | 201456 | NM_152676 | Hs.465411 | FBOX |
| FBXO16 | Q8IX29 | Fbox | AF453435 | 157574 | NM_172366 | Hs.532253 | FBOX |
| FBXO17/FBXO26 | Q96EF6 | Fbox | AF386743 | 115290 | NM_148169; NM_024907 | Hs.531770 | FBOX |
| FBXO18 | Q8NFZ0 | Fbox | AF380349 | 84893 | NM_178150; NM_032807 | Hs.498543 | FBOX |
| FBXO2 | Q9UK22 | Fbox | BC025233 | 26232 | NM_012168 | Hs.132753 | FBOX |
| FBXO21 | O94952 | Fbox | AF174601 | 23014 | NM_015002; NM_033624 | Hs.159699 | FBOX |
| FBXO22 | Q8NEZ5 | Fbox | AY005144 | 26263 | NM_147188; NM_012170 | Hs.458959 | FBOX |
| FBXO24 | O75426 | Fbox | AL136811 | 26261 | NM_033506; NM_012172 | Hs.283764 | FBOX; RCC |
| FBXO25 | Q8TCJ0 | Fbox | CR596773 | 26260 | NM_183420; NM_183421; NM_012173 | Hs.438454 | FBOX |
| FBXO27 | Q8NI29 | Fbox | BC014527 | 126433 | NM_178820 | Hs.187461 | FBOX |
| FBXO28 | Q9NVF7 | Fbox | AK001628 | 23219 | NM_015176 | Hs.64691 | FBOX |
| FBXO3 | Q9UK99 | Fbox | AK001943 | 26273 | NM_033406; NM_012175 | Hs.406787 | FBOX; |
| FBXO30 | Q8TB52 | Fbox | BC024326 | 84085 | NM_032145 | Hs.421095 | FBOX; ZFt |
| FBXO31/FBXO14 | Q5XUX0 | Fbox | AY736035 | 79791 | NM_024735 | Hs.549198 | FBOX |
| FBXO32 | Q969P5 | Fbox | AY059629 | 114907 | NM_148177; NM_058229 | Hs.403933 | FBOX |
| FBXO33 | Q7Z6M2 | Fbox | BC053537 | 254170 | NM_203301 | Hs.324342 | FBOX |
| FBXO34 | Q9NWN3 | Fbox | BX248268 | 55030 | NM_017943 | Hs.525348 | FBOX |
| FBXO36 | Q8NEA4 | Fbox | BC033935 | 130888 | NM_174899 | Hs.140666 | FBOX |
| FBXO38 | Q6PIJ6 | Fbox | BC005849 | 81545 | NM_205836; NM_030793 | Hs.483772 | FBOX |
| FBXO39 | Q8N4B4 | Fbox | BC034782 | 162517 | NM_153230 | Hs.368364 | FBOX |
| FBXO4 | Q9UKT5 | Fbox | BC048098 | 26272 | NM_012176; NM_033484 | Hs.165575 | FBOX |
| FBXO40 | Q9UH90 | Fbox | AF204674 | 51725 | NM_016298 | Hs.272564 | FBOX; ZFt |
| FBXO41 | Q8TF61 | Fbox | AB075820 | none | XM_377742 | Hs.23158 | FBOX |
| FBXO42 | Q6P3S6 | Fbox | BC063864 | none | XM_048774 | Hs.522384 | FBOX; KELCH |
| FBXO43 | ENSP00000322600 | Fbox | BC028709 | none | XM_209918 | Hs.339577 | FBOX |
| FBXO44 | Q9H4M3 | Fbox | AK055344 | 93611 | NM_183413; NM_183412; NM_033182 | Hs.519716 | FBOX |
| FBXO45 | ENSP00000310332 | Fbox | AK025697 | none | XM_117294 | Hs.518526 | FBOX; SPRY |
| FBXO46 | Q6PJ61 | Fbox | BC021978 | none | XM_371179 | Hs.128702 | FBOX |
| FBXO5 | Q9UKT4 | Fbox | AF129535 | 26271 | NM_012177 | Hs.520506 | FBOX |
| FBXO6 | Q9NRD1 | Fbox | AF233223 | 26270 | NM_018438 | Hs.464419 | FBOX |
| FBXO7 | Q9Y3I1 | Fbox | AF233225 | 25793 | NM_012179 | Hs.5912 | FBOX; Ubiq |
| FBXO8 | Q9NRD0 | Fbox | AF233224 | 26269 | NM_012180 | Hs.76917 | FBOX; Sec7 |
| FBXO9 | Q9UK97 | Fbox | AF176704 | 26268 | NM_033481; NM_033480; NM_012347 | Hs.216653 | FBOX |
| FBXW1/BTRC | Q9Y297 | Fbox | AF101784 | 8945 | NM_033637; NM_003939 | Hs.500812 | FBOX; WD |
| FBXW10 | Q5XX13 | Fbox | AY729024 | 10517 | NM_031456 | Hs.310275 | FBOX; WD |
| FBXW11 | Q9UKB1 | Fbox | AF176022 | 23291 | NM_033645; NM_033644; NM_012300 | Hs.484138 | FBOX; WD |
| FBXW12/FBXO35 | Q6X9E4 | Fbox | AY247969 | 285231 | NM_207102 | Hs.288793 | FBOX |
| FBXW2 | Q9UKT8 | Fbox | BC018738 | 26190 | NM_012164 | Hs.494985 | FBOX; WD |
| FBXW3 | Q9UKB7 | Fbox | AF174606 | none | none | none | FBOX; WD |
| FBXW4/SHFM3 | P57775 | Fbox | AF281859 | 6468 | NM_022039 | Hs.500822 | FBOX; WD |
| FBXW5 | Q969U6 | Fbox | BC014297 | 54461 | NM_018998; NM_178226; NM_178225 | Hs.522507 | FBOX; WD |
| FBXW7/FBXW6 | Q969H0 | Fbox | AF411971 | 55294 | NM_033632; NM_018315 | Hs.519029 | FBOX; WD |
| FBXW8/FBXO29 | Q8N3Y1 | Fbox | BC037296 | 26259 | NM_153348; NM_012174 | Hs.435466 | FBOX; WD |
| FBXW9 | Q5XUX1 | Fbox | AY736034 | 84261 | NM_032301 | Hs.515154 | FBOX; WD |
| FBXW15 | Q8BI39 | Fbox | AK087669 | | | | FBOX |
| FBXW16 | Q8BIU6 | Fbox | AK085629 | | | | FBOX |
| FBXW17 | Q8CFE8 | Fbox | BC040428 | | | | FBOX |

TABLE 23-continued

E3 Ligases, F-box type.
F-box

| Name | UniProt | Type | Genbank | LL | Refseq | Unigene | Domains |
|---|---|---|---|---|---|---|---|
| FBXW19 | Q8C2W8 | Fbox | AK087808 | | | | FBOX |
| FBXO12/FBXW14 | Q8C2Y5 | Fbox | AK087709 | | | | FBOX |
| FBXO19 and FBXW13 do not exist? FBXO20 and FBXO23 clearly contain no Fbox | | | | | | | |

TABLE 24

E3 Ligases, SOCS-box type.
SOCS-box

| Name | UniProt | Type | Genbank | LL | Refseq | Unigene | Domains |
|---|---|---|---|---|---|---|---|
| TULP4 | Q9NRJ4 | SOCS | AF219946 | 56995 | NM_020245; NM_001007466 | Hs.486993 | SOCS; TUBBY; WD |
| WSB1 | Q9Y6I7 | SOCS | AF072880 | 26118 | NM_015626; NM_134264; NM_134265 | Hs.446017 | SOCS; WD |
| WSB2 | Q9NYS7 | SOCS | AF229181 | 55884 | NM_018639 | Hs.506985 | SOCS; WD |
| ASB1 | Q9Y576 | SOCS | AF156777 | 51665 | NM_016114 | Hs.516788 | SOCS; ANK |
| ASB2 | Q96Q27 | SOCS | AB056723 | 51676 | NM_016150 | Hs.510327 | SOCS; ANK |
| ASB3 | Q9Y575 | SOCS | AF156778 | 51130 | NM_145863; NM_016115 | Hs.40763 | SOCS; ANK |
| ASB4 | Q9Y574 | SOCS | AF156779 | 51666 | NM_016116; NM_145872 | Hs.127735 | SOCS; ANK |
| ASB5 | Q8WWX0 | SOCS | AY057053 | 140458 | NM_080874 | Hs.352364 | SOCS; ANK |
| ASB6 | Q9NWX5 | SOCS | AK000555 | 140459 | NM_177999; NM_017873 | Hs.125037 | SOCS; ANK |
| ASB7 | Q9H672 | SOCS | AF451994 | 140460 | NM_198243; NM_024708 | Hs.31845 | SOCS; ANK |
| ASB8 | Q9H765 | SOCS | AK024908 | 140461 | NM_024095 | Hs.432699 | SOCS; ANK |
| ASB9 | Q96DX5 | SOCS | BC013172 | 140462 | NM_024087 | Hs.19404 | SOCS; ANK |
| ASB10 | Q8WXI3 | SOCS | AF417920 | 136371 | NM_080871 | Hs.304273 | SOCS; ANK |
| ASB11 | Q8WXH4 | SOCS | AF425642 | 140456 | NM_080873 | Hs.352183 | SOCS; ANK |
| ASB12 | Q8WXK4 | SOCS | AF403030 | 142689 | NM_130388 | Hs.56281 | SOCS; ANK |
| ASB13 | Q8WXK3 | SOCS | CR457302 | 79754 | NM_024701 | Hs.445899 | SOCS; ANK |
| ASB14 | Q8WXK2 | SOCS | AF403032 | 142686 | NM_130387 | Hs.435978 | SOCS; ANK |
| ASB15 | Q8WXK1 | SOCS | AK125360 | 142685 | NM_080928 | Hs.97709 | SOCS; ANK |
| ASB16 | Q96NS5 | SOCS | AK054727 | 92591 | NM_080863 | Hs.534517 | SOCS; ANK |
| ASB17 | Q8WXJ9 | SOCS | AK098606 | 127247 | NM_080868 | Hs.125423 | SOCS; ANK |
| RAB40A | Q8WXH6 | SOCS | AF422143 | 142684 | NM_080879 | Hs.549244 | SOCS; GTPase |
| RAB40B | Q12829 | SOCS | U05227 | 10966 | NM_006822 | Hs.484068 | SOCS; GTPase |
| RAB40C | Q96S21 | SOCS | BC028696 | 57799 | NM_021168 | Hs.459630 | SOCS; GTPase |
| SOCS1 | O15524 | SOCS | AB005043 | 8651 | NM_003745 | Hs.50640 | SOCS; SH2 |
| SOCS2 | O14508 | SOCS | AB004903 | 8835 | NM_003877 | Hs.485572 | SOCS; SH2 |
| SOCS3 | O14543 | SOCS | AB006967 | 9021 | NM_003955 | Hs.527973 | SOCS; SH2 |
| SOCS4 | Q8WXH5 | SOCS | AF424815 | 122809 | NM_199421; NM_080867 | Hs.532610 | SOCS; SH2 |
| SOCS5 | O75159 | SOCS | AF073958 | 9655 | NM_014011; NM_144949 | Hs.468426 | SOCS; SH2 |
| SOCS6 | O14544 | SOCS | AB006968 | 9306 | NM_004232 | Hs.44439 | SOCS; SH2 |
| SOCS7 | O14512 | SOCS | AB005216 | 30837 | NM_014598 | Hs.514132 | SOCS; SH2 |
| CISH | Q9NSE2 | SOCS | D83532 | 1154 | NM_013324; NM_145071 | Hs.8257 | SOCS; SH2 |
| SSB1 | Q96BD6 | SOCS | BC015711 | 80176 | NM_025106 | Hs.8261 | SOCS; SPRY |
| SSB3 | Q96IE6 | SOCS | BC007588 | 90864 | NM_080861 | Hs.7247 | SOCS; SPRY |
| SSB4 | Q96A44 | SOCS | AK056367 | 92369 | NM_080862 | Hs.477752 | SOCS; SPRY |
| GRCC9/SSB2 | Q99619 | SOCS | AF403027 | 84727 | NM_032641 | Hs.479856 | SOCS; SPRY |
| LOC196394 | Q8IY45 | SOCS | BC037897 | 196394 | NM_207337 | Hs.131393 | SOCS; LRR |
| TCEB3 | Q14241 | SOCS | L47345 | 6924 | NM_003198 | Hs.549069 | SOCS; TFIIS |
| TCEB3B | Q8IYF1 | SOCS | BC036022 | 51224 | NM_016427 | Hs.375035 | SOCS; TFIIS |
| TCEB3C | Q8NG57 | SOCS | AB076840 | 162699 | NM_145653 | Hs.515381 | SOCS; TFIIS |
| NEURL2 | Q9BR09 | SOCS | AK054821 | 140825 | NM_080749 | Hs.517094 | SOCS; Neuralized |
| VHL | P40337 | SOCS | L15409 | 7428 | NM_000551; NM_198156 | Hs.421597 | SOCS; VHL_HYPRO |

TABLE 25

E3 Ligases, BTB type.
BTB

| Name | UniProt | Type | Genbank | LL | Refseq | Unigene | Domains |
|---|---|---|---|---|---|---|---|
| ABTB1 | Q969K4 | BTB | AB053325 | 80325 | NM_172028; NM_172027; NM_032548 | Hs.107812 | ANK; BTB |
| ABTB2 | Q8N961 | BTB | AK095632 | 25841 | NM_145804 | Hs.23361 | ANK; BTB |
| ANKFY1 | Q9P2R3 | BTB | AK025483 | 51479 | NM_016376; NM_020740 | Hs.513875 | ANK; FYVE; BTB |
| APM-1 | O73453 | BTB | Y14591 | none | XM_113971 | Hs.515388 | BTB; ZFb |
| BACH1 | O14867 | BTB | AB002803 | 571 | NM_001186; NM_206866 | Hs.154276 | bZIP; BTB |
| BACH2 | Q9BYV9 | BTB | AF357835 | 60468 | NM_021813 | Hs.269764 | bZIP; BTB |
| BCL6/ZBTB27 | P41182 | BTB | Z21943 | 604 | NM_001706; NM_138931 | Hs.478588 | BTB; ZFb |
| BCL6B/ZBTB28 | Q8N143 | BTB | AB076580 | 255877 | NM_181844 | Hs.22575 | BTB; ZFb |
| BKLHD5/KIAA1900 | Q96NJ5 | BTB | AK055292 | 114792 | NM_052904 | Hs.45056 | BTB; KELCH |
| BTBD1 | Q9H0C5 | BTB | AL136853 | 53339 | NM_025238 | Hs.459149 | BTB |
| BTBD11/FLJ42845 | Q6ZV99 | BTB | AK124835 | 121551 | NM_152322 | Hs.271272 | ANK; BTB |
| BTBD12 | Q8IY92 | BTB | BC036335 | none | none | Hs.513297 | BTB |
| BTBD14A | Q96BF6 | BTB | BC015649 | 138151 | NM_144653 | Hs.112895 | BTB |
| BTBD14B | Q96RE7 | BTB | AF395817 | 112939 | NM_052876 | Hs.531614 | BTB |
| BTBD2 | Q9BX70 | BTB | AF355797 | 55643 | NM_017797 | Hs.465543 | BTB |
| BTBD3 | Q9Y2F9 | BTB | AB023169 | 22903 | NM_014962; NM_181443 | Hs.244590 | BTB |
| BTBD4 | Q86UZ6 | BTB | AK131482 | 140685 | NM_025224 | Hs.551578 | BTB; ZFb |
| BTBD5 | Q9NXS3 | BTB | BC012473 | 54813 | NM_017658 | Hs.174682 | BTB; KELCH |
| BTBD6 | Q96KE9 | BTB | AF353674 | 90135 | NM_033271 | Hs.7367 | BTB |
| BTBD7/KIAA1525 | Q9P203 | BTB | AB040958 | 55727 | NM_018167; NM_001002860 | Hs.525549 | BTB |
| BTBD8 | Q5XKL5 | BTB | BC013922 | 284697 | NM_183242 | Hs.383108 | BTB |
| BTBD9 | Q96Q07 | BTB | AB067467 | 114781 | NM_152733 | Hs.116233 | BTB |
| C10orf87 | Q96LN0 | BTB | AK058088 | 118663 | NM_144587 | Hs.422466 | BTB |
| C16orf44 | Q8N4N3 | BTB | BC033821 | 79786 | NM_024731 | Hs.222731 | BTB; KELCH |
| CCIN | Q13939 | BTB | AF333334 | 881 | NM_005893 | Hs.115460 | BTB; KELCH |
| CHC1L | O95199 | BTB | AF060219 | 1102 | NM_001268 | Hs.25447 | BTB; RCC |
| DRE1 | Q6TFL4 | BTB | AY422472 | 54800 | NM_017644 | Hs.407709 | BTB; KELCH |
| ENC1 | O14682 | BTB | AF059611 | 8507 | NM_003633 | Hs.104925 | BTB; KELCH |
| ENC2/DKFZp434K111 | Q9H0H3 | BTB | AL136796 | 64410 | NM_022480 | Hs.498371 | BTB; KELCH |
| FLJ11078 | Q8TAP0 | BTB | BC026319 | 55295 | NM_018316 | Hs.250632 | BTB; KELCH |
| FLJ34960 | Q8N239 | BTB | AK092279 | 257240 | NM_153270 | Hs.448572 | BTB; KELCH |
| FLJ35036 | Q8NAP3 | BTB | AK092355 | none | XM_172341 | Hs.518301 | ZFb |
| FLJ43374 | Q6ZUS1 | BTB | AK125364 | 377007 | NM_198582 | Hs.199821 | BTB |
| FRBZ1 | Q8IZ99 | BTB | AY163816 | 360023 | NM_194314 | Hs.529439 | BTB; ZFb |
| GAN/KLHL16 | Q9H2C0 | BTB | AF291673 | 8139 | NM_022041 | Hs.112569 | BTB; KELCH |
| GENSCAN00000050486H | GENSCAN00000050486H | BTB | GENSCAN00000050486 | none | XM_371078 | Hs.211870 | BTB |
| GMCL1/GCL | Q96IK5 | BTB | BC007420 | 64395 | NM_178439 | Hs.293971 | BTB |
| GMCL1L | Q8NEA9 | BTB | BC033886 | 64396 | NM_022471 | Hs.484313 | BTB |
| HIC1/ZBTB29 | Q14526 | BTB | BC030208 | 3090 | NM_006497 | Hs.72956 | BTB; ZFb |
| HIC2/ZBTB30 | Q96JB3 | BTB | CR456377 | 23119 | NM_015094 | Hs.517434 | BTB; ZFb |
| HKR3 | P10074 | BTB | BC013573 | 3104 | NM_005341 | Hs.502330 | BTB; ZFb |
| HSPC063 | Q8NCP5 | BTB | BC030580 | 29068 | NM_014155 | Hs.178499 | BTB; ZFb |
| IBTK | Q9P2D0 | BTB | AB037838 | 25998 | NM_015525 | Hs.306425 | ANK; BTB; RCC |
| IPP | Q9Y573 | BTB | AF156857 | 3652 | NM_005897 | Hs.157180 | BTB; KELCH |
| IVNS1ABP | Q9Y6Y0 | BTB | AB020657 | 10625 | NM_016389; NM_006469 | Hs.497183 | BTB; KELCH |
| KBTBD10 | O60662 | BTB | AF333387 | 10324 | NM_006063 | Hs.50550 | BTB; KELCH |
| KBTBD2 | Q8IY47 | BTB | BC032367 | 25948 | NM_015483 | Hs.372541 | BTB; KELCH |
| KBTBD3 | Q8NAB2 | BTB | BX640672 | 143879 | NM_198439; NM_152433 | Hs.101949 | BTB; KELCH |
| KBTBD4 | Q9NVX7 | BTB | AK001749 | 55709 | NM_018095; NM_016506 | Hs.440695 | BTB; KELCH |
| KBTBD5 | Q86SI1 | BTB | AY177390 | 131377 | NM_152393 | Hs.350288 | BTB; KELCH |
| KBTBD6 | Q86V97 | BTB | BC000560 | 89890 | NM_152903 | Hs.534040 | BTB; KELCH |
| KBTBD7 | Q8WVZ9 | BTB | BC022033 | 84078 | NM_032138 | Hs.63841 | BTB; KELCH |
| KBTBD9 | Q96CT2 | BTB | BC013982 | none | XM_496546 | Hs.130593 | BTB; KELCH |
| KEAP1/KLHL19 | Q14145 | BTB | D50922 | 9817 | NM_203500; NM_012289 | Hs.465870 | BTB; KELCH |
| KELCHL | Q96B68 | BTB | BC015923 | 84861 | NM_032775 | Hs.517419 | BTB; KELCH |
| KIAA0352 | O15060 | BTB | AB002350 | 9880 | NM_014830 | Hs.131212 | BTB; ZFb |
| KIAA0478 | Q9NUA8 | BTB | AK091019 | 9923 | NM_014870 | Hs.528723 | BTB; ZFb |
| KIAA0711 | O94819 | BTB | AB018254 | 9920 | NM_014867 | Hs.5333 | BTB; KELCH |
| KIAA1340 | Q9P2K6 | BTB | AK095405 | 57542 | NM_020782 | Hs.505104 | BTB; KELCH |
| KLEIP/KLHL20 | Q9Y2M5 | BTB | AB026190 | 27252 | NM_014458 | Hs.495035 | BTB; KELCH |
| KLHL1 | Q9NR64 | BTB | AF252283 | 57626 | NM_020866 | Hs.508201 | BTB; KELCH |
| KLHL10 | Q6JEL2 | BTB | AY495339 | 317719 | NM_152467 | Hs.127510 | BTB; KELCH |
| KLHL11 | Q9NVR0 | BTB | AK001434 | 55175 | NM_018143 | Hs.13268 | BTB; KELCH |
| KLHL12 | Q9HBX5 | BTB | AF190900 | 59349 | NM_021633 | Hs.282878 | BTB; KELCH |

TABLE 25-continued

E3 Ligases, BTB type.
BTB

| Name | UniProt | Type | Genbank | LL | Refseq | Unigene | Domains |
|---|---|---|---|---|---|---|---|
| KLHL13 | Q9P2N7 | BTB | AB037730 | 90293 | NM_033495 | Hs.348262 | BTB; KELCH |
| KLHL14 | Q9P2G3 | BTB | AB037805 | 57565 | NM_020805 | Hs.446164 | BTB; KELCH |
| KLHL15 | Q96M94 | BTB | AK057298 | none | XM_040383 | Hs.495854 | BTB; KELCH |
| KLHL17 | Q6TDP4 | BTB | AY423763 | 339451 | NM_198317 | Hs.109212 | BTB; KELCH |
| KLHL18 | O94889 | BTB | AB062478 | 23276 | NM_025010 | Hs.517946 | BTB; KELCH |
| KLHL2 | O95198 | BTB | BC036468 | 11275 | NM_007246 | Hs.388668 | BTB; KELCH |
| KLHL21 | Q9UJP4 | BTB | AB007938 | 9903 | NM_014851 | Hs.7764 | BTB; KELCH |
| KLHL3 | Q9UH77 | BTB | AB032955 | 26249 | NM_017415 | Hs.434434 | BTB; KELCH |
| KLHL4 | Q9C0H6 | BTB | AF284765 | 56062 | NM_019117; NM_057162 | Hs.49075 | BTB; KELCH |
| KLHL5 | Q96PQ7 | BTB | BC053860 | 51088 | NM_199039; NM_001007075 | Hs.272251 | BTB; KELCH |
| KLHL6 | Q8WZ60 | BTB | AK097125 | 89857 | NM_130446 | Hs.333181 | BTB; KELCH |
| KLHL7 | Q8IXQ5 | BTB | BC039585 | 55975 | NM_018846 | Hs.385861 | BTB; KELCH |
| KLHL8 | Q9P2G9 | BTB | BC041384 | 57563 | NM_020803 | Hs.546415 | BTB; KELCH |
| KLHL9 | Q9P2J3 | BTB | AB037775 | 55958 | NM_018847 | Hs.522029 | BTB; KELCH |
| LGALS3BP | Q08380 | BTB | L13210 | 3959 | NM_005567 | Hs.514535 | SRCR; BTB |
| LOC149478 | GENSCAN00000058813H | BTB | AK056150 | none | XM_378860 | Hs.421430 | BTB |
| LOC339745 | Q6IQ16 | BTB | BC071613 | 339745 | NM_001001664 | Hs.333297 | TRAF; BTB |
| LZTR1 | Q8N653 | BTB | BC026214 | 8216 | NM_006767 | Hs.78788 | BTB; KELCH |
| MGC2610 | Q8NBE8 | BTB | AK090653 | 151230 | NM_144711 | Hs.470549 | BTB; KELCH |
| MYNN/ZBTB31 | Q86Z12 | BTB | AB079777 | 55892 | NM_018657 | Hs.507025 | BTB; ZFb |
| OTTHUMP00000016633 | Q9H511 | BTB | AK091177 | 401265 | NM_001003760 | Hs.376697 | BTB; KELCH |
| RCBTB1 | Q8NDN9 | BTB | AL833821 | 55213 | NM_018191 | Hs.508021 | BTB; RCC |
| RHOBTB1 | O94844 | BTB | AB018283 | 9886 | NM_198225; NM_014836 | Hs.148670 | GTPase; BTB |
| RHOBTB2 | Q9BYZ6 | BTB | AB018260 | 23221 | NM_015178 | Hs.372688 | GTPase; BTB |
| RHOBTB3 | O94955 | BTB | AB020685 | 22836 | NM_014899 | Hs.445030 | BTB |
| SPOP | O43791 | BTB | AJ000644 | 8405 | NM_003563; NM_001007226; NM_001007227; NM_001007230; NM_001007229; NM_001007228 | Hs.463382 | TRAF; BTB |
| TA-KRP/KIAA1842 | Q96JI5 | BTB | AB058745 | 84541 | NM_032505 | Hs.116665 | BTB; KELCH |
| TZFP/FAZF | Q9Y2Y4 | BTB | AF130255 | 27033 | NM_014383 | Hs.99430 | BTB; ZFb |
| ZBTB1 | Q9Y2K1 | BTB | BX248777 | 22890 | NM_014950 | Hs.400802 | BTB; ZFb |
| ZBTB10 | Q96DT7 | BTB | AJ319673 | 65986 | NM_023929 | Hs.205742 | BTB; ZFb |
| ZBTB11 | O95625 | BTB | U69274 | 27107 | NM_014415 | Hs.301956 | BTB; ZFb |
| ZBTB12 | Q9Y330 | BTB | AF134726 | 221527 | NM_181842 | Hs.234027 | BTB; ZFb |
| ZBTB16 | Q05516 | BTB | Z19002 | 7704 | NM_006006 | Hs.171299 | BTB; ZFb |
| ZBTB17 | Q13105 | BTB | Y09723 | 7709 | NM_003443 | Hs.433764 | BTB; ZFb |
| ZBTB2 | Q8N680 | BTB | BC020172 | 57621 | NM_020861 | Hs.520073 | BTB; ZFb |
| ZBTB20 | Q9HC78 | BTB | AF139460 | 26137 | NM_015642 | Hs.477166 | BTB; ZFb |
| ZBTB24 | O43167 | BTB | AB007901 | 9841 | NM_014797 | Hs.409876 | BTB; ZFb |
| ZBTB26 | Q9HCK0 | BTB | AF323460 | 57684 | NM_020924 | Hs.5638 | BTB; ZFb |
| ZBTB3 | Q9H5J0 | BTB | AK027045 | 79842 | NM_024784 | Hs.147554 | BTB; ZFb |
| ZBTB33/kaiso | Q86T24 | BTB | AL833604 | 10009 | NM_006777 | Hs.143604 | BTB; ZFb |
| ZBTB34 | Q8NCN2 | BTB | AB082524 | none | none | Hs.177633 | BTB; ZFb |
| ZBTB37 | Q5TC79 | BTB | BC003116 | 84614 | NM_032522 | Hs.535229 | BTB; ZFb |
| ZBTB4 | Q9P1Z0 | BTB | AY302699 | 57659 | NM_020899 | Hs.35096 | BTB; ZFb |
| ZBTB5 | O15062 | BTB | AB002352 | 9925 | NM_014872 | Hs.161276 | BTB; ZFb |
| ZBTB7A | O95365 | BTB | AF097916 | 51341 | NM_015898 | Hs.465623 | BTB; ZFb |
| ZBTB8a | Q8NAP8 | BTB | AK092326 | 127557 | NM_144621 | Hs.546479 | BTB; ZFb |
| ZBTB8b | Q96BR9 | BTB | BC015239 | 127557 | NM_144621 | Hs.546479 | BTB; ZFb |
| ZBTB9 | Q96C00 | BTB | BC014978 | 221504 | NM_152735 | Hs.528028 | BTB; ZFb |
| ZFP161/ZBTB14 | O43829 | BTB | Y12726 | 7541 | NM_003409 | Hs.156000 | BTB; ZFb |
| ZFP67/ZBTB7B/ZBTB15 | O15156 | BTB | BC012070 | 51043 | NM_015872 | Hs.549155 | BTB; ZFb |
| ZNF131 | P52739 | BTB | AK057343 | none | none | Hs.97845 | BTB; ZFb |
| ZNF238/ZBTB18 | Q99592 | BTB | X95072 | 10472 | NM_205768; NM_006352 | Hs.69997 | BTB; ZFb |
| ZNF278/ZBTB19 | Q9HBE1 | BTB | AF254085 | 23598 | NM_032051; NM_014323; NM_032052; NM_032050 | Hs.517557 | BTB; ZFb |
| ZNF295/ZBTB21 | Q9ULJ3 | BTB | AB033053 | 49854 | NM_020727 | Hs.434947 | BTB; ZFb |
| ZNF297/ZBTB22A | O15209 | BTB | Z97184 | 9278 | NM_005453 | Hs.206770 | BTB; ZFb |
| ZNF297B/ZBTB22B | O43298 | BTB | AB007874 | 23099 | NM_014007 | Hs.355581 | BTB; ZFb |
| ZNF336/ZBTB23 | Q9H116 | BTB | AB100265 | 64412 | NM_022482 | Hs.28921 | BTB; ZFb |

TABLE 25-continued

E3 Ligases, BTB type.
BTB

| Name | UniProt | Type | Genbank | LL | Refseq | Unigene | Domains |
|---|---|---|---|---|---|---|---|
| ZNF46/ZBTB25 | P24278 | BTB | X16576 | 7597 | NM_006977 | Hs.164347 | BTB; ZFb |
| ZNF482/ZBTB6 | Q15916 | BTB | X82018 | 10773 | NM_006626 | Hs.3053 | BTB; ZFb |
| ZNF499 | Q96K62 | BTB | AK027392 | 84878 | NM_032792 | Hs.515662 | BTB; ZFb |
| ZNF509/FLJ45653 | Q6ZSB9 | BTB | AK127560 | 166793 | NM_145291 | Hs.419997 | BTB; ZFb |
| ZNF651/FLJ45122 | Q6ZSY6 | BTB | AK127065 | 92999 | NM_145166 | Hs.409561 | BTB; ZFb |

TABLE 26

E3 Ligases, DDB1-like type.
DDB1-like

| Name | UniProt | Type | Genbank | LL | Refseq | Unigene | Domains |
|---|---|---|---|---|---|---|---|
| CPSF1 | Q10570 | DDB1 | BC017232 | 29894 | NM_013291 | Hs.493202 | DDB1 |
| DDB1 | Q16531 | DDB1 | U18299 | 1642 | NM_001923 | Hs.290758 | DDB1 |
| SF3B3 | Q15393 | DDB1 | AJ001443 | 23450 | NM_012426 | Hs.514435 | DDB1 |

TABLE 27

E3 Ligases, APC/Cyclosome type.
APC/Cyclosome

| Name | UniProt | Type | Genbank | LL | Refseq | Unigene | Domains |
|---|---|---|---|---|---|---|---|
| ANAPC1 | Q9H1A4 | APC | AJ278357 | 64682 | NM_022662 | Hs.436527 | PC-rep |
| ANAPC2 | Q9UJX6 | APC | BC032503 | 29882 | NM_013366 | Hs.533262 | CULLIN |
| CDC16 | Q13042 | APC | AL540490 | 8881 | NM_003903 | Hs.374127 | TPR |
| CDC27 | P30260 | APC | AU135593 | 996 | NM_001256 | Hs.463295 | TPR |
| ANAPC5 | Q9UJX4 | APC | BC006301 | 51433 | NM_016237 | Hs.7101 | |
| ANAPC4 | Q9UJX5 | APC | AL353932 | 29945 | NM_013367 | Hs.152173 | |
| CDC23 | Q9UJX2 | APC | AB011472 | 8697 | NM_004661 | Hs.153546 | TPR |
| ANAPC7 | Q9UJX3 | APC | AF191340 | 51434 | NM_016238 | Hs.529280 | |
| ANAPC10 | Q9UM13 | APC | AL080090 | 10393 | NM_014885 | Hs.480876 | |
| ANAPC11 | Q9NYG5 | APC | BC000607 | 51529 | NM_001002249; NM_016476; NM_001002246; NM_001002248; NM_001002244; NM_001002247; NM_001002245 | Hs.534456 | RF |
| CDC26 | Q8NHZ8 | APC | BC042534 | 246184 | NM_139286 | Hs.530284 | |
| CDC20 | Q12834 | APC | U05340 | 991 | NM_001255 | Hs.524947 | WD |
| FZR1 | Q9UM11 | APC | AB033068 | 51343 | NM_016263 | Hs.413133 | WD |

A particular E3 ubiquitin ligase is von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. Compounds that bind VHL may be hydroxyproline compounds such as those disclosed in WO2013/106643, and other compounds described in US2016/0045607, WO2014187777, US20140356322, and U.S. Pat. No. 9,249,153.

Another particular E3 ubiquitin ligase is MDM2. Examples of small molecular binding compounds for MDM2 include the "nutlin" compounds, e.g., nutlin 3a and nutlin 3, having the structure:

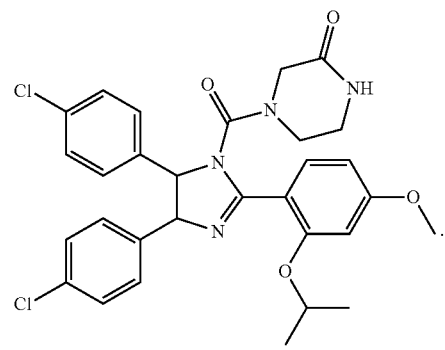 [SMILES: COc1ccc(C2=NC(c3ccc(Cl)cc3)C(c3ccc(Cl)cc3)N2C(=O)N2CCNC(=O)C2)c(OC(C)C)c1]

Also included as MDM2 binding compounds are those described in WO2012/121361; WO2014/038606; WO2010/082612; WO2014/044401; WO2009/151069; WO2008/072655; WO2014/100065; WO2014/100071; WO2014/

123882; WO2014/120748; WO2013/096150; WO2015/161032; WO2012/155066; WO2012/065022; WO2011/060049; WO2008/036168; WO2006/091646; WO2012/155066; WO2012/065022; WO2011/153509; WO2013/049250; WO2014/151863; WO2014/130470; WO2014/134207; WO2014/200937; WO2015/070224; WO2015/158648; WO2014/082889; WO2013/178570; WO2013/135648; WO2012/116989; WO2012/076513; WO2012/038307; WO2012/034954; WO2012/022707; WO2012/007409; WO2011/134925; WO2011/098398; WO2011/101297; WO2011/067185; WO2011/061139; WO2011/045257; WO2010/121995; WO2010/091979; WO2010/094622; WO2010/084097; WO2009/115425; WO2009/080488; WO2009/077357; WO2009/047161A1; WO2008/141975A1; WO2008/141917A1; WO2008/125487A1; WO2008/034736A2; WO2008/055812A1; WO2007/104714A1; WO2007/104664A1; WO2007/082805A1; WO2007/063013A1; WO2006/136606A2; WO2006/097261A1; WO2005/123691A1; WO2005/110996A1; WO2005/003097A1; WO2005/002575A1; WO2004/080460A1; WO2003/051360A1; WO2003/051359A1; WO 1998/001467; WO2011/023677; WO2011/076786; WO2012/066095; WO2012/175487; WO2012/175520; WO2012/176123; WO2013/080141; WO2013/111105; WO2013/175417; WO2014/115080; WO2014/115077; WO2014/191896; WO2014/198266; WO2016/028391A9; WO2016/028391A2; WO2016/026937; WO2016/001376; WO2015/189799; WO2015/155332A1; WO2015/004610A8; WO2013/105037A1; WO2012/155066A3; WO2012/155066A2; WO2012/033525A3; WO2012/047587A2; WO2012/033525A2; WO2011/106650A3; WO2011/106650A2; WO2011/005219A1; WO2010/058819A1; WO2010/028862A1; WO2009/037343A1; WO2009/037308A1; WO2008/130614A3; WO2009/019274A1; WO2008/130614A2; WO2008/106507A3; WO2008/106507A2; WO2007/107545A1; WO2007/107543A1; WO2006032631A1; WO2000/015657A1; WO 1998/001467A2; WO1997/009343A3; WO1997/009343A2; WO1996/002642A1; US2007/0129416; Med. Chem. Lett, 2013, 4, 466-469; J. Med. Chem., 2015, 58, 1038-1052; Bioorg. Med. Chem. Lett. 25 (2015) 3621-3625; Bioorg. Med. Chem. Lett. 16 (2006) 3310-3314. Further specific examples of small molecular binding compounds for MDM2 contemplated for use with a PAC include RG7112, RG7388, MI 773/SAR 405838, AMG 232, DS-3032b, RO6839921, RO5045337, RO5503781, Idasanutlin, CGM-097, MK-8242

Another particular E3 ubiquitin ligase is X-linked inhibitor of apoptosis (XIAP). XIAP is a protein that stops apoptotic cell death. Deregulation of XIAP has been associated with cancer, neurodegenerative disorders and autoimmunity. In the development of lung cancer, the overexpression of XIAP inhibits caspases. In developing prostate cancer, XIAP is one of four IAPs overexpressed in the prostatic epithelium. Mutations in the XIAP gene can result in a severe and rare type of inflammatory bowel disease. Defects in the XIAP gene can also result in an extremely rare condition called X-linked lymphoproliferative disease. Degradation of XIAP can enhance apoptosis by preventing XIAP from binding to caspases. This allows normal caspase activity to proceed.

Examples of small molecular binding compounds for XIAP include compounds disclosed in U.S. Pat. No. 9,096,544; WO 2015187998; WO 2015071393; U.S. Pat. Nos. 9,278,978; 9,249,151; US 20160024055; US 20150307499; US 20140135270; US 20150284427; US 20150259359; US 20150266879; US 20150246882; US 20150252072; US 20150225449; U.S. Pat. No. 8,883,771, J. Med. Chem., 2015, 58(16) 6574-6588 and Small-molecule Pan-IAP Antagonists: A Patent Review (2010) Expert Opin Ther Pat; 20: 251-67 (Flygare & Fairbrother). Specific compounds include all the tetrahydro-benzodiazinone compounds of the following formula:

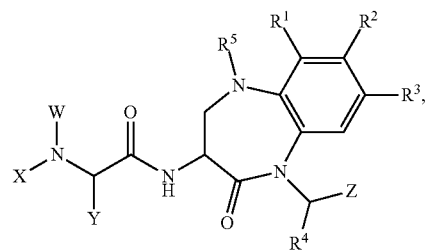

as disclosed in WO 2015/071393. Other small molecular binding compounds for XIAP include AEG35156, Embelin, TWX006 and TWX024. When an XIAP bindig moeity is used as part of a PROTAC, the XIAP binding moiety can bind to the BIR2 or BIR3 domain of XIAP or both.

Another particular E3 ubiquitin ligase is cereblon. Cereblon is a protein that forms an E3 ubiquitin ligase complex with damaged DNA binding protein 1 (DDB1), Cullin-4A (CUL4A), and regulator of cullins 1 (ROC 1). This complex ubiquitinates a number of other proteins. Cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. In the absence of cereblon, DDB1 forms a complex with DDB2 that functions as a DNA damage-binding protein.

Thalidomide, lenalidomide, pomalidomide and analogs thereof are known to bind to cereblon. The crystal structure of cereblon with thalidomide and derivative compounds are described in US2015/0374678. Other small molecule compounds that bind to cereblon are also known, e.g., the compounds disclosed as an in US2016/0058872 and US2015/0291562. Further, phthalimide conjugation with binders, such as antagonists, of BET bromodomains can provide PROTACs with highly-selective cereblon-dependent BET protein degradation. Winter et al., Science, Jun. 19, 2015, p. 1376. Such PROTACs can be conjugated to an antibody as described herein to form a PAC.

b. Protein Binding Group (PB)

The PB component is a group which binds to a target protein intended to be degraded. The term "protein" includes oligopeptides and polypeptide sequences of sufficient length that they can bind to a PB group. Any protein in a eukaryotic system or a microbial system, including a virus, bacteria or fungus, as otherwise described herein, are targets for ubiquitination mediated by the compounds described herein.

PB groups include, for example, any moiety which binds to a protein specifically (binds to a target protein) and includes the following non-limiting examples of small molecule target protein moieties: Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest.

In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

Accordingly, the PB component of a PAC is any peptide or small molecule that bind protein targets such as FoxO1, HDAC, DP-1, E2F, ABL, AMPK, BRK, BRSK I, BRSK2, BTK, CAMKK1, CAMKK alpha, CAMKK beta, Rb, Suv39HI, SCF, p19INK4D, GSK-3, pi 8 INK4, myc, cyclin E, CDK2, CDK9, CDG4/6, Cycline D, p16 INK4A, cdc25A, BMI1, SCF, Akt, CHK1/2, C 1 delta, CK1 gamma, C 2, CLK2, CSK, DDR2, DYRK1A/2/3, EF2K, EPH-A2/A4/B/B2/B3/B4, EIF2A 3, Smad2, Smad3, Smad4, Smad7, p53, p21 Cip1, PAX, Fyn, CAS, C3G, SOS, Ta1, Raptor, RACK-1, CRK, Rap1, Rac, KRas, NRas, HRas, GRB2, FAK, PI3K, spred, Spry, mTOR, MPK, LKB1, PAK 1/2/4/5/6, PDGFRA, PYK2, Src, SRPK1, PLC, PKC, PKA, PKB alpha/beta, PKC alpha/gamma/zeta, PKD, PLK1, PRAK, PRK2, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tpl2/cot1, MEK1, MEK2, PLDL Erk1, Erk2, Erk5, Erk8, p90RSK, PEA-15, SRF, p27 KIP1, TIF 1a, HMGN1, ER81, MKP-3, c-Fos, FGF-R1, GCK, GSK3 beta, HER4, HIPK1/2/3/, IGF-1R, cdc25, UBF, LAMTOR2, Stat1, StaO, CREB, JAK, Src, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, TAK1, JNK1/2/3, Lck, A-Raf, B-Raf, C-Raf, MOS, MLK1/3, MN 1/2, MSK1, MST2/3/4, MPSK1, MEKK1, ME K4, MEL, ASK1, MINK1, MKK 1/2/3/4/6/7, NE 2a/6/7, NUAK1, OSR1, SAP, STK33, Syk, Lyn, PDK1, PHK, PIM 1/2/3, Ataxin-1, mTORC1, MDM2, p21 Waf1, Cyclin D1, Lamln A, Tpl2, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPK1b, MAPKAP-K2 K3, p38 alpha/beta/delta/gamma MAPK, Aurora A, Aurora B, Aurora C, MCAK, Clip, MAPKAPK, FAK, MARK 1/2/3/4, Mucl, SHC, CXCR4, Gap-1, Myc, beta-catenin/TCF, Cbl, BRM, Mcl-1, BRD2, BRD3, BRD4, AR, RAS, ErbB3, EGFR, IRE1, HPK1, RIPK2, and ERα, including all variants, mutations, splice variants, indels and fusions of these target proteins listed.

Specific PB groups are small molecule compounds such as those disclosed in US2014/0356322 and US2016/0045607. Compounds disclosed therein can be classified as Heat Shock Protein 90 (HSP90) inhibitors, Kinase and Phosphatase inhibitors, MDM2 inhibitors, HDAC inhibitors, Human Lysine Methyltransferase Inhibitors, Angiogenesis inhibitors, Immunosuppressive compounds, as well as compounds that target: Human BET Bromodomain-containing proteins, the aryl hydrocarbon receptor (AHR), REF receptor kinase, FKBP, Androgen Receptor (AR), Estrogen receptor (ER), Thyroid Hormone Receptor, HIV Protease, HIV Integrase, HCV Protease, Acyl-protein Thioesterase-1 and -2 (APT and APT2).

c. Linker L2

The E3LB and PB groups of PROTACs as described herein can be connected with linker (L2). In certain embodiments, the linker group L2 is a group comprising one or more covalently connected structural units of A (e.g., —$A_1 \ldots A_q$—), wherein $A_1$ is a group coupled to at least one of a E3LB, a PB, or a combination thereof. In certain embodiments, $A_1$ links a E3LB, a PB, or a combination thereof directly to another E3LB, PB, or combination thereof. In other embodiments, $A_1$ links a EL3B, a PB, or a combination thereof indirectly to another E3LB, PB, or combination thereof through $A_q$.

In certain embodiments, $A_1$ to $A_q$ are, each independently, a bond, $CR^{La}R^{Lb}$, O, S, SO, $SO_2$, $NR^{Lc}$, $SO_2NR^{Lc}$, $SONR^{Lc}$, $CONR^{Lc}$, $NR^{Lc}CONR^{Ld}$, $NR^{Lc}SO_2NR^{Ld}$, CO, $CR^{La}$=$CR^{Lb}$, C≡C, $SiR^{La}R^{Lb}$, $P(O)R^{La}$, $P(O)OR^{La}$, $NR^{Lc}C$(=$NCN$)$NR^{Ld}$, $NR^{Lc}C$(=$NCN$), $NR^{Lc}C$(=$CNO_2$)$NR^{Ld}$, $C_{3-11}$cycloalkyl optionally substituted with 0-6 $R^{La}$ and/or $R^{Lb}$ groups, $C_{3-11}$heterocyclyl optionally substituted with 0-6 $R^{La}$ and/or $R^{Lb}$ groups, aryl optionally substituted with 0-6 $R^{La}$ and/or $R^{Lb}$ groups, heteroaryl optionally substituted with 0-6 $R^{La}$ and/or $R^{Lb}$ groups, where $R^{La}$ or $R^{Lb}$, each independently, can be linked to other A groups to form cycloalkyl and/or heterocyclyl moeity which can be further substituted with 0-4 $R^{Le}$ groups; wherein $R^{La}$, $R^{Lb}$, $R^{Lc}$, $R^{Ld}$ and $R^{Le}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl)$SO_2N(C_{1-8}$alkyl$)_2$, NH $SO_2NH(C_{1-8}$alkyl), NH $SO_2N(C_{1-8}$alkyl$)_2$, NH $SO_2NH_2$.

In certain embodiments, q is an integer greater than or equal to 0. In certain embodiments, q is an integer greater than or equal to 1.

In certain embodiments, e.g., where q is greater than 2, $A_q$ is a group which is connected to an E3LB moiety, and $A_1$ and $A_q$ are connected via structural units of A (number of such structural units of A: q-2).

In certain embodiments, e.g., where q is 2, $A_q$ is a group which is connected to $A_1$ and to an E3LB moiety.

In certain embodiments, e.g., where q is 1, the structure of the linker group L2 is —$A_1$—, and $A_1$ is a group which is connected to an E3LB moiety and a PB moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L2) is selected from the group consisting of):

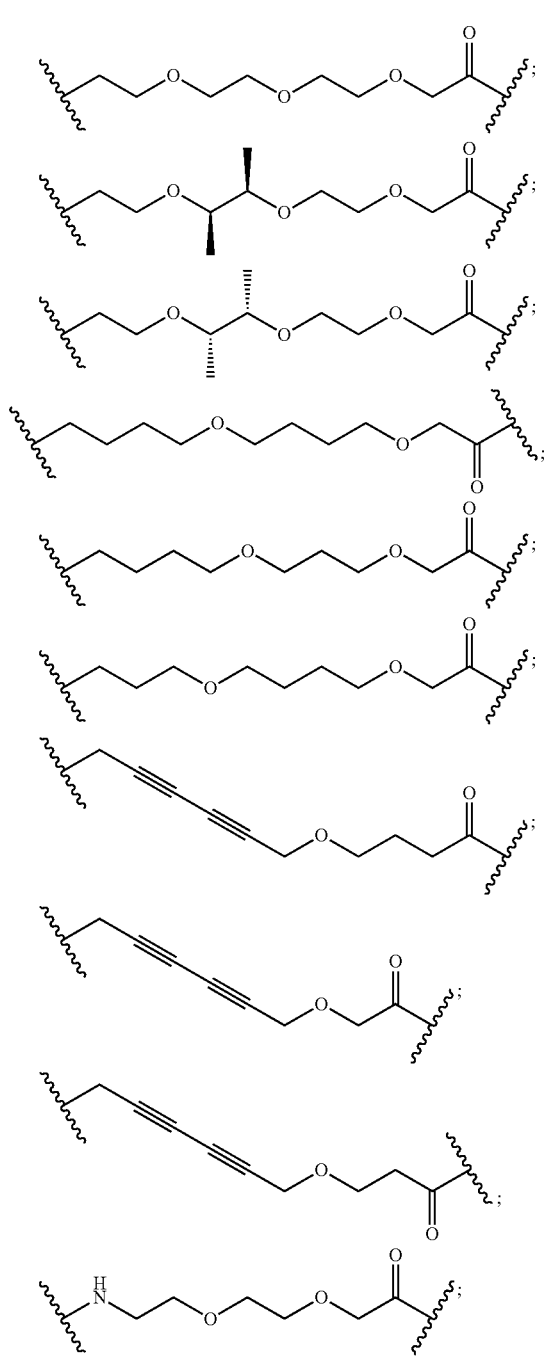

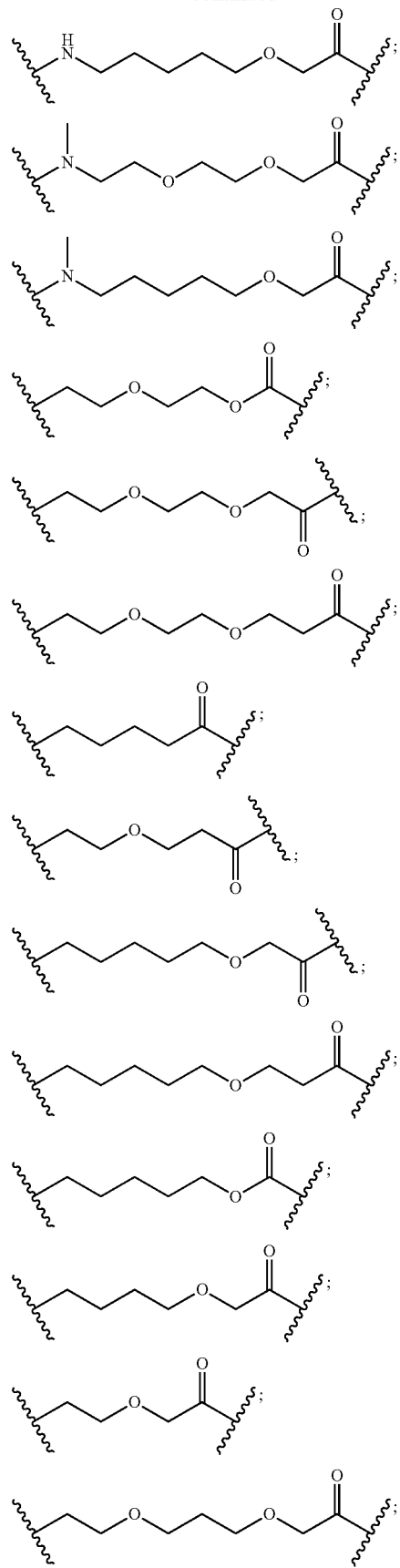

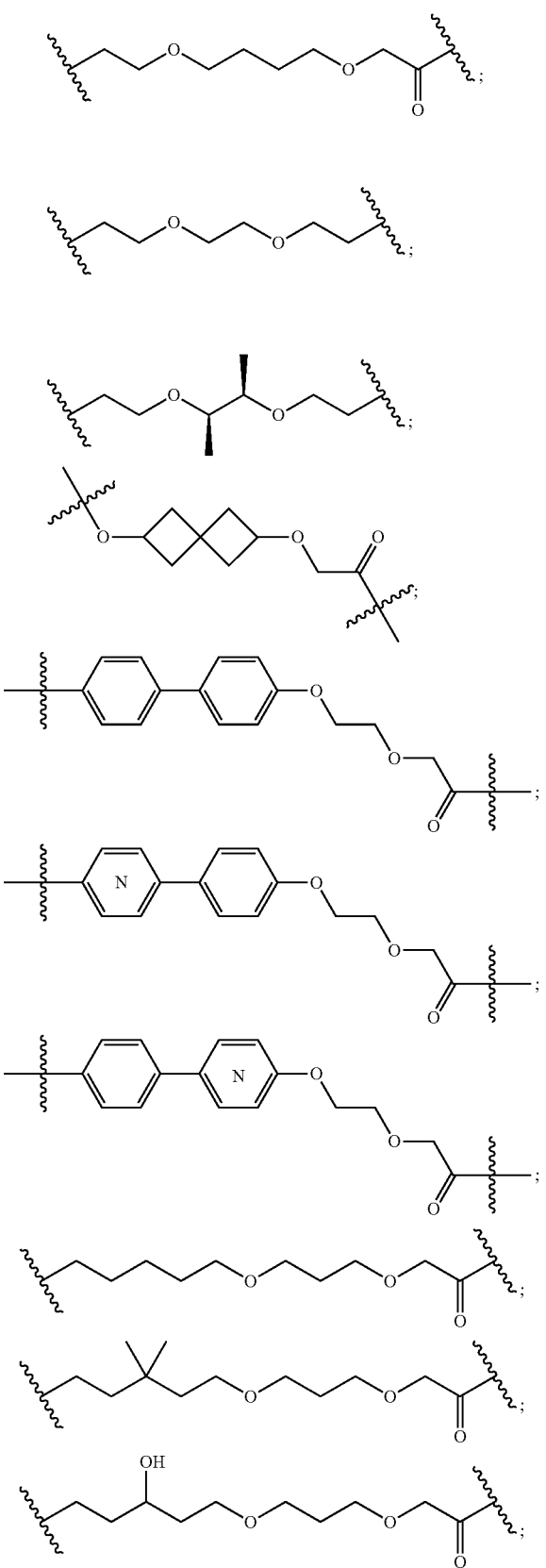

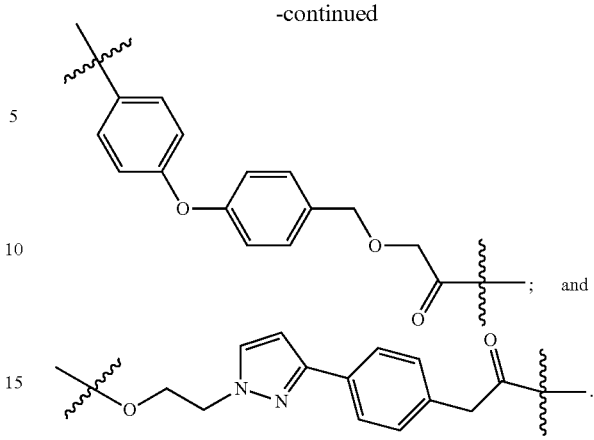

In additional embodiments, the linker group is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the E3LB group and PB group may be covalently linked to the linker group through any group which is appropriate and stable to the chemistry of the linker. The linker is independently covalently bonded to the E3LB group and the PB group preferably through an amide, ester, thioester, keto group, carbamate (urethane), carbon or ether, each of which groups may be inserted anywhere on the E3LB group and PB group to provide maximum binding of the E3LB group on the ubiquitin ligase and the PB group on the target protein to be degraded. In certain aspects where the PB group is an E3LB group, the target protein for degradation may be the ubiquitin ligase itself. In certain aspects, the linker may be linked to an optionally substituted alkyl, alkylene, alkene or alkyne group, an aryl group or a heterocyclic group on the E3LB and/or PB groups. It is noted that an E3LB group or a PB group may need to be derivatized to make a chemical functional group that is reactive with a chemical functional group on the linker. Alternatively, the linker may need to be derivatized to include a chemical functional group that can react with a functional group found on E3LB and/or PB.

L2 can also be represented by the formula:

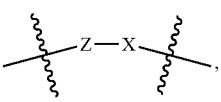

Where Z is a group which links E3LB to X; and X is a group linking Z to group PB.

In embodiments, Z is absent (a bond), —(CH$_2$)i-O, —(CH$_2$)i-S, —(CH$_2$)i-N—R, a (CH$_2$)$_i$—X$_1$Y$_1$ group wherein X$_1$Y$_1$ forms an amide group, or a urethane group, ester or thioester group, or a

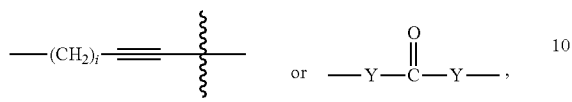

where, each R is H, or a C$_1$-C$_3$ alkyl, an alkanol group or a heterocycle (including a water soluble heterocycle, preferably, a morpholino piperidine or piperazine group to promote water solubility of the linker group); each Y is independently a bond, O, S or N—R; and each i is independently 0 to 100, 1 to 75, 1 to 60, 1 to 55, 1 to 50, 1 to 45, 1 to 40, 2 to 35. 3 to 30, 1 to 15, 1 to 10, 1 to 8, 1 to 6, 1, 2, 3, 4 or 5;

In embodiments, X is a

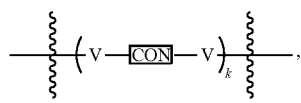

where each V is independently a bond (absent),

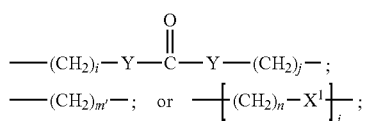

j is 1 to 100, 1 to 75, 1 to 60, 0.1 to 55, 1 to 50, 1 to 45, 1 to 40, 2 to 35, 3 to 30, 1 to 15, 1 to 10, 1 to 8, 1 to 6, 1, 2, 3, 4 or 5;

k is 1 to 100, 1 to 75, 1 to 60, 1 to 55, 1 to 50, 1 to 45, 1 to 40, 2 to 35, 3 to 30, 1 to 15, 1 to 10, 1 to 8, t to 6, 1, 2, 3, 4 or 5; preferably k is 1, 2, 3, 4, or 5;

ln' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10.1108.1 to 6, 1, 2, 3, 4 or 5;

X$^1$ is O, S or N—R, preferably O;

Y is the same as above;

and CON is a connector group (which may be a bond) which connects Z to X, when present in the linker group.

In embodiments, CON is a bond (absent), a heterocycle including a water soluble heterocycle such as a piperazinyl or other group or a group,

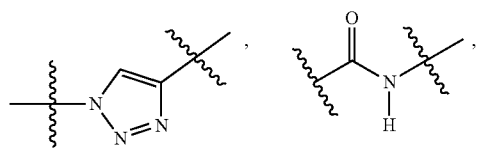

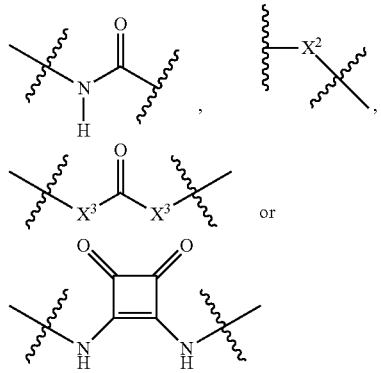

where X$^2$ is O, S, NR$^4$, S(O), S(O)$_2$, —S(O)$_2$0, —OS(O)$_2$, or OS(O)$_2$0;

X$^3$ is O, S, CHR$^4$, NR$^4$; and

R is H. or a C$_1$-C$_3$ alkyl group optionally substituted with one or two hydroxyl groups, or a pharmaceutically acceptable salt, enantiomer or stereoisomer thereof.

in alternative preferred aspects, the linker group is a (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units.

In embodiments, CON is

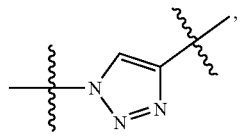 [SMILES: *c1cn(*)nn1]

or an amide group.

Although the E3LB group and PB group may be covalently linked to the linker group through any group which is appropriate and stable to the chemistry of the linker, in preferred aspects, the linker is independently covalently bonded to the E3LB group and the PB group through an amide, ester, thioester, keto group, carbamate (urethane) or ether, each of which groups may be inserted anywhere on the E3LB group and PB group to allow binding of the E3LB group to the ubiquitin ligase and the PB group to the target protein to be degraded. In other words, as shown herein, the linker can be designed and connected to E3LB and PB to minimize, eliminate, or neutralize any impact its presence might have on the binding of E3LB and PB to their respective binding partners. In certain aspects, the targeted protein for degradation may be an ubiquitin ligase.

Additional linkers L2 are disclosed in US Application Publication Nos. 2016/0058872; 2016/0045607; 2014/0356322; and 2015/0291562, and WO2014/063061.

Referring now to a PAC, a PAC can comprise a single antibody where the single antibody can have more than one PROTAC, each PROTAC covalently linked to the antibody through a linker L1. The "PROTAC loading" is the average number of PROTAC moieties per antibody. PROTAC loading may range from 1 to 8 PROTAC (D) per antibody (Ab). That is, in the PAC formula, Ab-(L1-D)$_p$, p has a value from about 1 to about 50, from about 1 to about 8, from about 1 to about 5, from about 1 to about 4, or from about 1 to about 3. Each PROTAC covalently linked to the antibody through linker L1 can be the same or different PROTAC and can have a linker of the same type or different type as any other L1 covalently linked to the antibody. In one embodiment, Ab is a cysteine engineered antibody and p is about 2.

The average number of PROTACs per antibody in preparations of PACs from conjugation reactions may be characterized by conventional means such as mass spectrometry, ELISA assay, electrophoresis, and HPLC. The quantitative distribution of PACs in terms of p may also be determined. By ELISA, the averaged value of p in a particular preparation of PAC may be determined (Hamblett et al (2004) Clin. Cancer Res. 10:7063-7070; Sanderson et al (2005) Clin. Cancer Res. 11:843-852). However, the distribution of the value of p is not discernible by the antibody-antigen binding and detection limitation of ELISA. Also, ELISA assay for detection of PACs does not determine where the PROTAC moieties are attached to the antibody, such as the heavy chain or light chain fragments, or the particular amino acid residues. In some instances, separation, purification, and characterization of homogeneous PACs where p is a certain value from PACs with other PROTAC loadings may be achieved by means such as reverse phase HPLC or electrophoresis.

For some PACs, p may be limited by the number of attachment sites on the antibody. For example, an antibody may have only one or several cysteine thiol groups, or may have only one or several sufficiently reactive thiol groups through which a linker may be attached. Another reactive site on an Ab to connect L1-Ds are the amine functional group of lysine residues. Values of p include values from about 1 to about 50, from about 1 to about 8, from about 1 to about 5, from about 1 about 4, from about 1 to about 3, and where p is equal to 2. In some embodiments, the subject matter described herein is directed to any the PACs, wherein p is about 1, 2, 3, 4, 5, 6, 7, or 8.

Generally, fewer than the theoretical maximum of PROTAC moieties is conjugated to an antibody during a conjugation reaction. An antibody may contain, for example, many lysine residues that do not react with the linker L-PROTAC group (L1-D) or linker reagent. Only the most reactive lysine groups may react with an amine-reactive linker reagent. Also, only the most reactive cysteine thiol groups may react with a thiol-reactive linker reagent or linker L1-PROTAC group. Generally, antibodies do not contain many, if any, free and reactive cysteine thiol groups which may be linked to a PROTAC moiety. Most cysteine thiol residues in the antibodies of the compounds exist as disulfide bridges and must be reduced with a reducing agent such as dithiothreitol (DTT) or TCEP, under partial or total reducing conditions. However, the PROTAC loading (PROTAC/antibody ratio, "PAR") of a PAR may be controlled in several different manners, including: (i) limiting the molar excess of linker L-PROTAC group or linker reagent relative to antibody, (ii) limiting the conjugation reaction time or temperature, and (iii) partial or limiting reductive conditions for cysteine thiol modification.

III. L1-PROTAC Compounds

The PROTACs described herein can be covalently linked to a linker L1 to prepare L1-PROTAC groups. These compounds have the following general formula:

(L1-D), wherein, D is a PROTAC having the structure E3LB-L2-PB; wherein, E3LB is an E3 ligase binding group covalently bound to L2; L2 is a linker covalently bound to E3LB and PB; PB is a protein binding group covalently bound to L2; and L1 is a linker, covalently bound to D. Useful groups for each of these components is as described above.

In particular embodiments, L1 is as described elsewhere herein, including a peptidomimetic linker. In these embodiments, the L-PROTAC has the following formula:

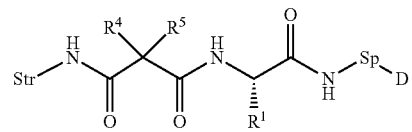

wherein
Str is a stretcher unit;
Sp is a bond or a spacer unit covalently attached to D, i.e., a PROTAC moiety;
$R^1$ is $C_1$-$C_{10}$alkyl, $(C_1$-$C_{10}$alkyl)NHC(NH)NH$_2$ or $(C_1$-$C_{10}$alkyl)NHC(O)NH$_2$;
$R^4$ and $R^5$ are each independently $C_1$-$C_{10}$alkyl, arylalkyl, heteroarylalkyl, $(C_1$-$C_{10}$alkyl)OCH$_2$—, or $R^4$ and $R^5$ may form a $C_3$-$C_7$cycloalkyl ring;
D is a PROTAC moiety.

An L1-PROTAC compound can be represented by the following formula:

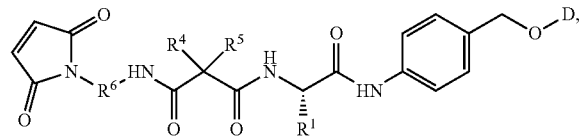

wherein $R_6$ is $C_1$-$C_{10}$alkylene; $R^4$ and $R^5$ together form a $C_3$-$C_7$cycloalkyl ring, and D is a PROTAC moeity.

An L1-PROTAC compound can be represented by the following formula:

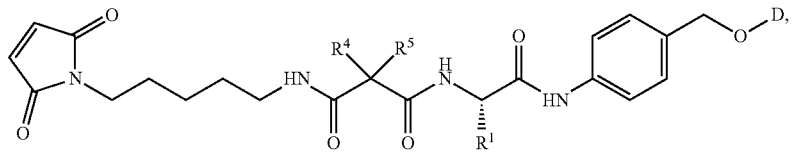

wherein $R^1$, $R^4$ and $R^5$ are as described elsewhere herein, and D is a PROTAC moiety.

An Li-PROTAC compound can be represented by the following formula:

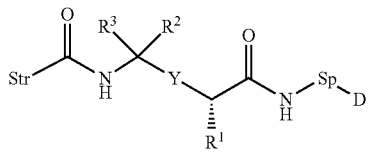

wherein
Str is a stretcher unit;
Sp is an optional spacer unit covalently attached to D, i.e., a PROTAC moiety;
Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;
$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;
$R^3$ and $R^2$ are each independently H, $C_1$-$C_{10}$alkyl, arylalkyl or heteroarylalkyl, or $R^3$ and $R^2$ together may form a $C_3$-$C_7$cycloalkyl; and
D is a PROTAC moiety.

An L1-PROTAC compound can be represented by the following formula:

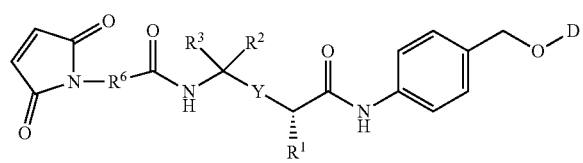

wherein, $R^6$ is $C_1$-$C_{10}$alkylene, and $R^1$, $R^2$ and $R^3$ are as described elsewhere herein, and D is a PROTAC moiety An L1-PROTAC compound can be represented by the following formula:

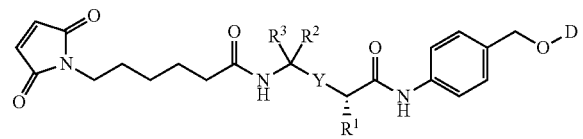

wherein $R^1$, $R^2$ and $R^3$ are as described elsewhere herein, and D is a PROTAC moiety.

In any of the above L-PROTAC compounds, Str can have the following formula:

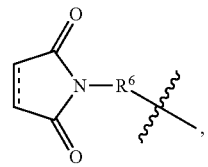

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl aryl, arylalkyl, heteroarylalkyl and heteroaryl; each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

In certain L-PROTAC compounds, $R^6$ is $C_1$-$C_{10}$alkylene, Sp is —Ar—$R^b$—, wherein Ar is aryl $R^b$ is ($C_1$-$C_6$alkylene)O—; or $R_6$ is —$(CH_2)_q$ is 1-10;

In any of the above L-PROTAC compounds, Str can have the following formula:

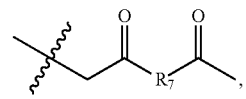

wherein ⁞ indicates a moiety capable of conjugating to an antibody, $R^7$ is selected from $C_1$-$C_{10}$alkylene, $C_1$-$C_{10}$alkylene-O, N($R^c$)—($C_2$-$C_6$ alkylene)-N($R^c$) and N($R^c$)—($C_2$-$C_6$alkylene); where each $R^c$ is independently H or $C_1$-$C_6$ alkyl;
Sp is —Ar—$R^b$—, wherein Ar is aryl or heteroaryl, $R^b$ is ($C_1$-$C_{10}$ alkylene)O—; or wherein $R^6$ is $C_1$-$C_{10}$ alkylene, Sp is —Ar—$R^b$—, wherein Ar is aryl $R^b$ is ($C_1$-$C_6$ alkylene)O—.

An L1-PROTAC can have the following formulae, wherein in each instance, D is a PROTAC moiety:

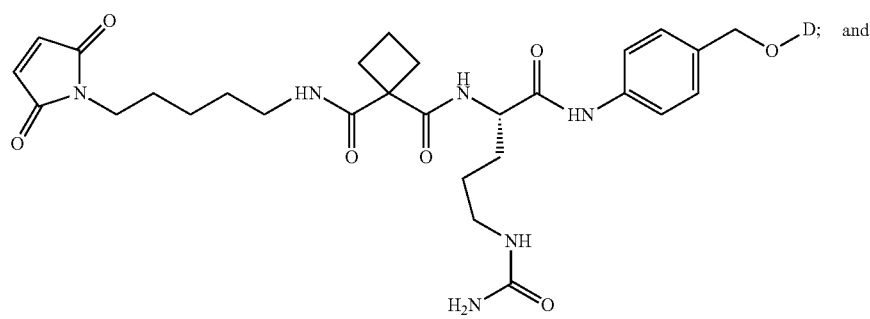

-continued

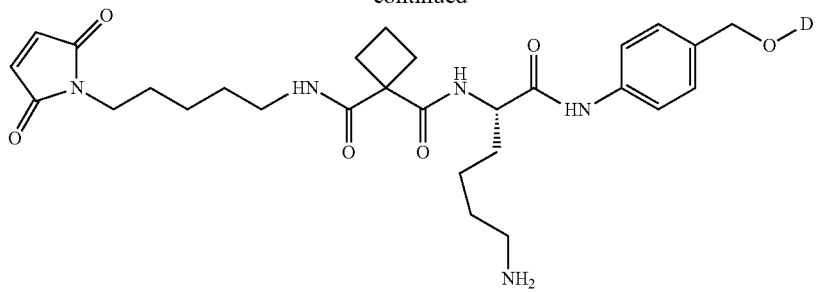

Referring now to the PB group of the PROTAC, in particular embodiments, PB is as described elsewhere herein, or is selected from the group consisting of Heat Shock Protein 90 (HSP90) inhibitors, Kinase and Phosphatase inhibitors, MDM2 inhibitors, HDAC inhibitors, Human Lysine Methyltransferase Inhibitors, Angiogenesis inhibitors, Immunosuppressive compounds, as well as compounds that target: Human BET Bromodomain-containing proteins, the aryl hydrocarbon receptor (AHR), REF receptor kinase, FKBP, Andrpgen Receptor (AR), Estrogen receptor (ER), Thyroid Hormone Receptor, HIV Protease, HIV Integrase, HCV Protease, Acyl-protein Thioesterase-1 and -2 (APT1 and APT2).

In particular embodiments, E3LB is as described elsewhere herein, including a group that binds XIAP, VHL, cereblon and MDM2.

The subject matter described herein is also directed to methods of preparing a PAC from a L-PROTAC compound, the method comprising contacting an antibody, or variants, mutations, splice variants, indels and fusions thereof, with a L-PROTAC under conditions where the antibody is covalently bound to any available point of attachment on a L1-PROTAC, wherein a PAC is prepared. The subject matter described herein is also directed to methods of preparing a PAC from an Ab-L1 portion, i.e., an antibody, or variants, mutations, splice variants, indels and fusions thereof, covalently attached to a L1, the methods comprising contacting a PROTAC with an Ab-L1 under conditions where the PROTAC is covalently bound to any available point of attachment on the Ab-L1, wherein a PAC is prepared. The methods can further comprise routine isolation and purification of the PACs.

Referring now to a PAC and a L-PROTAC compound, as described herein, these can exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes all such solvates.

The skilled artisan will further appreciate that certain compounds and PACs described herein that exist in crystalline form, including the various solvates thereof, may exhibit polymorphism (i.e. the capacity to occur in different crystalline structures). These different crystalline forms are typically known as "polymorphs." The subject matter disclosed herein includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds and PACs described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formula (I) may exist in tautomeric forms other than that shown in the formula and these are also included within the scope of the subject matter disclosed herein. It is to be understood that the subject matter disclosed herein includes all combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes all combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds and PACs as disclosed herein and pharmaceutically acceptable salts thereof that contain the aforementioned isotopes and/or other isotopes of other atoms are within the scope of the subject matter disclosed herein. Isotopically-labelled compounds are disclosed herein, for example those into which radioactive isotopes such as $^{3}H$, $^{14}$C are incorporated, are useful in drug and/or substrate tissue distribution assays. Tritiated, i.e., $^{3}$H, and carbon-14, i.e., $^{14}$C, isotopes are commonly used for their ease of preparation and detectability. $^{11}$C and $^{18}$F isotopes are useful in PET (positron emission tomography), and $^{125}$I isotopes are useful in SPECT (single photon emission computerized tomography), all useful in brain imaging. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

The subject matter described herein includes the following embodiments:

1. A conjugate having the chemical structure

Ab-(L1-D)$_p$, wherein,
D is a PROTAC having the structure E3LB-L2-PB;
E3LB is an E3 ligase binding group covalently bound to L2;
L2 is a linker covalently bound to E3LB and PB;
PB is a protein binding group covalently bound to L2;
Ab is an antibody covalently bound to L1;
L1 is a linker, covalently bound to Ab and to D;
p has a value from about 1 to about 8.

2. The conjugate of embodiment 1, wherein E3LB is a group that binds an E3 ligase, wherein the E3 ligase is listed in Tables 13-27, e.g., Table 13, Table 14, Table 15, Table 16, Table 17, Table 18, Table 19, Table 20, Table 21, Table 22, Table 23, Table 24, Table 25, Table 26, or Table 27.

3. The conjugate of any above embodiment, wherein E3LB is a group that binds an E3 ligase, wherein the E3 ligase is selected from the group consisting of von Hippel-Lindau (VHL); cereblon; XIAP; E3A; MDM2; Anaphase-promoting complex (APC); UBR5 (EDD1); SOCS/BC-box/eloBC/CUL5/RING; LNXp80; CBX4; CBLL1; HACE1; HECTD1; HECTD2; HECTD3; HECW1; HECW2; HERC1; HERC2; HERC3; HERC4; HUWE1; ITCH; NEDD4; NEDD4L; PPIL2; PRPF19; PIAS1; PIAS2; PIAS3; PIAS4; RANBP2; RNF4; RBX1; SMURF1; SMURF2; STUB1; TOPORS; TRIP12; UBE3A; UBE3B; UBE3C; UBE4A; UBE4B; UBOX5; UBR5; WWP1; WWP2; Parkin; A20/TNFAIP3; AMFR/gp78; ARA54; beta-TrCP1/BTRC; BRCA1; CBL; CHIP/STUB1; E6; E6AP/UBE3A; F-box protein 15/FBXO15; FBXW7/Cdc4; GRAIL/RNF128; HOIP/RNF31; cIAP-1/HIAP-2; cIAP-2/HIAP-1; cIAP (pan); ITCH/AIP4; KAP1; MARCH8; MDM2/HDM2; Mind Bomb 1/MIB1; Mind Bomb 2/MIB2; MuRF1/TRIM63; NDFIP1; NEDD4; NleL; Parkin; RNF2; RNF4; RNF8; RNF168; RNF43; SART1; Skp2; SMURF2; TRAF-1; TRAF-2; TRAF-3; TRAF-4; TRAF-5; TRAF-6; TRIM5; TRIM21; TRIM32; UBR5; and ZNRF3.

4. The conjugate of any above embodiment, wherein E3LB is a group that binds an E3 ligase selected from the group consisting of XIAP, VHL, cereblon and MDM2.

5. The conjugate of any above embodiment, wherein E3LB is selected from the group consisting of a compound that binds VHL, a hydroxyproline compound that binds VHL, a compound that binds MDM2, a compound that binds cereblon, a tetrahhydro-benzodiazepinone, a nutlin, and small molecular binding compounds as described herein.

6. The conjugate of any above embodiment, wherein E3LB is a XIAP inhibitor that is a tetrahydro-benzodiazepinone having the formula:

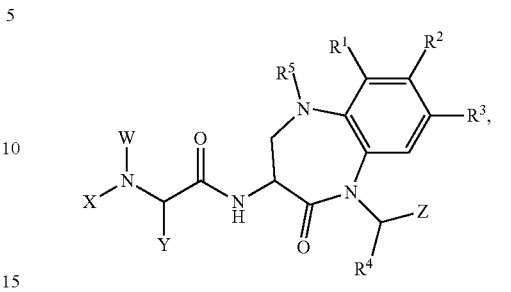

wherein, R1, R2, R3, R4 and R5 are as described in WO/2015/071393, and including all compounds therein.

7. The conjugate of any above embodiment, wherein PB is a group that binds FoxO1, HDAC, DP-1, E2F, ABL, AMPK, BRK, BRSK I, BRSK2, BTK, CAMKK1, CAMKK alpha, CAMKK beta, Rb, Suv39HI, SCF, p19INK4D, GSK-3, pi 8 INK4, myc, cyclin E, CDK2, CDK9, CDG4/6, Cycline D, p16 INK4A, cdc25A, BMI1, SCF, Akt, CHK1/2, C 1 delta, CK1 gamma, C 2, CLK2, CSK, DDR2, DYRK1A/2/3, EF2K, EPH-A2/A4/B1/B2/B3/B4, EIF2A 3, Smad2, Smad3, Smad4, Smad7, p53, p21 Cip1, PAX, Fyn, CAS, C3G, SOS, Ta1, Raptor, RACK-1, CRK, Rap1, Rac, KRas, NRas, HRas, GRB2, FAK, PI3K, spred, Spry, mTOR, MPK, LKB1, PAK 1/2/4/5/6, PDGFRA, PYK2, Src, SRPK1, PLC, PKC, PKA, PKB alpha/beta, PKC alpha/gamma/zeta, PKD, PLK1, PRAK, PRK2, RIPK2, WAVE-2, TSC2, DAPK1, BAD, IMP, C-TAK1, TAK1, TAO1, TBK1, TESK1, TGFBR1, TIE2, TLK1, TrkA, TSSK1, TTBK1/2, TTK, Tpl2/cot1, MEK1, MEK2, PLDL Erk1, Erk2, Erk5, Erk8, p90RSK, PEA-15, SRF, p27 KIP1, TIF 1a, HMGN1, ER81, MKP-3, c-Fos, FGF-R1, GCK, GSK3 beta, HER4, HIPK1/2/3/, IGF-1R, cdc25, UBF, LAMTOR2, Stat1, StaO, CREB, JAK, Src, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, TAK1, JNK1/2/3, Lck, A-Raf, B-Raf, C-Raf, MOS, MLK1/3, MN 1/2, MSK1, MST2/3/4, MPSK1, MEKK1, ME K4, MEL, ASK1, MINK1, MKK 1/2/3/4/6/7, NE 2a/6/7, NUAK1, OSR1, SAP, STK33, Syk, Lyn, PDK1, PHK, PIM 1/2/3, Ataxin-1, mTORC1, MDM2, p21 Waf1, Cyclin Dl, Lamln A, Tpl2, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPK1b, MAPKAP-K2 K3, p38 alpha/beta/delta/gamma MAPK, Aurora A, Aurora B, Aurora C, MCAK, Clip, MAPKAPK, FAK, MARK 1/2/3/4, Muc1, SHC, CXCR4, Gap-1, Myc, beta-catenin/TCF, Cbl, BRM, Mcl1, BRD2, BRD3, BRD4, AR, RAS, ErbB3, EGFR, IRE1, HPK1, RIPK2, and Era, including all variants, mutations, splice variants, indels and fusions thereof.

8. The conjugate of any above embodiment, wherein PB is selected from the group consisting of Heat Shock Protein 90 (HSP90) inhibitors, Kinase and Phosphatase inhibitors, MDM2 inhibitors, HDAC inhibitors, Human Lysine Methyltransferase Inhibitors, Angiogenesis inhibitors, Immunosuppressive compounds, and compounds that target: Human BET Bromodomain-containing proteins, the aryl hydrocarbon receptor (AHR), REF receptor kinase, FKBP, Androgen Receptor (AR), Estrogen receptor (ER), Thyroid Hormone Receptor, HIV Protease, HIV Integrase, HCV Protease, and Acyl-protein Thioesterase-1 and -2 (APT1 and APT2).

9. The conjugate of any above embodiment, wherein PB is a compound that targets Estrogen Receptor alpha (ERα).

10. The conjugate of any above embodiment, wherein the Ab is selected from Tables 4-12, e.g., Table 4, Table 5, Table 6, Table 7, Table 8, Table 9, Table 10, Table 11, or Table 12.

11. The conjugate of any above embodiment, wherein the Ab is a cysteine engineered antibody or variants thereof.

12. The conjugate of any above embodiment, wherein Ab binds to one or more of polypeptides selected from the group consisting of DLL3; EDAR; CLL1; BMPRIB; E16; STEAP1; 0772P; MPF; NaPi2b; Sema 5b; PSCA hlg; ETBR; MSG783; STEAP2; TrpM4; CRIPTO; CD21; CD79b; FcRH2; B7-H4; HER2; NCA; MDP; IL20Rα; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM18; GPR172A; MUC16 and CD33.

13. The conjugate of any above embodiment, wherein Ab binds to one or more of polypeptides selected from the group consisting of CLL1; STEAP1; NaPi2b; STEAP2; TrpM4; CRIPTO; CD21; CD79b; FcRH2; B7-H4; HER2; CD22; CD79a; CD72; LY64; Ly6E; MUC 16; and CD33.

14. The conjugate of any above embodiment, wherein Ab is an antibody that binds to one or more polypeptides selected from the group consisting of B7-H4, Her2, CLL1, CD33, CD22 and NaPi2b.

15. The conjugate of any above embodiment, wherein the antibody binds to HER2 or B7-H4.

16. The conjugate of any above embodiment, wherein the antibody binds to Her2.

17. The conjugate of any above embodiment, wherein L1 is a peptidomimetic linker.

18. The conjugate of any above embodiment, wherein L1 is a peptidomimetic linker represented by the following formula:

-Str-(PM)-Spwherein,
Str is a stretcher unit covalently attached to Ab;
Sp is a bond or spacer unit covalently attached to a PROTAC moiety;
PM is a non-peptide chemical moiety selected from the group consisting of:

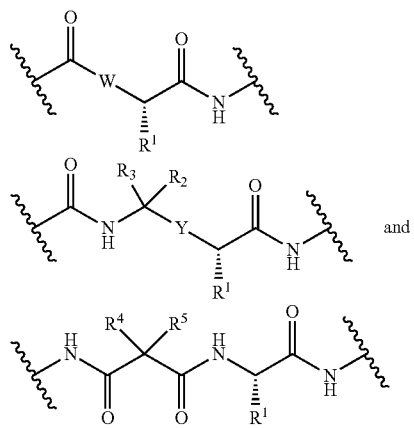

W is —NH-heterocycloalkyl- or heterocycloalkyl;
Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;
each $R^1$ is independently $C_1$-$C_{10}$alkyl, $C_1$-$C_{10}$alkenyl, ($C_1$-$C_{10}$alkyl)NHC(NH)$NH_2$ or ($C_1$-$C_{10}$alkyl)NHC(O)$NH_2$;
$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and
$R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ together may form a $C_3$-$C_7$cycloalkyl ring.

19. The conjugate of any above embodiment, wherein Y is heteroaryl; $R^4$ and $R^5$ together form a cyclobutyl ring.

20. The conjugate of any above embodiment, wherein Y is a moiety selected from the group consisting of

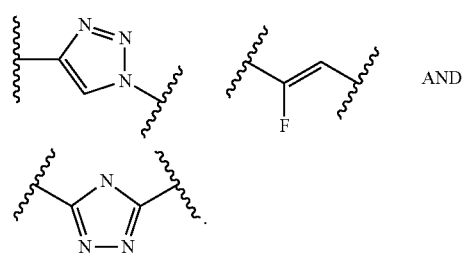

AND

21. The conjugate of any above embodiment, wherein Str is a chemical moiety represented by the following formula:

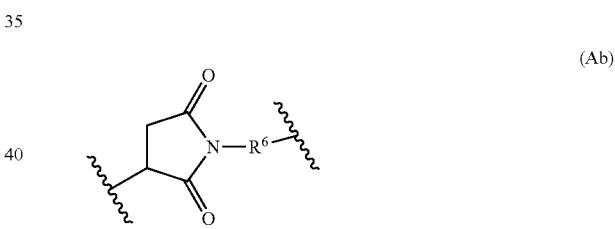

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, heteroarylalkyl, aryl arylalkyl, heteroarylalkyl and heteroaryl each $R^a$ is independently H or $C_1$-$C_6$alkyl;
Sp is —$C_1$-$C_6$alkylene-C(O)NH— or —Ar—$R^b$—, wherein Ar is aryl or heteroaryl, $R^b$ is ($C_1$-$C_{10}$alkylene)O—.

22. The conjugate of any above embodiment, wherein Str has the formula:

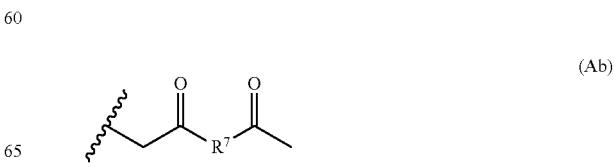

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) and N($R^c$)—($C_2$-$C_6$alkylene); where each $R^c$ is independently H or $C_1$-$C_6$ alkyl;

Sp is —$C_1$-$C_6$alkylene-C(O)NH— or —Ar—$R^b$—, wherein Ar is aryl or heteroaryl, $R^b$ is ($C_1$-$C_{10}$alkylene)O—.

23. The conjugate of any above embodiment, wherein L1 has the following formula

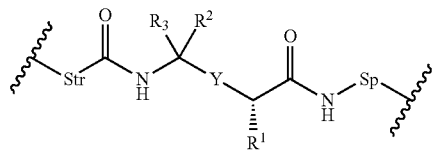

$R^1$ is $C_1$-$C_6$alkyl, $C_1$-$C_6$alkenyl, ($C_1$-$C_6$alkyl)NHC(NH)NH$_2$ or ($C_1$-$C_6$alkyl)NHC(O)NH$_2$;

$R^3$ and $R^2$ are each independently H, $C_1$-$C_{10}$alkyl; and Str and Sp are as defined herein.

24. The conjugate of any above embodiment, wherein L1 has the following formula

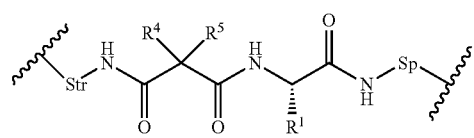

$R^1$ is $C_1$-$C_6$alkyl, ($C_1$-$C_6$alkyl)NHC(NH)NH$_2$ or ($C_1$-$C_6$alkyl)NHC(O)NH$_2$; Str and Sp are as defined herein; and $R^4$ and $R^5$ together form a $C_3$-$C_7$cycloalkyl ring.

25. The conjugate of any above embodiment, wherein L1 has the following formula

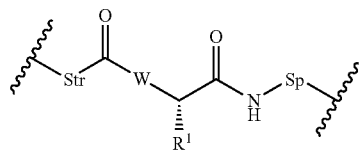

Str and Sp are as defined herein; and $R^1$ is $C_1$-$C_6$alkyl, ($C_1$-$C_6$alkyl)NHC(NH)NH$_2$ or ($C_1$-$C_6$alkyl)NHC(O)NH$_2$.

26. The conjugate of any above embodiment, having the formula:

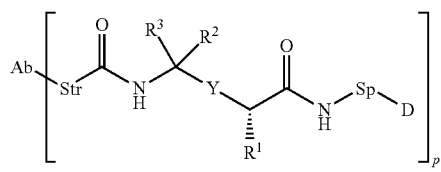

wherein
Str is a chemical moiety represented by the following formula:

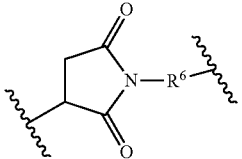

$R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, heteroarylalkyl, aryl, arylalkyl, heteroarylalkyl and heteroaryl each $R^a$ is independently H or $C_1$-$C_6$alkyl;
Ab and Sp are as defined herein; and
p is 1, 2, 3 or 4.

27. The conjugate of any above embodiment, having the formula:

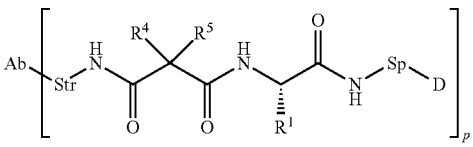

wherein
Str is a chemical moiety represented by the following formula:

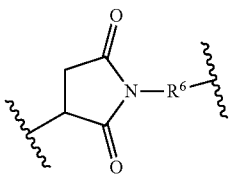

$R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl;
$R^1$, $R^4$, $R^5$, Ab, D and Sp are as defined herein; and
p is 1, 2, 3 or 4.

28. The conjugate of any above embodiment, wherein Y is heteroaryl, aryl or alkenyl; $R^6$ is $C_1$-$C_{10}$alkylene.

29. The conjugate of any above embodiment, wherein Y is

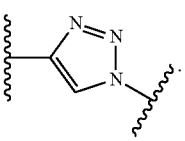 [SMILES: *c1cn(*)nn1]

30. The conjugate of any above embodiment, wherein Y is

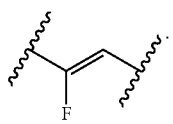 [SMILES: */C=C(/*)F]

31. The conjugate of any above embodiment, wherein Y is

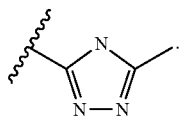

32. The conjugate of any above embodiment, wherein Str is a chemical moiety represented by the following formula:

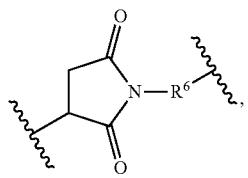
(Ab)

$R^6$ is $C_1$-$C_6$alkylene;
Sp is —$C_1$-$C_6$alkylene-C(O)NH— or —Ar—$R^b$—, where Ar is aryl, $R^b$ is ($C_1$-$C_3$alkylene)O—.

33. The conjugate of any above embodiment, having the formula:

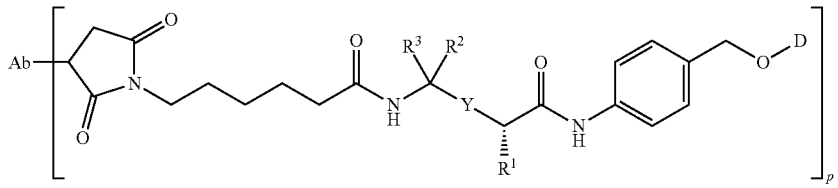

wherein
Ab, D, $R^2$ and $R^3$ are as defined herein;
$R^1$ is $C_1$-$C_6$alkyl-NH$_2$, ($C_1$-$C_6$alkyl)NHC(NH)NH$_2$ or ($C_1$-$C_6$alkyl)NHC(O)NH$_2$; and
p is 1, 2, 3 or 4.

34. The conjugate of any above embodiment, having the formula:

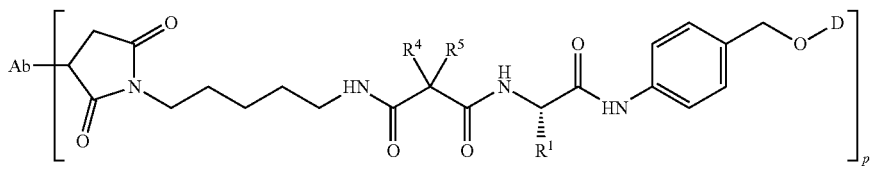

wherein
Ab and D are as defined herein;
p is 1, 2, 3 or 4;
$R^1$ is $C_1$-$C_6$alkyl-NH$_2$, ($C_1$-$C_6$alkyl)NHC(NH)NH$_2$ or ($C_1$-$C_6$alkyl)NHC(O)NH$_2$;

$R^4$ and $R^5$ are each independently $C_1$-$C_6$alkyl, wherein the alkyl are unsubstituted, or $R^4$ and $R^5$ together with the carbon to which each is attached can form a $C_3$-$C_7$cycloalkyl ring, such as a cyclobutyl.

35. The conjugate of any above embodiment, wherein L1 has the following formula:

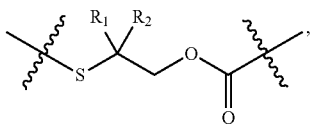

wherein, $R^1$ and $R^2$ are independently selected from H and $C_1$-$C_6$ alkyl, or $R^1$ and $R^2$ form a 3, 4, 5, or 6-membered cycloalkyl or heterocyclyl group.

36. The conjugate of any above embodiment selected from the group consisting of PAC1, PAC2, PAC3, PAC4, and PAC5.

37. The conjugate of any above embodiment, wherein the ratio of PROTAC per Antibody ("PAR") is from about 1.5 to about 3.

38. The conjugate of any above embodiment, wherein the ratio of PROTAC per Antibody ("PAR") is about 2.

39. A method of treating a disease in a human in need thereof, comprising administering to the human an effective amount of a conjugate of any above embodiment.

40. A pharmaceutical composition comprising a conjugate of any above embodiment and a pharmaceutically acceptable excipient.

41. A method of treating a disease in a human in need thereof, comprising administering to said human an effective amount of a pharmaceutical composition of embodiment 40.

42. A method of treating a disease with a conjugate of any above embodiment, wherein the disease is a hyperproliferative disorder, including, benign or malignant solid tumors and hematological disorders, disorders involving neuronal, glial, astrocytal, hypothalamic, glandular, macrophagal, epithelial, stromal, blastocoelic, inflammatory, angiogenic, immunologic, and autoimmune conditions.

43. A method of treating a disease with a conjugate of any above embodiment, wherein the disease is cancer.

44. A method of treating a disease with a conjugate of any above embodiment, wherein the cancer is selected from the group consisting of a carcinoma, lymphoma, blastoma, sarcoma, leukemia, lymphoid malignancies, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, and head and neck cancer.

45. The method of embodiment 43, wherein the cancer is a HER2-positive cancer.

46. The method of embodiment 45, wherein the HER2-positive cancer is breast cancer or gastric cancer.

47. A method of treating a disease with a conjugate of any above embodiment, wherein the disease is an autoimmune disease.

48. The method of embodiment 47, wherein said autoimmune disease is selected from the group consisting of rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)).

49. The method of embodiment 47, wherein said autoimmune disease is selected from the group consisiting of rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

50. Use of a conjugate of any above embodiment in the manufacture of a medicament for the treatment of cancer in a mammal.

51. A method of preparing a PAC, said method comprising contacting a Linker L1-PROTAC with an antibody.

IV. Synthesis Routes

PACs and compounds described herein can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9): 1910-16, (1985); Helvetica Chimica Acta, 41:1052-60, (1958); Arzneimittel-Forschung, 40(12):1328-31, (1990). Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing the PACs and groups as described herein and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof. In preparing PACs and compounds, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz or CBZ) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The General Procedures and Examples provide exemplary methods for preparing PACs and compounds described herein. Those skilled in the art will appreciate that other synthetic routes may be used to synthesize the PACs and compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Generally, a PAC may be prepared by connecting a PROTAC with a L1 linker reagent according to the procedures of WO 2013/055987; WO 2015/023355; WO 2010/009124; WO 2015/095227, and conjugating it with any of the antibodies or variants, mutations, splice variants, indels and fusions thereof, including cysteine engineered antibodies, described herein. Alternatively, a PAC may be prepared by first connecting an antibody or variant, mutation, splice variant, indel and fusion thereof, including a cysteine engineered antibody, described herein with a L1 linker reagent, and conjugating it with any PROTAC.

The following synthetic routes describe exemplary methods of preparing PACs and components thereof. Other synthetic routes for preparing PACs and components thereof are disclosed elsewhere herein.

1. Linker L1

With respect to Linker L1, Schemes 1-4 depict synthesis routes to exemplary linkers L1 for disulfide attachment to antibody Ab. The Ab is connected to L1 through a disulfide bond and the PROTAC is connected to L1 through any available attachment on the PROTAC.

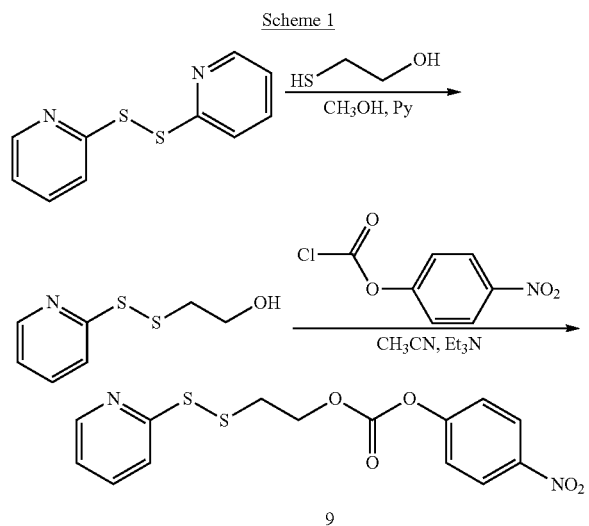

Scheme 1

Referring to Scheme 1, 1,2-Di(pyridin-2-yl)disulfane and 2-mercaptoethanol were reacted in pyridine and methanol at room temperature to give 2-(pyridin-2-yldisulfanyl)ethanol. Acylation with 4-nitrophenyl carbonochloridate in triethylamine and acetonitrile gave 4-nitrophenyl 2-(pyridin-2-yldisulfanyl)ethyl carbonate 9.

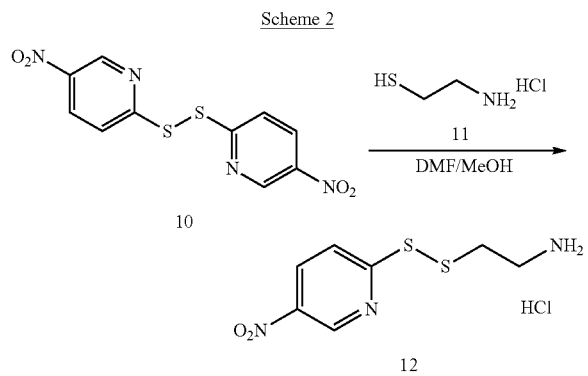

Scheme 2

Referring to Scheme 2, to a mixture of 1,2-bis(5-nitropyridin-2-yl)disulfane 10 (1.0 g, 3.22 mmol) in anhydrous DMF/MeOH (25 mL/25 mL) was added HOAc (0.1 mL), followed by 2-aminoethanethiol hydrochloride 11 (183 mg, 1.61 mmol). After the reaction mixture was stirred at r.t. overnight, it was concentrated under vacuum to remove the solvent, and the residue was washed with DCM (30 mL×4) to afford 2-((5-nitropyridin-2-yl)disulfanyl)ethanamine hydrochloride 12 as pale yellow solid (300 mg, 69.6%). $^1$H NMR (400 MHz, DMSO-$d_6$) δ 9.28 (d, J=2.4 Hz, 1H), 8.56 (dd, J=8.8, 2.4 Hz, 1H), 8.24 (s, 4H), 8.03 (d, J=8.8 Hz, 1H), 3.15-3.13 (m, 2H), 3.08-3.06 (m, 2H).

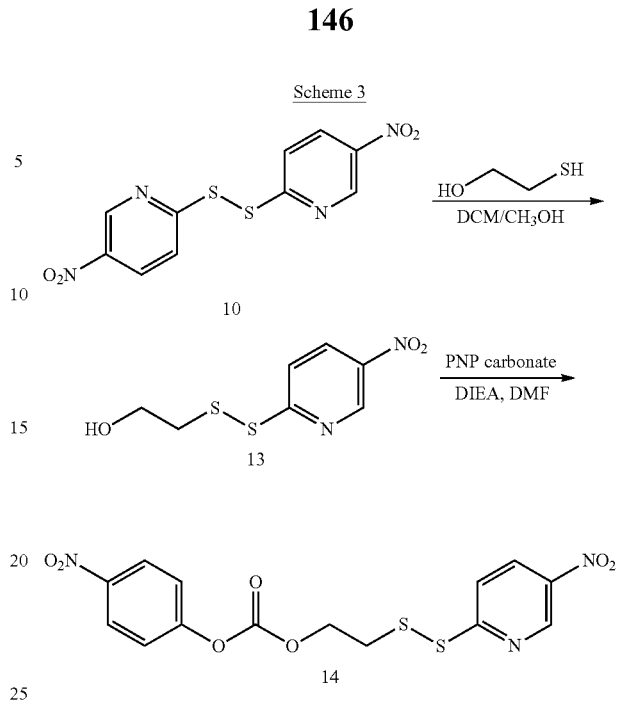

Scheme 3

Referring to Scheme 3, a solution of 1,2-bis(5-nitropyridin-2-yl)disulfane 10 (9.6 g, 30.97 mmol) and 2-mercaptoethanol (1.21 g, 15.49 mmol) in anhydrous DCM/CH$_3$OH (250 mL/250 mL) was stirred at r.t. under N$_2$ for 24 h. After the mixture was concentrated under vacuum, and the residue was diluted with DCM (300 mL). MnO$_2$ (10 g) was added and the mixture was stirred at r.t. for another 0.5 h. The mixture was purified by column chromatography on silica gel (DCM/MeOH=100/1 to 100/1) to afford 2-((5-nitropyridin-2-yl)disulfanyl)ethanol 13 (2.2 g, 61.1%) as brown oil. $^1$H NMR (400 MHz, CDCl$_3$) δ 9.33 (d, J=2.8 Hz, 1H), 8.38-8.35 (dd, J=9.2, 2.8 Hz, 1H), 7.67 (d, J=9.2 Hz, 1H), 4.10 (t, J=7.2 Hz, 1H), 3.81-3.76 (q, 2H), 3.01 (t, J=5.2 Hz, 2H).

To a solution of 13 (500 mg, 2.15 mmol) in anhydrous DMF (10 mL) was added DIEA (834 mg, 6.45 mmol), followed by PNP carbonate (bis(4-nitrophenyl) carbonate, 1.31 g, 4.31 mmol). The reaction solution was stirred at r.t for 4 h and the mixture was purified by prep-HPLC (FA) to afford 4-nitrophenyl 2-((5-nitropyridin-2-yl)disulfanyl)ethyl carbonate 14 (270 mg, 33.1%) as light brown oil. $^1$H NMR (400 MHz, CDCl$_3$) δ 9.30 (d, J=2.4 Hz, 1H), 8.43-8.40 (dd, J=8.8, 2.4 Hz, 1H), 8.30-8.28 (m, 2H), 7.87 (d, J=8.8 Hz, 1H), 7.39-7.37 (m, 2H), 4.56 (t, J=6.4 Hz, 2H), 3.21 (t, J=6.4 Hz, 2H).

Scheme 4

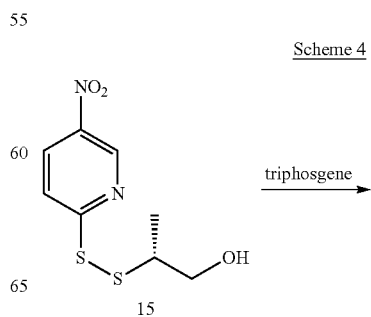

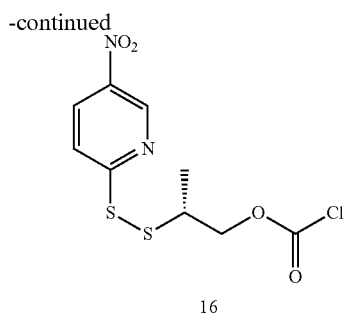

16

Referring to Scheme 4, sulfuryl chloride (2.35 mL of a 1.0M solution in DCM, 2.35 mmol) was added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and was allowed to warm to room temperature then stirred for 2 hours after which time the solvent was removed by evaporation in vacuo to provide a yellow solid. The solid was re-dissolved in DCM (15 mL) and treated drop-wise with a solution of (R)-2-mercaptopropan-1-ol (213 mg, 2.31 mmol) in dry DCM (7.5 mL) at 0° C. under an argon atmosphere. The reaction mixture was allowed to warm to room temperature and stirred for 20 hours at which point analysis by LC/MS revealed substantial product formation at retention time 1.41 minutes (ES+) m/z 247 ([M+H]+, ~100% relative intensity). The precipitate was removed by filtration and the filtrate evaporated in vacuo to give an orange solid which was treated with $H_2O$ (20 mL) and basified with ammonium hydroxide solution. The mixture was extracted with DCM (3×25 mL) and the combined extracts washed with $H_2O$ (20 mL), brine (20 mL), dried ($MgSO_4$), filtered and evaporated in vacuo to give the crude product. Purification by flash chromatography (gradient elution in 1% increments: 100% DCM to 98:2 v/v DCM/MeOH) gave (R)-2-((5-nitropyridin-2-yl)disulfanyl)propan-1-ol 15 as an oil (111 mg, 21% yield).

To a solution of triphosgene, $Cl_3COCOOCCl_3$, Sigma Aldrich, CAS Reg. No. 32315-10-9 (241 mg, 0.812 mmol) in DCM (10 mL) was added a solution of (R)-2-((5-nitropyridin-2-yl)disulfanyl)propan-1-ol 15 (500 mg, 2.03 mmol) and pyridine (153 mg, 1.93 mmol) in DCM (10 mL) dropwise at 20° C. After the reaction mixture was stirred at 20° C. for 30 min, it was concentrated and (R)-2-((5-nitropyridin-2-yl)disulfanyl)propyl carbonochloridate 16 can be used directly without further purification to covalently link through the carbonochloridate group any available group on the PROTAC.

2. Cysteine Engineered Antibodies

With regard to cysteine engineered antibodies for conjugation by reduction and reoxidation, they can be prepared generally as follows. Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (THIOMAB™ antibodies) expressed in CHO cells bear cysteine adducts (cystines) or are glutathionylated on the engineered cysteines due to cell culture conditions. As is, THIOMAB™ antibodies purified from CHO cells cannot be conjugated to Cys-reactive linker L-PROTAC intermediates. Cysteine engineered antibodies may be made reactive for conjugation with linker-PROTAC intermediates described herein, by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.) followed by re-formation of the inter-chain disulfide bonds (re-oxidation) with a mild oxidant such as dehydroascorbic acid. Full length, cysteine engineered monoclonal antibodies (THIOMAB™ antibodies) expressed in CHO cells (Gomez et al (2010) Biotechnology and Bioeng. 105(4):748-760; Gomez et al (2010) Biotechnol. Prog. 26:1438-1445) were reduced, for example, with about a 50 fold excess of DTT overnight in 50 mM Tris, pH 8.0 with 2 mM EDTA at room temperature, which removes Cys and glutathione adducts as well as reduces interchain disulfide bonds in the antibody. Removal of the adducts was monitored by reverse-phase LCMS using a PLRP-S column. The reduced THIOMAB™ antibody was diluted and acidified by addition to at least four volumes of 10 mM sodium succinate, pH 5 buffer.

Alternatively, the antibody was diluted and acidified by adding to at least four volumes of 10 mM succinate, pH 5 and titration with 10% acetic acid until pH was approximately five. The pH-lowered and diluted THIOMAB™ antibody was subsequently loaded onto a HiTrap S cation exchange column, washed with several column volumes of 10 mM sodium acetate, pH 5 and eluted with 50 mM Tris, pH 8.0, 150 mM sodium chloride. Disulfide bonds were reestablished between cysteine residues present in the parent Mab by carrying out reoxidation. The eluted reduced THIOMAB™ antibody described above is treated with 15× dehydroascorbic acid (DHAA) for about 3 hours or, alternatively, with 200 nM to 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. Reoxidation was monitored by reverse-phase LCMS using a PLRP-S column. The reoxidized THIOMAB™ antibody was diluted with succinate buffer as described above to reach pH approximately 5 and purification on an S column was carried out as described above with the exception that elution was performed with a gradient of 10 mM succinate, pH 5, 300 mM sodium chloride (buffer B) in 10 mM succinate, pH 5 (buffer A). To the eluted THIOMAB™ antibody, EDTA was added to a final concentration of 2 mM and concentrated, if necessary, to reach a final concentration of more than 5 mg/mL. The resulting THIOMAB™ antibody, ready for conjugation, was stored at −20° C. or −80° C. in aliquots. Liquid chromatography/Mass Spectrometric Analysis was performed on a 6200 series TOF or QTOF Agilent LC/MS. Samples were chromatographed on a PRLP-S®, 1000 A, microbore column (50 mm×2.1 mm, Polymer Laboratories, Shropshire, UK) heated to 80° C. A linear gradient from 30-40% B (solvent A: 0.05% TFA in water, solvent B: 0.04% TFA in acetonitrile) was used and the eluent was directly ionized using the electrospray source. Data were collected and deconvoluted by the MassHunter software (Agilent). Prior to LC/MS analysis, antibodies or conjugates (50 micrograms) were treated with PNGase F (2 units/ml; PROzyme, San Leandro, Calif.) for 2 hours at 37° C. to remove N-linked carbohydrates.

Alternatively, antibodies or conjugates were partially digested with LysC (0.25 μg per 50 pig (microgram) antibody or conjugate) for 15 minutes at 37° C. to give a Fab and Fc fragment for analysis by LCMS. Peaks in the deconvoluted LCMS spectra were assigned and quantitated. PROTAC-to-antibody ratios (PAR) were calculated by calculating the ratio of intensities of the peak or peaks corresponding to PROTAC-conjugated antibody relative to all peaks observed.

3. Conjugation of Linker L-PROTAC Group to Antibodies

In one method of conjugating Linker L-PROTAC compounds to antibodies, after the reduction and reoxidation procedures above, the cysteine-engineered antibody (THIO-MAB™ antibody), in 10 mM succinate, pH 5, 150 mM NaCl, 2 mM EDTA, is pH-adjusted to pH 7.5-8.5 with 1M Tris. An excess, from about 3 molar to 20 equivalents of a linker-PROTAC intermediate with a thiol-reactive group (e.g., maleimide or 4-nitropyridy disulfide), is dissolved in DMF, DMA or propylene glycol and added to the reduced, reoxidized, and pH-adjusted antibody. The reaction is incubated at room temperature or 37 C and monitored until completion (1 to about 24 hours), as determined by LC-MS analysis of the reaction mixture. When the reaction is complete, the conjugate is purified by one or any combination of several methods, the goal being to remove remaining unreacted linker-PROTAC intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used. The THIOMAB™ antibody PROTAC conjugates were formulated into 20 mM His/acetate, pH 5, with 240 mM sucrose using either gel filtration or dialysis. The purified conjugate is concentrated by centrifugal ultrafiltration and filtered through a 0.2-µm filter under sterile conditions and frozen for storage. The PACs were characterized by BCA assay to determine protein concentration, analytical SEC (size-exclusion chromatography) for aggregation analysis and LC-MS after treatment with Lysine C endopeptidase (LysC) to calculate PAR.

Size exclusion chromatography is performed on conjugates using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis may be performed on PAC using an Agilent QTOF 6520 ESI instrument. As an example, the PAR is treated with 1:500 w/w Endoproteinase Lys C (Promega) in Tris, pH 7.5, for 30 min at 37° C. The resulting cleavage fragments are loaded onto a 1000A (Angstrom), 8 µm (micron) PLRP-S (highly cross-linked polystyrene) column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

V. Formulations

Pharmaceutical formulations of therapeutic PROTAC-antibody-conjugates (PACs) as described herein can be prepared for parenteral administration, e.g., bolus, intravenous, intratumor injection with a pharmaceutically acceptable parenteral vehicle and in a unit dosage injectable form. A PAC having the desired degree of purity is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

PACs can be formulated in accordance with standard pharmaceutical practice as a pharmaceutical composition. According to this aspect, there is provided a pharmaceutical composition comprising a PAC in association with one or more pharmaceutically acceptable excipients.

A typical formulation is prepared by mixing PACs with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the PAC is being applied. Solvents are generally selected based on solvents recognized by persons skilled in the art as safe (GRAS) to be administered to a mammal.

In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the PAC or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The PAC formulations can be sterile. In particular, formulations to be used for in vivo administration must be sterile. Such sterilization is readily accomplished by filtration through sterile filtration membranes.

The PAC ordinarily can be stored as a solid composition, a lyophilized formulation or as an aqueous solution.

The pharmaceutical compositions comprising a PAC can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The PAC can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of PAC that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 ml/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

VI. Indications and Methods of Treatment

It is contemplated that the PROTAC-antibody conjugates (PAC) disclosed herein may be used to treat various diseases or disorders. Exemplary hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the PAC may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

In certain embodiments, a PAC comprising an anti-NaPi2b antibody, such as those described above, is used in a method of treating solid tumor, e.g., ovarian.

In another embodiment, a PAC an anti-CD33 antibody, such as those described herein, is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See: U.S. Pat. No. 8,226,945; Li et al (2013) *Mol. Cancer. Ther.* 12(7): 1255-1265; Poison et al (2010) *Leukemia* 24:1566-1573; Poison et al (2011) *Expert Opin. Investig. Drugs* 20(1):75-85.

In another embodiment, a PAC comprising an anti-MUC 16 antibody, such as those described herein, is used in a method of treating ovarian, breast and pancreatic cancers. The cancer may be associated with the expression or activity of a MUC 16/CA125/0772P polypeptide. See: WO 2007/001851; U.S. Pat. Nos. 7,989,595; 8,449,883; 7,723,485; Chen et al (2007) Cancer Res. 67(10): 4924-4932; Junutula, et al., (2008) *Nature Biotech.,* 26(8):925-932.

In certain embodiments, a PAC comprising an anti-HER2 antibody, such as those described above, is used in a method of treating cancer, e.g., breast or gastric cancer, more specifically HER2+ breast or gastric cancer, wherein the method comprises administering such PAC to a patient in need of such treatment. In one such embodiment, the PAC comprises the anti-HER2 antibody trastuzumab or pertuzumab.

A PAC may be administered by any route appropriate to the condition to be treated. The PAC will typically be administered parenterally, i.e. infusion, subcutaneous, intramuscular, intravenous, intradermal, intrathecal and epidural.

A PAC can be used either alone or in combination with other agents in a therapy. For instance, a PAC may be co-administered with at least one additional therapeutic agent. Such combination therapies noted above encompass combined administration (where two or more therapeutic agents are included in the same or separate formulations), and separate administration, in which case, administration of the PAC can occur prior to, simultaneously, and/or following, administration of the additional therapeutic agent and/or adjuvant. A PAC can also be used in combination with radiation therapy.

A PAC (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of disease, the appropriate dosage of a PAC (when used alone or in combination with one or more other additional therapeutic agents) will depend on the type of disease to be treated, the type of PAC, the severity and course of the disease, whether the PAC is administered for preventive or therapeutic purposes, previous therapy, the patient's clinical history and response to the PAC, and the discretion of the attending physician. The PAC is suitably administered to the patient at one time or over a series of treatments. Depending on the type and severity of the disease, about 1 µg/kg to 15 mg/kg (e.g. 0.1 mg/kg-10 mg/kg) of a PAC can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of a PAC would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses). An initial higher loading dose, followed by one or more lower doses may be administered. However, other dosage regimens may be useful. The progress of this therapy is easily monitored by conventional techniques and assays.

VII. Articles of Manufacture

In another aspect, described herein are articles of manufacture, for example, a "kit", containing materials useful for the treatment of the diseases and disorders described above is provided. The kit comprises a container comprising a PAC. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In one embodiment, the vial is a single-use vial, e.g. a 20-cc single-use vial with a stopper. The container may be formed from a variety of materials such as glass or plastic. The container may hold a PAC or a formulation thereof which is effective for treating the condition and may have a sterile access port (for example, the container may be an intravenous solution bag or a vial having a stopper pierceable by a hypodermic injection needle).

At least one active agent in the composition is a PAC. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a PAC can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the PAC and, if present, the second pharmaceutical formulation. For example, if the kit comprises a first composition comprising a PAC, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a PAC, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a PAC contained therein; and optionally (b) a second container with a second pharmaceutical formulation contained therein, wherein the second pharmaceutical formulation comprises a second compound with antihyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a PAC and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The following examples are offered by way of illustration and not by way of limitation.

EXAMPLES

Example 1

Syntheses of a PAC

A. Chemical Synthesis of a PROTAC i. Attachment of a Linker (L2) to an E3 Ligase Binding Group (E3LB)

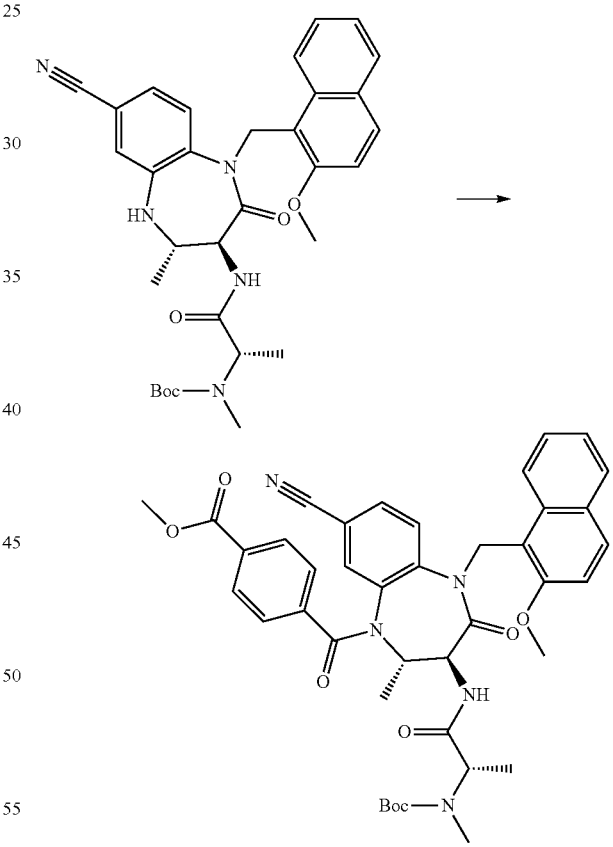

Methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate To a solution of tert-butyl N-[(1S)-1-[[(3 S,4S)-7-cyano-1-[(2-methoxynaphthalen-1-yl)methyl]-4-methyl-2-oxo-2,3,4,5-tetrahydro-1H-1,5-benzodiazepin-3-yl]carbamoyl]

ethyl]-N-methylcarbamate (3.00 g, 5.25 mmol) in 1,2-dichloroethane (50 mL) was added triethylamine (2.6 g, 25.7 mmol) and methyl 4-(carbonochloridoyl)benzoate (3.10 g, 15.61 mmol) under nitrogen. The resulting solution was stirred for 5 h at 80° C. and allowed to cool to room temperature. Water (100 mL) was added. The resulting solution was extracted with 3×100 mL of dichloromethane and the organic layers combined and dried over anhydrous sodium sulfate and concentrated under vacuum. The residue was purified by flash chromatography on silica gel eluting with ethyl acetate/petroleum ether (1:1). This resulted in 3.10 g (81%) of methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate as a brown solid. MS (ESI): [M+H]$^+$=734.4.

4-[[(2S,3S)-3-[(2S)-2-[[(Tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid Aqueous LiOH solution (30 mL, 1 M) was added to a solution of methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate (3.10 g, 4.22 mmol) in tetrahydrofuran (30 mL) at room temperature. The resulting solution was stirred for 5 h at room temperature. Ethyl ether (20 mL) was added. Phases were separated. The aqueous phase was acidified with 1 N HCl solution until pH about 7. The resulting mixture was extracted with 2×80 mL of ethyl acetate and the organic layers were combined and dried over anhydrous sodium sulfate and concentrated under vacuum. This resulted in 2.5 g of 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid as a brown solid. MS (ESI): [M+H]$^+$=720.5.

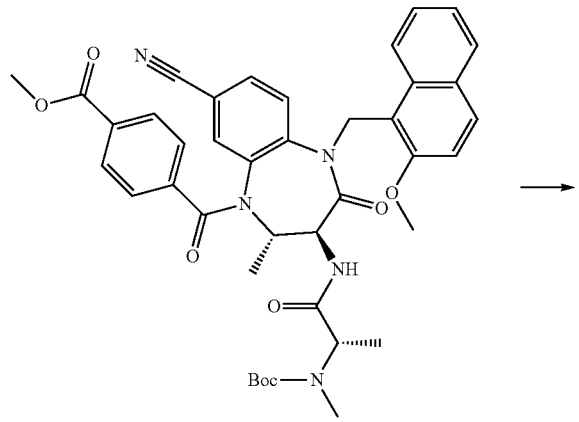

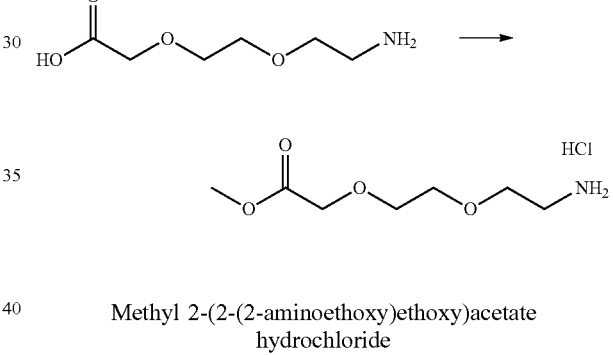

Methyl 2-(2-(2-aminoethoxy)ethoxy)acetate hydrochloride

To a solution of 2-[2-(2-aminoethoxy)ethoxy]acetic acid hydrochloride (500 mg, 2.505 mmol) in 2,2-dimethoxypropane (5 mL, 40.327 mmol) was added dropwise concentrated HCl (0.2 mL) at room temperature. The reaction mixture was stirred for 15 h at 25° C. and concentrated under vacuum. The residue was used directly without further purification.

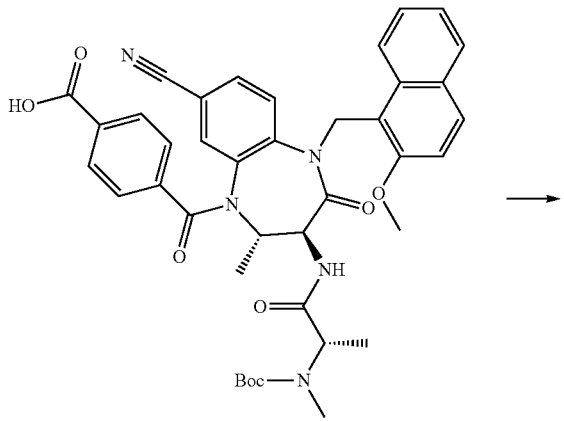

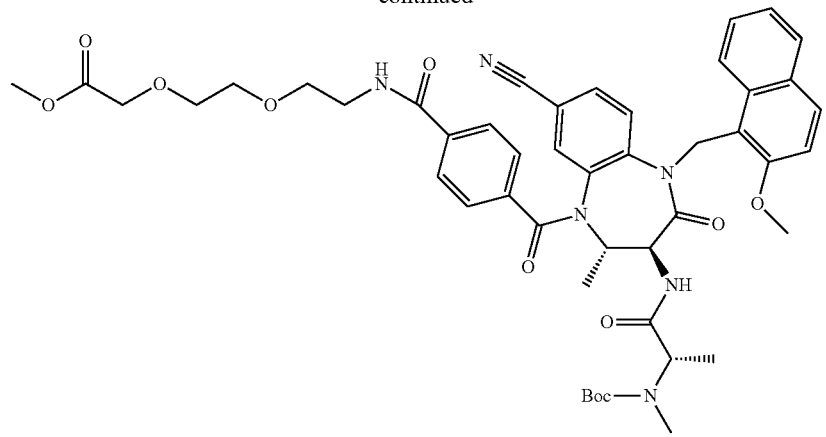

Methyl 2-(2-[2-[(4-[[(2S3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate To a solution of [(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid (500 mg, 0.695 mmol) in N,N-dimethylformamide (6 mL) was added crude methyl 2-[2-(2-aminoethoxy)ethoxy]acetate HCl salt from the previous step (500 mg), HATU (528 mg, 1.389 mmol) and DIPEA (897 mg, 6.94 mmol) under nitrogen at room temperature. The resulting solution was stirred for 1 hour at 25° C., and quenched with water. The resulting solution was extracted with dichloromethane and the organic layers combined. The organic phases were washed with brine and dried over anhydrous sodium sulfate and concentrated under vacuum. The residue was purified by flash chromatography on silica gel eluting with dichloromethane/methanol (20:1). This resulted in 550 mg (90%) of methyl 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate as a yellow solid. MS (ESI): [M+H]⁺=879.5.

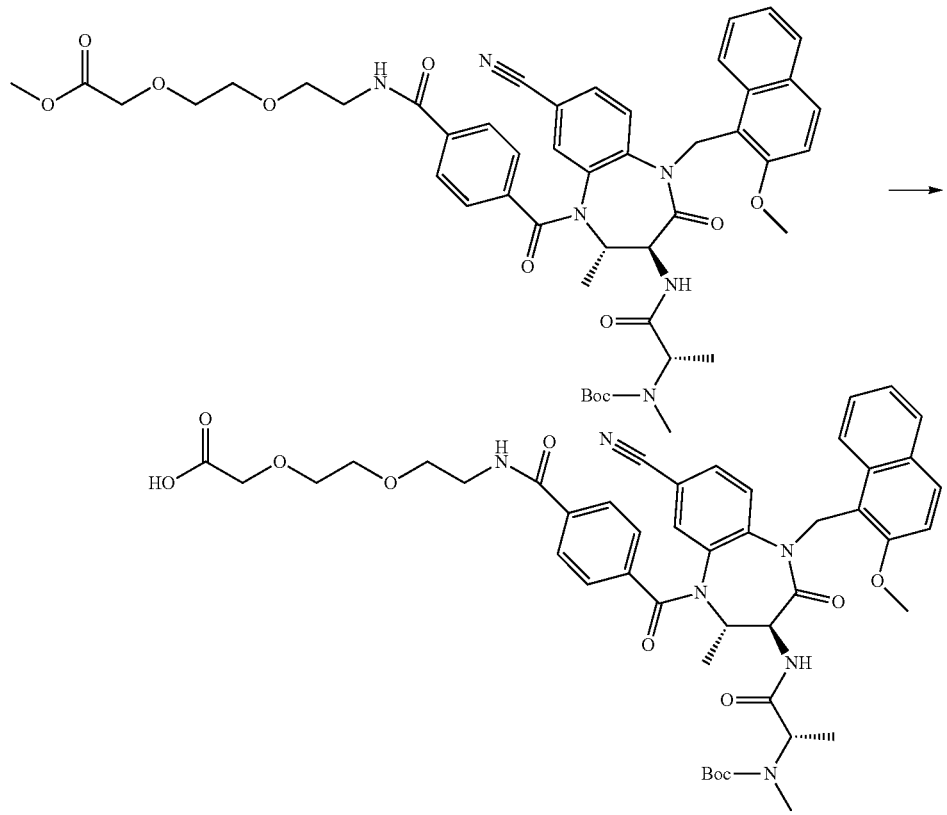

2-(2-[2-[(4-[[(2S,3S)-3-[(2S)-2-[[(Tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetic acid To a solution of methyl 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate (500 mg, 0.569 mmol) in tetrahydrofuran (8 mL) was added a solution of lithium hydroxide monohydrate (95 mg, 2.26 mmol) in water (1 mL) at room temperature. The mixture was stirred for 1 hour at 25° C. The mixture was diluted with water and acidified with 1 N citric acid to pH about 4, extracted with ethyl acetate (2×). The organic phases were combined and washed with brine, dried over sodium sulfate, and concentrated under reduced pressure. The residue was purified by reverse phase flash chromatography on C18 silica gel, mobile phase: 5 mM aqueous $NH_4HCO_3$ and $CH_3CN$ (0-95%) to afford 370 mg (75%) of 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetic acid as a white solid. MS (ESI): $[M+H]^+$=865.5. $^1$H NMR (400 MHz, DMSO-$d_6$): δ (ppm) 8.70 (d, J=8.6 Hz, 1H), 8.46 (t, J=5.5 Hz, 1H), 8.21 (d, J=8.7 Hz, 1H), 8.10 (d, J=8.6 Hz, 1H), 7.95 (d, J=9.1 Hz, 1H), 7.89 (dd, J=8.6, 1.9 Hz, 1H), 7.69 (d, J=8.1 Hz, 1H), 7.50 (d, J=9.2 Hz, 1H), 7.30 (m, 1H), 7.18 (d, J=1.9 Hz, 1H), 7.13 (t, J=7.5 Hz, 1H), 7.00 (d, J=8.1 Hz, 2H), 6.13 (d, J=15.1 Hz, 1H), 5.78 (d, J=8.0 Hz, 2H), 5.51 (d, J=15.0 Hz, 1H), 5.04 (brs, 1H), 4.61-4.52 (m, 1H), 4.22 (dd, J=11.9, 8.5 Hz, 1H), 3.99 (s, 2H), 3.96 (s, 3H), 3.68-3.44 (m, 7H), 3.37 (s, 1H), 2.76 (s, 3H), 1.40-1.31 (m, 12H), 1.12 (d, J=6.1 Hz, 3H).

ii. Attachment of a PB to an E3LB Via a Linker (L2)

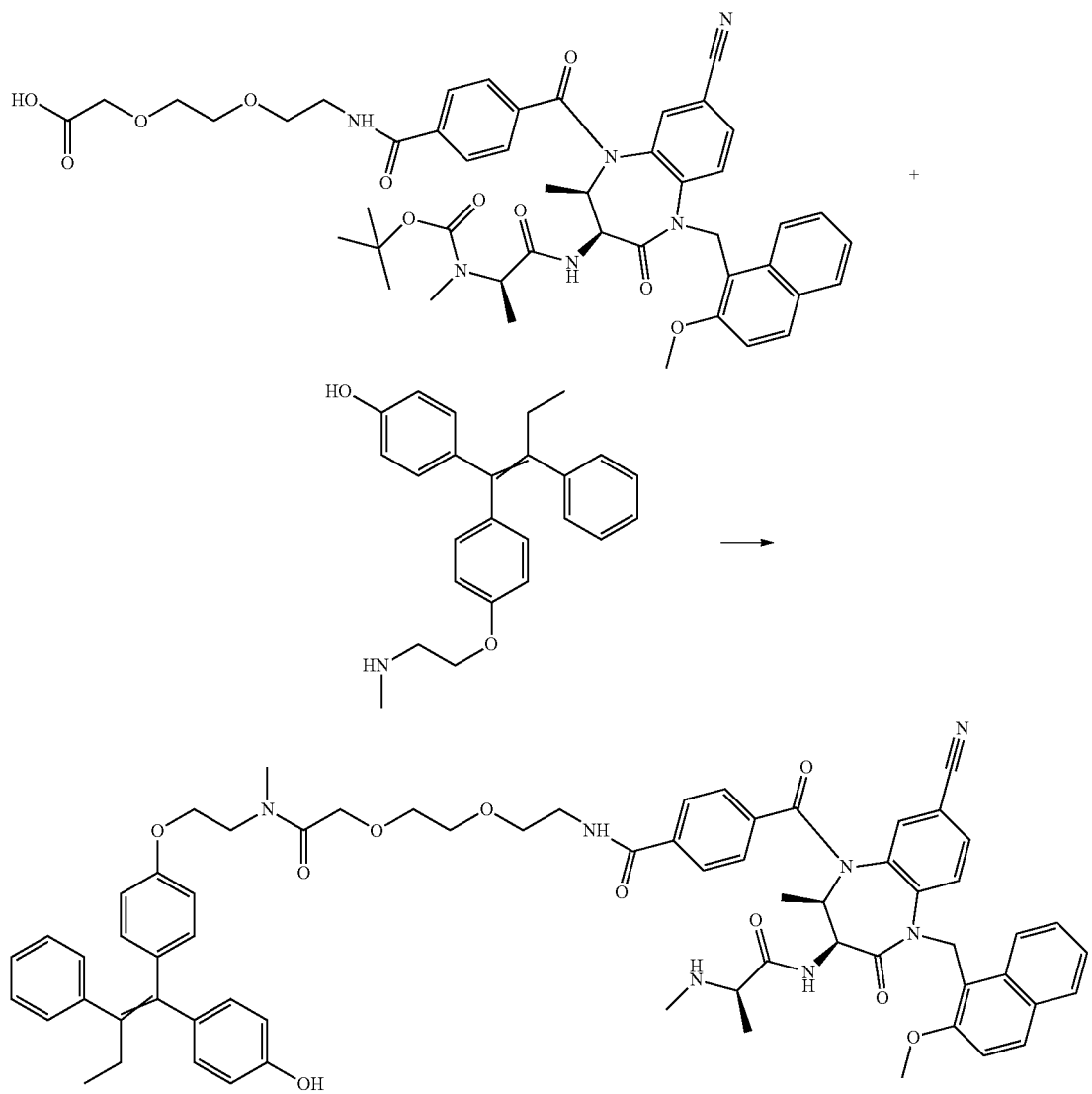

4-((2S,3S)-8-Cyano-5-((2-methoxynaphthalen-1-yl)methyl)-2-methyl-3-((S)-2-(methylamino)propanamido)-4-oxo-2,3,4,5-tetrahydro-1H-benzo[b][1,4]diazepine-1-carbonyl)-N-(2-(2-(2-((2-(4-(1-(4-hydroxyphenyl)-2-phenylbut-1-en-1-yl)phenoxy)ethyl)(methyl)amino)-2-oxoethoxy)ethoxy)ethyl)benzamide ("compound P1")

To a solution of 2-[2-[2-[[4-[(3S,4S)-3-[[(2S)-2-[tert-butoxycarbonyl(methyl)amino]propanoyl]amino]-7-cyano-1-[(2-methoxy-1-naphthyl)methyl]-4-methyl-2-oxo-3,4-dihydro-1,5-benzodiazepine-5-carbonyl]benzoyl]amino]ethoxy]ethoxy]acetic acid (74 mg, 0.0855 mmol) in 2-methyltetrahydrofuran (0.855 mL) was added HATU (1.1 equiv., 36.5 mg, 0.0941 mmol) and N,N-diisopropylethylamine (3.0 equiv., 0.045 mL, 0.257 mmol). The mixture was stirred at room temperature for 30 minutes, then a solution of 4-[1-[4-[2-(methylamino)ethoxy]phenyl]-2-phenyl-but-1-enyl]phenol (1.05 equiv., 33.5 mg, 0.0898 mmol) in 2-methyltetrahydrofuran (60, 0.5 mL, 400 mg, 5 mmol) was added, followed by 0.2 mL DMF. The mixture was stirred at room temperature for 22 h. Water was added and the solution was extracted 3 times with iPrOAc. The organic layers were combined then dried with sodium sulfate and concentrated in vacuo.

The crude material was dissolved in dichloromethane (0.85 mL) and trifluoroacetic acid (0.26 mL) was added dropwise. The reaction was stirred at room temperature until no gas evolution was observed. After 1 h, the solution was concentrated in vacuo and purified by reverse-phase HPLC to obtain 45 mg (45% yield over 2 steps) of the desired product.

M+H=560.9, 1120.7; δ $^1$H NMR (400 MHz, DMSO-d6) δ 9.39, 9.14 (overlapping s, 1H), 8.85-8.70 (m, 1H), 8.44-8.36 (m, 1H), 8.20 (d, J=8.8 Hz, 1H), 8.10 (d, J=8.6 Hz, 1H), 7.97-7.82 (m, 2H), 7.70-7.64 (m, 1H), 7.50-7.44 (m, 1H), 7.34-7.27 (m, 1H), 7.21-7.04 (m, 9H), 7.03-6.87 (m, 4H), 6.78-6.67 (m, 2H), 6.62-6.54 (m, 2H), 6.44-6.33 (m, 1H), 6.12 (d, J=15.1 Hz, 1H), 5.78 (d, J=8.0 Hz, 2H), 5.52 (d, J=15.0 Hz, 1H), 4.99-4.89 (m, 1H), 4.33-4.04 (m, 4H), 4.00-3.88 (m, 1H), 3.94 (s, 3H), 3.68-3.61 (m, 1H), 3.60-3.42 (m, 5H), 3.38-3.32 (m, 1H), 3.03-2.78 (m, 3H), 2.45-2.35 (m, 2H), 2.32 (s, 3H), 1.23 (d, J=6.4 Hz, 3H), 1.11 (d, J=6.1 Hz, 3H), 0.89-0.76 (m, 4H).

B. Preparation of L-PROTAC iii. Attachment of Linker L1 to PROTAC

165
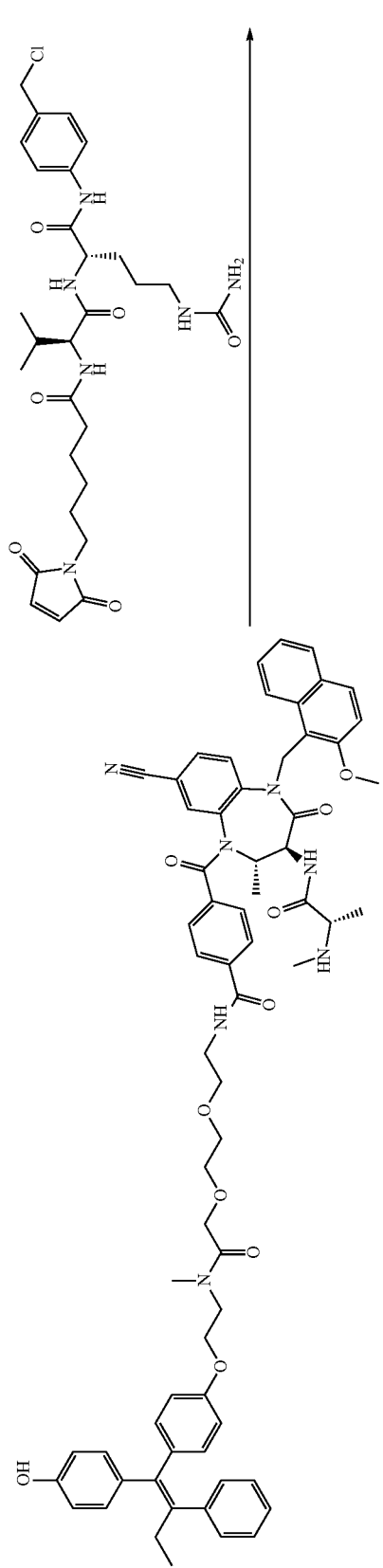
166
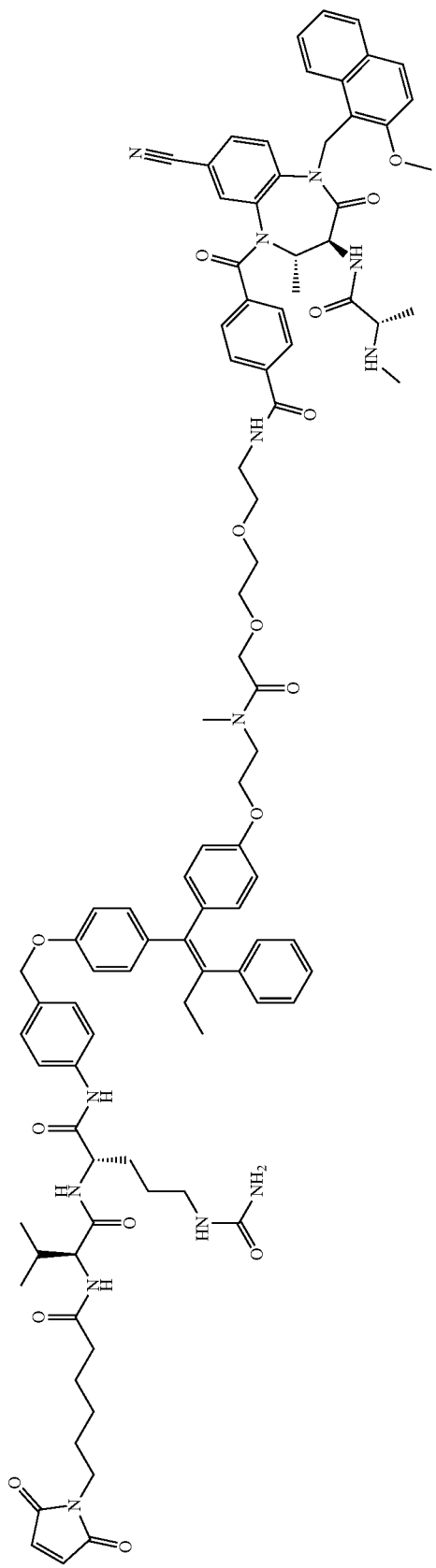

N-[(1S)-1-[[(1S)-(Carbamoylamino)-1-[(4-[4-[(1Z)-1-(4-[2-[2-(2-[2-[(4-[[(2S,3S)-8-cyano-5-[(2-methoxynaphthalen-1-yl)methyl]-2-methyl-3-[(2S)-2-(methylamino)propanamido]-4-oxo-2,3,4,5-tetrahydro-1H-1,5-benzodiazepin-1-yl]carbonyl]phenyl)formamido]ethoxy]ethoxy)-N-methylacetamido]ethoxy]phenyl)-2-phenylbut-1-en-1-yl]phenoxymethyl]phenyl)carbamoyl]butyl]carbamoyl]-2-methylpropyl]-6-(2,5-dioxo-2,5-dihydro-1H-pyrrol-1-yl)hexanamide ("compound LP2")

To a solution of (2S)—N-[(3S,4S)-7-cyano-5-[(4-[[2-(2-[[(2-[4-[(1Z)-1-(4-hydroxyphenyl)-2-phenylbut-1-en-1-yl]phenoxy]ethyl)(methyl)carbamoyl]methoxy]ethoxy)ethyl]carbamoyl]phenyl)carbonyl]-1-[(2-methoxynaphthalen-1-yl)methyl]-4-methyl-2-oxo-2,3,4,5-tetrahydro-H-1,5-benzodiazepin-3-yl]-2-(methylamino)propanamide (compound P1, 48 mg, 0.043 mmol) and N-[(1S)-1-{[(1S)-4-(carbamoylamino)-1-{[4-(chloromethyl)phenyl]carbamoyl}butyl]carbamoyl}-2-methylpropyl]-6-(2,5-dioxo-2,5-dihydro-1H-pyrrol-1-yl)hexanamide (90 mg, 0.152 mmol) in DMF (0.9 mL) at 0° C. was added $K_2CO_3$ (60 mg, 0.43 mmol). The reaction mixture was stirred for 4 h at 0° C., and diluted with precooled DMF (0.9 mL). The solid was filtered off. The filtrate was purified by Preparative HPLC with the following conditions: Column, SunFire Prep C18 OBD Column, 19*150 mm 5 um, 10 nm; mobile phase, water (0.1% TFA) and $CH_3CN$ (5% $CH_3CN$ up to 48% in 10 min); Detector, UV 254/220 nm to afford 22 mg (31%) of N-[(1S)-1-[[(1S)-4-(carbamoylamino)-1-[(4-[4-[(1Z)-1-(4-[2-[2-(2-[2-[(4-[[(2S,3S)-8-cyano-5-[(2-methoxynaphthalen-1-yl)methyl]-2-methyl-3-[(2S)-2-(methylamino)propanamido]-4-oxo-2,3,4,5-tetrahydro-1H-1,5-benzodiazepin-1-yl]carbonyl]phenyl)formamido]ethoxy]ethoxy)-N-methylacetamido]ethoxy]phenyl)-2-phenylbut-1-en-1-yl]phenoxymethyl]phenyl)carbamoyl]butyl]carbamoyl]-2-methylpropyl]-6-(2,5-dioxo-2,5-dihydro-1H-pyrrol-1-yl)hexanamide as a white solid. MS (ESI): [M+H]+=1675.1; $^1$H-NMR (400 MHz, DMSO-$d_6$): δ (ppm) 10.15 (s, 1H), 9.95-9.72 (m, 1H), 9.52-9.41 (m, 1H), 9.31-9.14 (m, 1H), 8.43 (brs, 1H), 8.20-8.18 (m, 1H), 8.17-8.07 (m, 2H), 7.93 (m, 2H), 7.70 (d, J=8 Hz, 1H), 7.70-7.65 (m, 3H), 7.48-7.42 (m, 2H), 7.41-7.36 (m, 1H), 7.33-7.28 (m, 1H), 7.23 (m, 1H), 7.18-7.07 (m, 7H), 7.02-7.01 (m, 1H), 6.99 (s, 3H), 6.96-6.92 (m, 2H), 6.76-6.67 (m, 2H), 6.60-6.58 (m, 2H), 6.40 (d, J=8.4 Hz, 1H), 6.13-6.08 (m, 1H), 5.99 (s, 1H), 5.80 (d, J=7.6 Hz, 2H), 5.55 (d, J=15.2 Hz, 1H), 5.44 (brs, 1H), 5.02-4.93 (m, 1H), 7.43-4.36 (m, 3H), 4.26-4.02 (m, 6H), 3.95-3.88 (m, 4H), 3.66-3.63 (m, 3H), 3.57-3.53 (m, 4H), 3.39-3.36 (m, 4H), 3.05-2.81 (m, 5H), 2.68 (s, 2H), 2.42-2.39 (m, 3H), 2.22-2.07 (m, 2H), 2.03-1.91 (m, 1H), 1.71 (brs, 2H), 1.62 (brs, 3H), 1.50-1.36 (m, 6H), 1.21-1.17 (m, 5H), 0.87-0.82 (m, 10H).

C. Preparation of PAC iv. Attachment of Antibody (Ab) to PROTAC Via Linker L1

Conjugation of a PROTAC to HER2 and B7H4 antibodies to yield PROTAC-antibody conjugates (PACs) was accomplished as follows.

A cysteine-engineered antibody (THIOMAB™ antibody), in 10 mM succinate, pH 5, 150 mM NaCl, 2 mM EDTA, is pH-adjusted to pH 7.5-8.5 with 1M Tris. Between three and ten equivalents of a linker L-PROTAC with a thiol-reactive group is dissolved in DMF or DMA and added to the reduced, reoxidized, and pH-adjusted antibody. The reaction is incubated at room temperature or 37° C. and monitored until completion (1 to about 24 hours), as determined by LC-MS analysis of the reaction mixture. When the reaction is complete, the conjugate is purified by one or any combination of several methods, the goal being to remove remaining unreacted linker L-PROTAC intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used.

The THIOMAB™ antibody PROTAC conjugates were formulated into 20 mM His/acetate, pH 5, with 240 mM sucrose using either gel filtration or dialysis. The purified conjugate is concentrated by centrifugal ultrafiltration and filtered through a 0.2-μm filter under sterile conditions and frozen for storage.

Example 2

Characterization of PACs

The PACs were characterized to determine protein concentration (e.g., by BCA assay), aggregation level (by analytical SEC), PAR (e.g., by LC-MS).

Size exclusion chromatography is performed on conjugates using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis is performed on conjugates using an Agilent TOF 6530 ESI instrument. As an example, the PAC is treated with 1:500 w/w Endoproteinase Lys C (Promega) in Tris, pH 7.5, for 30 min at 37° C. The resulting cleavage fragments are loaded onto a 1000A (Angstrom), 8 μm (micron) PLRP-S (highly cross-linked polystyrene) column heated to 80° C. and eluted with a gradient of 30% B to 40% B in 10 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and PROTAC-conjugated Fab was usually achieved. The obtained m/z spectra were deconvoluted using Mass Hunter™ software (Agilent Technologies) to calculate the mass of the antibody fragments.

TABLE 28

Characterization of several PACs.

| | | PAC Formula Ab-(L1-D)$_p$ | | | % |
|---|---|---|---|---|---|
| PAC | Ab | L1 | D | p | Aggregate (Final) |
| PAC 1 | Thio Hu Anti-Her2 7C2 LC K149C | MC-VC-PAB | Compound P1 | 2 | 4.8 |

TABLE 28-continued

Characterization of several PACs.

| PAC | PAC Formula Ab-(L1-D)$_p$ | | | | % Aggregate (Final) |
|---|---|---|---|---|---|
| | Ab | L1 | D | p | |
| PAC 2 | Thio Hu Anti-B7-H4 1D11v1.9_VarD LC K149C | MC-VC-PAB | Compound P1 | 2 | 4.7 |
| PAC 3 | Thio Hu anti-Her2 7C2 LC:K149C | MC-VC-PAB | Compound P1 | 2.2 | 3.4 |
| PAC 4 | Thio Hu Anti-B7-H4 1D11v1.9_VarD LC K149C | MC-VC-PAB | Compound P1 | 2.29 | 2.37 |
| PAC 5 | Thio Her2 7C2 HC: A140C | MC-VC-PAB | Compound P1 | 1.7 | 6.3 |

MC-VC-PAB refers to (6-maleimidocaproyl)-(valine-citrulline)-(p-aminobenzyl). Thio means THIOMAB™ antibody. LC K149C means that the K at position 149 has been changed to C in the light chain Hu means human Anti HER2 and Anti B7-H4 mean antibodies that bind to HER2 and B7-H4 respectively.

Example 3

Detection of Effects of a HER-2 Containing PAC on Estrogen Receptor Alpha Density The following experimental describes the detection of estrogen receptor alpha (ER-α) in MCF7-neo/HER2 cell lines by Western blot after treatment with PROTACs and PROTAC-antibody conjugates.

MCF7 cells engineered to express the HER2/NEU receptor were seeded in a 12 well plate with a cell density of 40×10$^4$ cells per well. To deplete estradiol, cells were grown in phenol red free RPMI media containing 10% (v/v) charcoal stripped serum (Gemini Bio-products), 4 mM L-glutamine, 100 U each of penicillin and streptomycin and nonessential amino acids (Gibco, Life Technologies). After 3 days, cells were trypsinized and re-seeded at half the density.

The following day unconjugated PROTAC or PROTAC conjugated to antibody (PAC) was added to the medium at 10 μg/ml (=134 nM PROTAC) and 1 μg/ml (=13.4 nM PROTAC). After 3 days, cells were washed once with PBS and lysed in 100 μL urea lysis buffer (6M Urea, 20 mM Tris pH7.5, 12.5 mM NaCl, 2.5 mM MgCl$_2$, 0.1% Triton X-100, protease inhibitor cocktail (Roche)). Total protein concentrations were determined by BCA (ThermoFisher). For each sample, 10 ug of total cellular protein was separated on 4-12% Bis-Tris gel and transferred to Invitrolon PVDF membrane (Thermofisher). Membranes were blocked in PBS-0.1% Tween-20 containing 10% non fat dry milk and probed with primary antibodies against Estrogen Receptor α (Santa Cruz, SC-8002) and GAPDH (Santa Cruz, SC25778 HRP) at 1:1000 dilution followed by secondary antibodies against mouse IgG (GE Healthcare) at 1:5000 dilution.

Protein bands were visualized using chemiluminescence (Perkin Elmer). The results are shown in FIG. 1.

Example 4

Quantitation of Effects of a HER-2 Containing PAC on Estrogen Receptor Alpha Density The following experimental describes the quantitation of ERα in MCF7-neo/HER2 cells after treatment with PROTACs and PROTAC-antibody conjugates.

Cell Plating neoMCF7/HER2 cells (CL130220) were thawed at 37° C. then transferred to growth media (RPMI, 10% Fetal Bovine Serum F2442 (FBS)) by spinning cells down twice at 1200 RCF for three minutes and removing and replacing supernatant with growth media. Cells were then transferred to a 150 cm$^2$ flask (Ref: 431465) and grown until confluent. Once confluent, cells were washed once in PBS, PBS aspirated, and 10 ml of 10×0.5% Trypsin (Cat #15400-054) was added to the flask to cover cells. Excess trypsin was immediately aspirated and flask was transferred to 37° C. incubator for 5 min. After incubation 20 ml growth media (phenol red free-RPMI (Cat #11835-030) 10% charcoal stripped-FBS (SKU: F6765)) was added to flask and cell density was determined using a Vicell instrument. Growth media was added to make cellular density of 10,000 cells/0.05 ml. 50 ul of cells were then transferred to each well of two Greiner 384 well plates (Ref: 781946) that were stored overnight in a 37° C. incubator before compound treatment the following day.

Compound Treatment

PACs were thawed at RT and were each diluted to 60 ug/ml in 37 C growth media, followed by a 20-point 2X serial dilution across a 384 well plate (Ref: 781091). 10 ul of each sample from the serial dilution was transferred to the wells of the cell plates. The highest working concentration of the PACs was 10 ug/ml. Cell plate columns 1, 2, 23 and 24 were left untreated for data normalization while Columns 3-22 contained the PAC dilutions. After compound treatment cell plates were stored in a 37 C incubator for 72 h.

Staining

After the 72 h compound treatment, cells were fixed for 30 min with 15 ul of 16% paraformaldehyde (Cat #15710-S) in each well. Contents were aspirated, 50 ul of Permeabilization/Block buffer (PBS, BSA 0.5% (w/v), Triton X100 0.1% (v/v)), was added to each well. After 10 min the Permeabilization/Block buffer was aspirated and washed twice with PBS. Wells were then aspirated and treated with 25 ul 1/1000 of mAb Anti-ESR1 (Clone F10) (Santa Cruz sc-8002) in Permeabilization/Block Buffer and incubated at RT for 2 h before being washed 4× in PBS. Contents of the wells were aspirated again and treated with 25 ul 1/1000 Alexafluor 488 conjugated anti-mouse (LifeTechnologies #A21202) and 1/1000 Hoechst 33258 (Cat # H3569) and incubated for 3 h. Plates were then washed 3× in PBS and sealed.

Data Collection

Cellomics Arrayscan was used to collect the cell count and ERα fluorescence intensity (MeanCircAvgIntenCh2), which is proportional to the amount of ERα present in the nucleus. Data was then normalized to non-treated cell controls, and plotted in GraphPad Prism. GraphPad Prism calculated the EC$_{50}$s using the "lag(inhibitor) vs. response—Variable Slope" function.

Table 29 reports the $IC_{50}$ data from the quantitation experiment.

TABLE 29

| | PAC1<br>Anti-HER2(Endox-XIAP) | PAC2<br>Anti-B7H4(Endox-XIAP) |
|---|---|---|
| $IC_{50}$ (g/ml) | 1.32E-07 | — |

The results are shown in FIG. 2. Treatment of HER2 expressing cells with HER2 antibody containing PAC Anti-HER2 (Endox-XIAP) resulted in a marked decreased Estrogen Receptor-alpha (ERα) levels. Treatment of the HER2 expressing cells with the B7-H4 antibody containing PAC Anti-B7-H4 (Endox-XIAP) did not result in a substantial decrease in ERα levels.

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A conjugate having the chemical structure
   Ab-(L1-D)$_p$, wherein
D is a PROTAC having the structure E3LB-L2-PB, wherein
E3LB is an E3 ligase binding group covalently bound to L2, wherein the E3 ligase is a tetrahydro-benzodiazepinone or a pharmaceutically acceptable salt thereof, and
wherein E3LB is

[chemical structure]

L2 is a linker covalently bound to E3LB and PB, and
PB is a protein binding group covalently bound to L2;
Ab is an antibody covalently bound to L1;
L1 is a linker covalently bound to Ab and D; and
p has a value from about 1 to about 8.

2. The conjugate of claim 1, wherein PB is a group that targets Estrogen Receptor alpha (ERa).

3. The conjugate of claim 1, wherein the antibody binds to HER2 or B7-H4.

4. The conjugate of claim 3, wherein the antibody binds to HER2.

5. The conjugate of claim 1, wherein L1 is a peptidomimetic linker represented by the following formula:

-Str-(PM)-Spwherein,
Str is a stretcher unit covalently attached to Ab;
Ab is an antibody;
Sp is a bond or spacer unit covalently attached to a PROTAC moiety;
PM is a non-peptide chemical moiety selected from the group consisting of:

[chemical structures] and

[chemical structure];

W is —NH-heterocycloalkyl- or heterocycloalkyl;
Y is heteroaryl, aryl, —C(O)C$_1$-C$_6$alkylene, C$_1$-C$_6$alkylene-NH$_2$, C$_1$-C$_6$alkylene-NH—CH$_3$, C$_1$-C$_6$alkylene-N—(CH$_3$)$_2$, C$_1$-C$_6$alkenyl or C$_1$-C$_6$alkylenyl;
each R$^1$ is independently C$_1$-C$_{10}$alkyl, C$_1$-C$_{10}$alkenyl, (C$_1$-C$_6$alkyl)NHC(NH)NH$_2$, (C$_1$-C$_6$alkyl)NHC(O)NH$_2$, (C$_1$-C$_{10}$alkyl)NHC(NH)NH$_2$ or (C$_1$-C$_{10}$alkyl)NHC(O)NH$_2$;
R$^3$ and R$^2$ are each independently H, C$_1$-C$_{10}$alkenyl, arylalkyl or heteroarylalkyl, or R$^3$ and R$^2$ together may form a C$_3$-C$_7$cycloalkyl; and
R$^4$ and R$^5$ are each independently C$_1$-C$_{10}$alkyl, C$_1$-C$_{10}$alkenyl, arylalkyl, heteroarylalkyl, (C$_1$-C$_{10}$alkyl)OCH$_2$—, or R$^4$ and R$^5$ together may form a C$_3$-C$_7$cycloalkyl ring.

6. The conjugate of claim 5, wherein Y is heteroaryl; R$^4$ and R$^5$ together form a cyclobutyl ring.

7. The conjugate of claim 5, wherein Y is a moiety selected from the group consisting of

[chemical structures] AND

[chemical structure].

8. The conjugate of claim 5, wherein Str is a chemical moiety represented by the following formula:

[chemical structure] (Ab)

wherein R$^6$ is selected from the group consisting of C$_1$-C$_{10}$alkylene, C$_1$-C$_{10}$alkenyl, C$_3$-C$_8$cycloalkyl, (C$_1$-C$_8$alkylene)O—, and C$_1$-C$_{10}$alkylene-C(O)N(Ra)—C$_2$-C$_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, C$_3$-C$_8$cycloalkyl, C$_4$-C$_7$heterocycloalkyl, heteroarylalkyl, aryl arylalkyl, and heteroaryl, wherein each R$^a$ is independently H or C$_1$-C$_6$alkyl; and
Sp is —C$_1$-C$_6$alkylene-C(O)NH— or —Ar—R$^b$—, wherein Ar is aryl or heteroaryl, and R$^b$ is (C$_1$-C$_{10}$alkylene)O—.

9. The conjugate of claim 5, wherein L1 has the following formula

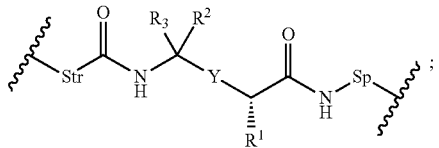

R$^1$ is C$_1$-C$_6$alkyl, C$_1$-C$_6$alkenyl, (C$_1$-C$_6$alkyl)NHC(NH)NH$_2$ or (C$_1$-C$_6$alkyl)NHC(O)NH$_2$; and R$^3$ and R$^2$ are each independently H, C$_1$-C$_{10}$alkyl.

10. The conjugate of claim 5, wherein L1 has the following formula:

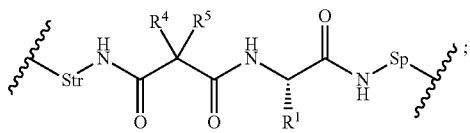

R$^1$ is C$_1$-C$_6$alkyl, (C$_1$-C$_6$alkyl)NHC(NH)NH$_2$ or (C$_1$-C$_6$alkyl)NHC(O)NH$_2$; and R$^4$ and R$^5$ together form a C$_3$-C$_7$cycloalkyl ring.

11. The conjugate of claim 5, wherein L1 has the following formula:

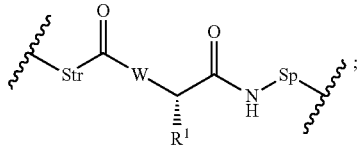

R$^1$ is C$_1$-C$_6$alkyl, (C$_1$-C$_6$alkyl)NHC(NH)NH$_2$ or (C$_1$-C$_6$alkyl)NHC(O)NH$_2$.

12. The conjugate compound of claim 1, having the formula:

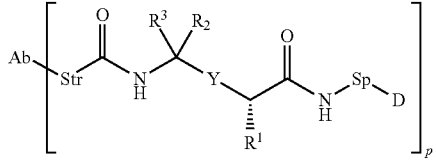

wherein

Sp is a bond or spacer unit covalently attached to PROTAC moiety D;

Y is heteroaryl, aryl, —C(O)C$_1$-C$_6$alkylene, C$_1$-C$_6$alkylene-NH$_2$, C$_1$-C$_6$alkylene-NH—CH$_3$, C$_1$-C$_6$alkylene-N—(CH$_3$)$_2$, C$_1$-C$_6$alkenyl or C$_1$-C$_6$alkylenyl;

R$^1$ is independently C$_1$-C$_{10}$alkyl, C$_1$-C$_{10}$alkenyl, (C$_1$-C$_6$alkyl)NHC(NH)NH$_2$, (C$_1$-C$_6$alkyl)NHC(O)NH$_2$, (C$_1$-C$_{10}$alkyl)NHC(NH)NH$_2$ or (C$_1$-C$_{10}$alkyl)NHC(O)NH$_2$;

R$^3$ and R$^2$ are each independently H, C$_1$-C$_{10}$alkenyl, arylalkyl or heteroarylalkyl, or R$^3$ and R$^2$ together may form a C$_3$-C$_7$cycloalkyl; and Str is a chemical moiety represented by the following formula:

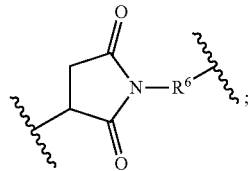

R$^6$ is selected from the group consisting of C$_1$-C$_{10}$alkylene, and C$_1$-C$_{10}$alkylene-C(O)N(Ra)—C$_2$-C$_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, C$_3$-C$_8$cycloalkyl, C$_4$-C$_7$heterocycloalkyl, heteroarylalkyl, aryl, arylalkyl, heteroarylalkyl and heteroaryl, wherein each R$^a$ is independently H or C$_1$-C$_6$alkyl; and p is 1, 2, 3 or 4.

13. The conjugate of claim 1, having the formula:

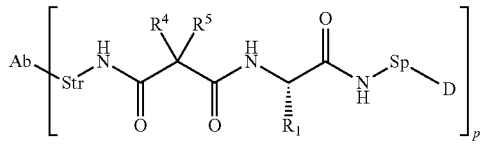

wherein

Sp is a bond or spacer unit covalently attached to PROTAC moiety D;

R$^4$ and R$^5$ are each independently C$_1$-C$_{10}$alkyl, C$_1$-C$_{10}$alkenyl, arylalkyl, heteroarylalkyl, (C$_1$-C$_{10}$alkyl)OCH$_2$—, or R$^4$ and R$^5$ together may form a C$_3$-C$_7$cycloalkyl ring;

R$^1$ is independently C$_1$-C$_{10}$alkyl, (C$_1$-C$_6$alkyl)NHC(NH)NH$_2$, (C$_1$-C$_6$alkyl)NHC(O)NH$_2$, (C$_1$-C$_{10}$alkyl)NHC(NH)NH$_2$ or (C$_1$-C$_{10}$alkyl)NHC(O)NH$_2$;

Str is a chemical moiety represented by the following formula:

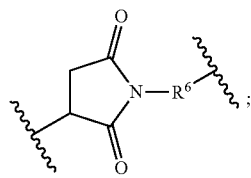

R$^6$ is selected from the group consisting of C$_1$-C$_{10}$alkylene, and C$_1$-C$_{10}$alkylene-C(O)N(Ra)—C$_2$-C$_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, C$_3$-C$_8$cycloalkyl, C$_4$-C$_7$heterocycloalkyl, aryl, arylalkyl, heteroarylalkyl and heteroaryl, wherein each R$^a$ is independently H or C$_1$-C$_6$alkyl; and p is 1, 2, 3 or 4.

14. The conjugate of claim 12, wherein Y is heteroaryl, aryl or alkenyl; $R^6$ is $C_1$-$C_{10}$alkylene.

15. The conjugate of claim 12, wherein Y is selected from the group consisting of:

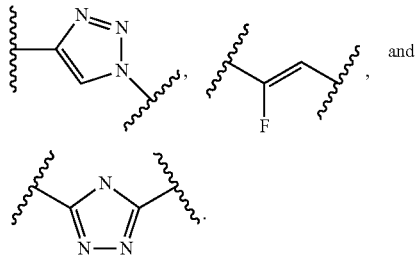

16. The conjugate of claim 12, wherein Str is a chemical moiety represented by the following formula:

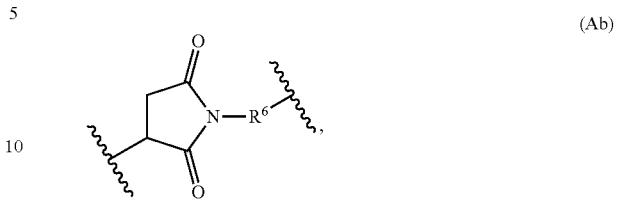

(Ab)

$R^6$ is $C_1$-$C_6$alkylene;

Sp is —$C_1$-$C_6$alkylene-C(O)NH— or —Ar—$R^b$—, where Ar is aryl, and $R^b$ is ($C_1$-$C_6$alkylene)O—.

17. The conjugate of claim 1, having the formula:

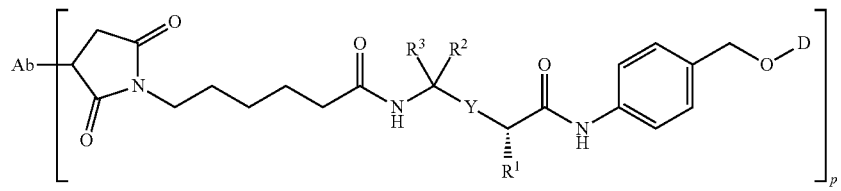

wherein
Y is heteroaryl, aryl, —C(O)$C_1$-$C_6$alkylene, $C_1$-$C_6$alkylene-NH$_2$, $C_1$-$C_6$alkylene-NH—CH$_3$, $C_1$-$C_6$alkylene-N—(CH$_3$)$_2$, $C_1$-$C_6$alkenyl or $C_1$-$C_6$alkylenyl;

$R^1$ is $C_1$-$C_6$alkyl-NH$_2$, ($C_1$-$C_6$alkyl)NHC(NH)NH$_2$ or ($C_1$-$C_6$alkyl)NHC(O)NH$_2$;

$R^3$ and $R^2$ are each independently H, $C_1$-$C_{10}$alkenyl, arylalkyl or heteroarylalkyl, or $R^3$ and $R^2$ together may form a $C_3$-$C_7$cycloalkyl; and p is 1, 2, 3 or 4;

or the formula:

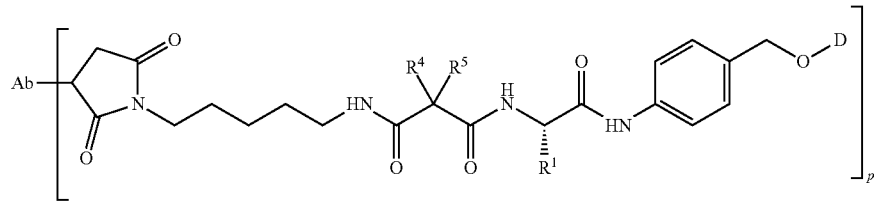

wherein
p is 1, 2, 3 or 4;

$R^1$ is $C_1$-$C_6$alkyl-Nth, ($C_1$-$C_6$alkyl)NHC(NH)NH$_2$ or ($C_1$-$C_6$alkyl)NHC(O)NH$_2$;

$R^4$ and $R^5$ are each independently $C_1$-$C_6$alkyl, wherein said alkyl are unsubstituted, or $R^4$ and $R^5$ may form a $C_3$-$C_7$cycloalkyl ring;

or the formula:

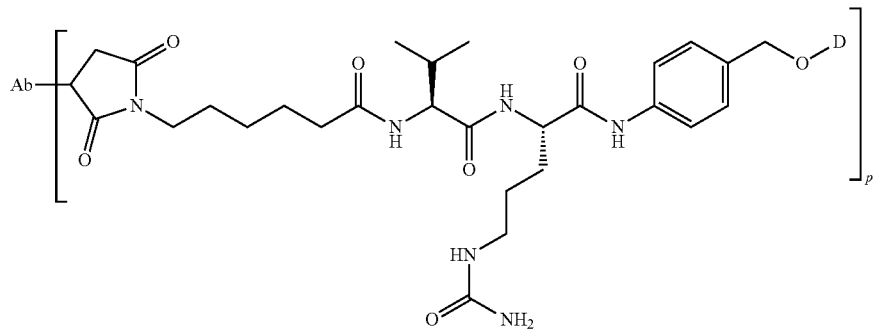

wherein
p is 1, 2, 3 or 4.

18. The conjugate of claim 1 selected from the group consisting of PAC1, PAC2, PAC3, PAC4 and PACS.

19. The conjugate of claim 1, wherein p is from about 1.0 to about 3.

20. A pharmaceutical composition comprising a conjugate of claim 1 and one or more pharmaceutically acceptable excipients.

21. A method of treating a HER-2 positive cancer in a human in need thereof, comprising administering to said human an effective amount of a composition of claim 20.

22. The method of claim 21, wherein the HER2-positive cancer is breast cancer or gastric cancer.

* * * * *

UNITED STATES PATENT AND TRADEMARK OFFICE
CERTIFICATE OF CORRECTION

PATENT NO. : 11,666,581 B2
APPLICATION NO. : 16/194897
DATED : June 6, 2023
INVENTOR(S) : Pillow et al.

Page 1 of 2

It is certified that error appears in the above-identified patent and that said Letters Patent is hereby corrected as shown below:

In the Claims

Column 236,
Line 17, at Claim 5, "H, $C_1$-$C_{10}$alkenyl" should read --H, $C_1$-$C_{10}$alkyl, $C_1$-$C_{10}$alkenyl--;
Lines 56-57, at Claim 8, "$C_1$-$C_{10}$alkylene-C(O)N(Ra)—$C_2$-$C_6$alkylene" should read
--$C_1$-$C_{10}$alkylene–C(O)N($R^a$)—$C_2$-$C_6$alkylene--.

Column 237,
Line 65, at Claim 12, "H, $C_1$-$C_{10}$alkenyl" should read --H, $C_1$-$C_{10}$alkyl, $C_1$-$C_{10}$alkenyl--.

Column 238,
Lines 15-16, at Claim 12, "$C_1$-$C_{10}$alkylene-C(O)N(Ra)—$C_2$-$C_6$alkylene" should read
--$C_1$-$C_{10}$alkylene–C(O)N($R^a$)—$C_2$-$C_6$alkylene--;
Line 22, at Claim 12, "arylalkyl, heteroarylalkyl and" should read --arylalkyl, and--;
Lines 41-42, at Claim 13, "$C_1$-$C_{10}$alkyl, ($C_1$-$C_6$alkyl)NHC(NH)$NH_2$" should read
--$C_1$-$C_{10}$alkyl, $C_1$-$C_{10}$alkenyl, ($C_1$-$C_6$alkyl)NHC(NH)$NH_2$--;
Lines 58-59, at Claim 13, "$C_1$-$C_{10}$alkylene-C(O)N(Ra)—$C_2$-$C_6$alkylene" should read
--$C_1$-$C_{10}$alkylene–C(O)N($R^a$)—$C_2$-$C_6$alkylene--.

Column 240,
Lines 5-13, at Claim 16, the figure should appear as follows:

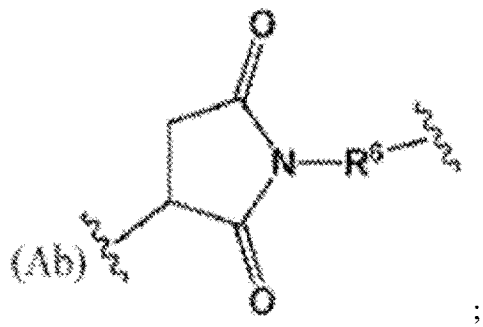

;

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,666,581 B2

Line 39, at Claim 17, "H, $C_1$-$C_{10}$alkenyl" should read --H, $C_1$-$C_{10}$alkyl, $C_1$-$C_{10}$alkenyl--;
Line 62, at Claim 17, "$C_1$-$C_6$alkyl-Nth" should read --$C_1$-$C_6$alkyl-$NH_2$--.

Column 241,
Line 21, at Claim 18, "PACS" should read --PAC5--.

SEQUENCE LISTING

```
<160> NUMBER OF SEQ ID NOS: 98

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000
```

<210> SEQ ID NO 5

<400> SEQUENCE: 5

000

<210> SEQ ID NO 6

<400> SEQUENCE: 6

000

<210> SEQ ID NO 7
<211> LENGTH: 107
<212> TYPE: PRT
<213> ORGANISM: homo sapiens

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105
```

<210> SEQ ID NO 8
<211> LENGTH: 120
<212> TYPE: PRT
<213> ORGANISM: homo sapiens

<400> SEQUENCE: 8

```
Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
            115                 120
```

<210> SEQ ID NO 9
<211> LENGTH: 11

```
<212> TYPE: PRT
<213> ORGANISM: homo sapiens

<400> SEQUENCE: 9

Ser Ala Ser Gln Gly Ile Ser Asn Tyr Leu Asn
1               5                   10

<210> SEQ ID NO 10
<211> LENGTH: 7
<212> TYPE: PRT
<213> ORGANISM: homo sapiens

<400> SEQUENCE: 10

Tyr Thr Ser Asn Leu His Ser
1               5

<210> SEQ ID NO 11
<211> LENGTH: 9
<212> TYPE: PRT
<213> ORGANISM: homo sapiens

<400> SEQUENCE: 11

Gln Gln Tyr Ser Glu Leu Pro Trp Thr
1               5

<210> SEQ ID NO 12
<211> LENGTH: 10
<212> TYPE: PRT
<213> ORGANISM: homo sapiens

<400> SEQUENCE: 12

Gly Phe Ser Leu Thr Gly Tyr Ser Val Asn
1               5                   10

<210> SEQ ID NO 13
<211> LENGTH: 16
<212> TYPE: PRT
<213> ORGANISM: homo sapiens

<400> SEQUENCE: 13

Met Ile Trp Gly Asp Gly Ser Thr Asp Tyr Asn Ser Ala Leu Lys Ser
1               5                   10                  15

<210> SEQ ID NO 14
<211> LENGTH: 12
<212> TYPE: PRT
<213> ORGANISM: homo sapiens

<400> SEQUENCE: 14

Asp Tyr Tyr Val Asn Tyr Ala Ser Trp Phe Ala Tyr
1               5                   10

<210> SEQ ID NO 15
<211> LENGTH: 214
<212> TYPE: PRT
<213> ORGANISM: homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45
```

Tyr Tyr Thr Ser Asn Leu His Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 450
<212> TYPE: PRT
<213> ORGANISM: homo sapiens

<400> SEQUENCE: 16

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
                195                 200                 205
Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 17
<211> LENGTH: 112
<212> TYPE: PRT
<213> ORGANISM: homo sapiens

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
                20                  25                  30

Arg Phe Thr Tyr Met His Trp Tyr Gln Gln Lys Pro Gly Gln Pro Pro
            35                  40                  45

Lys Leu Leu Ile Lys Tyr Ala Ser Ile Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
                100                 105                 110
```

<210> SEQ ID NO 18
<211> LENGTH: 118
<212> TYPE: PRT
<213> ORGANISM: homo sapiens

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser
        115

<210> SEQ ID NO 19
<211> LENGTH: 15
<212> TYPE: PRT
<213> ORGANISM: homo sapiens

<400> SEQUENCE: 19

Arg Ala Ser Gln Ser Val Ser Gly Ser Arg Phe Thr Tyr Met His
1               5                   10                  15

<210> SEQ ID NO 20
<211> LENGTH: 7
<212> TYPE: PRT
<213> ORGANISM: homo sapiens

<400> SEQUENCE: 20

Tyr Ala Ser Ile Leu Glu Ser
1               5

<210> SEQ ID NO 21
<211> LENGTH: 10
<212> TYPE: PRT
<213> ORGANISM: homo sapiens

<400> SEQUENCE: 21

Gln His Ser Trp Glu Ile Pro Pro Trp Thr
1               5                   10

<210> SEQ ID NO 22
<211> LENGTH: 5
<212> TYPE: PRT
<213> ORGANISM: homo sapiens

<400> SEQUENCE: 22

Gly Tyr Trp Met Asn
1               5

<210> SEQ ID NO 23
<211> LENGTH: 17

```
<212> TYPE: PRT
<213> ORGANISM: homo sapiens

<400> SEQUENCE: 23

Met Ile His Pro Leu Asp Ala Glu Ile Arg Ala Asn Gln Lys Phe Arg
1               5                   10                  15
Asp

<210> SEQ ID NO 24
<211> LENGTH: 9
<212> TYPE: PRT
<213> ORGANISM: homo sapiens

<400> SEQUENCE: 24

Gly Thr Tyr Asp Gly Gly Phe Glu Tyr
1               5

<210> SEQ ID NO 25
<211> LENGTH: 219
<212> TYPE: PRT
<213> ORGANISM: homo sapiens

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: homo sapiens

<400> SEQUENCE: 26
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
                  420                 425                 430
Leu His Asn His Tyr Thr Gln Lys Ser Leu Ser Leu Ser Pro Gly Lys
            435                 440                 445

<210> SEQ ID NO 27
<211> LENGTH: 17
<212> TYPE: PRT
<213> ORGANISM: homo sapiens

<400> SEQUENCE: 27

Met Ile His Pro Met Asp Ser Glu Ile Arg Ala Asn Gln Lys Phe Arg
1               5                   10                  15

Asp

<210> SEQ ID NO 28
<211> LENGTH: 17
<212> TYPE: PRT
<213> ORGANISM: homo sapiens

<400> SEQUENCE: 28

Met Ile His Pro Leu Asp Ser Glu Ile Arg Ala Asn Gln Lys Phe Arg
1               5                   10                  15

Asp

<210> SEQ ID NO 29
<211> LENGTH: 9
<212> TYPE: PRT
<213> ORGANISM: homo sapiens

<400> SEQUENCE: 29

Gly Thr Tyr Asp Gly Gly Phe Lys Tyr
1               5

<210> SEQ ID NO 30
<211> LENGTH: 219
<212> TYPE: PRT
<213> ORGANISM: homo sapiens

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 31
<211> LENGTH: 448
<212> TYPE: PRT
<213> ORGANISM: homo sapiens

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr

```
            305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 32
<211> LENGTH: 448
<212> TYPE: PRT
<213> ORGANISM: homo sapiens

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Trp Met Asn Trp Val Arg Gln Ala Pro Gly Gln Gly Leu Glu Trp Ile
                35                  40                  45

Gly Met Ile His Pro Leu Asp Ala Glu Ile Arg Ala Asn Gln Lys Phe
                50                  55                  60

Arg Asp Arg Val Thr Ile Thr Val Asp Thr Ser Thr Ser Thr Ala Tyr
65              70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
                100                 105                 110

Leu Val Thr Val Ser Ser Cys Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240
```

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 33
<211> LENGTH: 8
<212> TYPE: PRT
<213> ORGANISM: homo sapiens

<400> SEQUENCE: 33

Tyr Gly Ala Thr Ser Leu Glu Thr
1               5

<210> SEQ ID NO 34
<211> LENGTH: 9
<212> TYPE: PRT
<213> ORGANISM: homo sapiens

<400> SEQUENCE: 34

Gln Gln Tyr Trp Thr Thr Pro Phe Thr
1               5

<210> SEQ ID NO 35
<211> LENGTH: 11
<212> TYPE: PRT
<213> ORGANISM: homo sapiens

<400> SEQUENCE: 35

Gly Tyr Ser Ile Thr Asn Asp Tyr Ala Trp Asn
1               5                   10

<210> SEQ ID NO 36
<211> LENGTH: 17
<212> TYPE: PRT
<213> ORGANISM: homo sapiens

<400> SEQUENCE: 36

```
Gly Tyr Ile Ser Tyr Ser Gly Tyr Thr Thr Tyr Asn Pro Ser Leu Lys
1               5                   10                  15

Ser

<210> SEQ ID NO 37
<211> LENGTH: 9
<212> TYPE: PRT
<213> ORGANISM: homo sapiens

<400> SEQUENCE: 37

Ala Arg Trp Ala Ser Gly Leu Asp Tyr
1               5

<210> SEQ ID NO 38
<211> LENGTH: 108
<212> TYPE: PRT
<213> ORGANISM: homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 39
<211> LENGTH: 116
<212> TYPE: PRT
<213> ORGANISM: homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115
```

```
<210> SEQ ID NO 40
<211> LENGTH: 11
<212> TYPE: PRT
<213> ORGANISM: homo sapiens

<400> SEQUENCE: 40

Gly Tyr Ser Ile Thr Ser Asp Tyr Ala Trp Asn
1               5                   10

<210> SEQ ID NO 41
<211> LENGTH: 17
<212> TYPE: PRT
<213> ORGANISM: homo sapiens

<400> SEQUENCE: 41

Gly Tyr Ile Ser Asn Ser Gly Ser Thr Ser Tyr Asn Pro Ser Leu Lys
1               5                   10                  15

Ser

<210> SEQ ID NO 42
<211> LENGTH: 15
<212> TYPE: PRT
<213> ORGANISM: homo sapiens

<400> SEQUENCE: 42

Glu Arg Asn Tyr Asp Tyr Asp Asp Tyr Tyr Ala Met Asp Tyr
1               5                   10                  15

<210> SEQ ID NO 43
<211> LENGTH: 17
<212> TYPE: PRT
<213> ORGANISM: homo sapiens

<400> SEQUENCE: 43

Lys Ser Ser Gln Ser Leu Leu Tyr Arg Ser Asn Gln Lys Asn Tyr Leu
1               5                   10                  15

Ala

<210> SEQ ID NO 44
<211> LENGTH: 7
<212> TYPE: PRT
<213> ORGANISM: homo sapiens

<400> SEQUENCE: 44

Trp Ala Ser Thr Arg Glu Ser
1               5

<210> SEQ ID NO 45
<211> LENGTH: 9
<212> TYPE: PRT
<213> ORGANISM: homo sapiens

<400> SEQUENCE: 45

Gln Gln Tyr Tyr Asn Tyr Pro Arg Thr
1               5

<210> SEQ ID NO 46
<211> LENGTH: 124
<212> TYPE: PRT
<213> ORGANISM: homo sapiens

<400> SEQUENCE: 46

Glu Val Gln Leu Val Glu Ser Gly Gly Gly Leu Val Gln Pro Gly Gly
1               5                   10                  15
```

```
Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
            35                  40                  45

Val Gly Tyr Ile Ser Asn Ser Gly Ser Thr Ser Tyr Asn Pro Ser Leu
 50                  55                  60

Lys Ser Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Glu Arg Asn Tyr Asp Tyr Asp Asp Tyr Tyr Ala Met Asp
            100                 105                 110

Tyr Trp Gly Gln Gly Thr Leu Val Thr Val Ser Ser
            115                 120
```

<210> SEQ ID NO 47
<211> LENGTH: 113
<212> TYPE: PRT
<213> ORGANISM: homo sapiens

<400> SEQUENCE: 47

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
             85                  90                  95

Tyr Tyr Asn Tyr Pro Arg Thr Phe Gly Gln Gly Thr Lys Val Glu Ile
            100                 105                 110

Lys
```

<210> SEQ ID NO 48
<211> LENGTH: 10
<212> TYPE: PRT
<213> ORGANISM: homo sapiens

<400> SEQUENCE: 48

```
Gly Phe Ser Phe Ser Asp Phe Ala Met Ser
 1               5                  10
```

<210> SEQ ID NO 49
<211> LENGTH: 18
<212> TYPE: PRT
<213> ORGANISM: homo sapiens

<400> SEQUENCE: 49

```
Ala Thr Ile Gly Arg Val Ala Phe His Thr Tyr Tyr Pro Asp Ser Met
 1               5                  10                  15

Lys Gly
```

<210> SEQ ID NO 50

```
<211> LENGTH: 13
<212> TYPE: PRT
<213> ORGANISM: homo sapiens

<400> SEQUENCE: 50

Ala Arg His Arg Gly Phe Asp Val Gly His Phe Asp Phe
1               5                   10

<210> SEQ ID NO 51
<211> LENGTH: 16
<212> TYPE: PRT
<213> ORGANISM: homo sapiens

<400> SEQUENCE: 51

Arg Ser Ser Glu Thr Leu Val His Ser Gly Asn Thr Tyr Leu Glu
1               5                   10                  15

<210> SEQ ID NO 52
<211> LENGTH: 7
<212> TYPE: PRT
<213> ORGANISM: homo sapiens

<400> SEQUENCE: 52

Arg Val Ser Asn Arg Phe Ser
1               5

<210> SEQ ID NO 53
<211> LENGTH: 9
<212> TYPE: PRT
<213> ORGANISM: homo sapiens

<400> SEQUENCE: 53

Phe Gln Gly Ser Phe Asn Pro Leu Thr
1               5

<210> SEQ ID NO 54
<211> LENGTH: 120
<212> TYPE: PRT
<213> ORGANISM: homo sapiens

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120

<210> SEQ ID NO 55
<211> LENGTH: 113
<212> TYPE: PRT
<213> ORGANISM: homo sapiens
```

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg

<210> SEQ ID NO 56
<211> LENGTH: 117
<212> TYPE: PRT
<213> ORGANISM: homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 57
<211> LENGTH: 112
<212> TYPE: PRT
<213> ORGANISM: homo sapiens

<400> SEQUENCE: 57

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser

```
                65                  70                  75                  80
Ser Leu Gln Pro Glu Asp Phe Ala Thr Tyr Tyr Cys Gln Gln Ser Asn
                    85                  90                  95
Glu Asp Pro Leu Thr Phe Gly Gln Gly Thr Lys Val Glu Ile Lys Arg
            100                 105                 110

<210> SEQ ID NO 58
<211> LENGTH: 10
<212> TYPE: PRT
<213> ORGANISM: homo sapiens

<400> SEQUENCE: 58

Gly Tyr Thr Phe Ser Ser Tyr Trp Ile Glu
1               5                   10

<210> SEQ ID NO 59
<211> LENGTH: 18
<212> TYPE: PRT
<213> ORGANISM: homo sapiens

<400> SEQUENCE: 59

Gly Glu Ile Leu Pro Gly Gly Gly Asp Thr Asn Tyr Asn Glu Ile Phe
1               5                   10                  15
Lys Gly

<210> SEQ ID NO 60
<211> LENGTH: 10
<212> TYPE: PRT
<213> ORGANISM: homo sapiens

<400> SEQUENCE: 60

Thr Arg Arg Val Pro Ile Arg Leu Asp Tyr
1               5                   10

<210> SEQ ID NO 61
<211> LENGTH: 15
<212> TYPE: PRT
<213> ORGANISM: homo sapiens

<400> SEQUENCE: 61

Lys Ala Ser Gln Ser Val Asp Tyr Glu Gly Asp Ser Phe Leu Asn
1               5                   10                  15

<210> SEQ ID NO 62
<211> LENGTH: 7
<212> TYPE: PRT
<213> ORGANISM: homo sapiens

<400> SEQUENCE: 62

Ala Ala Ser Asn Leu Glu Ser
1               5

<210> SEQ ID NO 63
<211> LENGTH: 9
<212> TYPE: PRT
<213> ORGANISM: homo sapiens

<400> SEQUENCE: 63

Gln Gln Ser Asn Glu Asp Pro Leu Thr
1               5

<210> SEQ ID NO 64
<211> LENGTH: 219
```

<212> TYPE: PRT
<213> ORGANISM: homo sapiens

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 65
<211> LENGTH: 450
<212> TYPE: PRT
<213> ORGANISM: homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Thr Lys Gly Pro Ser Val
        115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 66
<211> LENGTH: 16
<212> TYPE: PRT
<213> ORGANISM: homo sapiens

<400> SEQUENCE: 66

Arg Ser Ser Gln Ser Ile Val His Ser Val Gly Asn Thr Phe Leu Glu
1               5                   10                  15

<210> SEQ ID NO 67
<211> LENGTH: 7
<212> TYPE: PRT
<213> ORGANISM: homo sapiens
```

<400> SEQUENCE: 67

Lys Val Ser Asn Arg Phe Ser
1               5

<210> SEQ ID NO 68
<211> LENGTH: 9
<212> TYPE: PRT
<213> ORGANISM: homo sapiens

<400> SEQUENCE: 68

Phe Gln Gly Ser Gln Phe Pro Tyr Thr
1               5

<210> SEQ ID NO 69
<211> LENGTH: 10
<212> TYPE: PRT
<213> ORGANISM: homo sapiens

<400> SEQUENCE: 69

Gly Tyr Glu Phe Ser Arg Ser Trp Met Asn
1               5                   10

<210> SEQ ID NO 70
<211> LENGTH: 17
<212> TYPE: PRT
<213> ORGANISM: homo sapiens

<400> SEQUENCE: 70

Arg Ile Tyr Pro Gly Asp Gly Asp Thr Asn Tyr Ser Gly Lys Phe Lys
1               5                   10                  15

Gly

<210> SEQ ID NO 71
<211> LENGTH: 11
<212> TYPE: PRT
<213> ORGANISM: homo sapiens

<400> SEQUENCE: 71

Asp Gly Ser Ser Trp Asp Trp Tyr Phe Asp Val
1               5                   10

<210> SEQ ID NO 72
<211> LENGTH: 113
<212> TYPE: PRT
<213> ORGANISM: homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys

Arg

<210> SEQ ID NO 73
<211> LENGTH: 120
<212> TYPE: PRT
<213> ORGANISM: homo sapiens

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser
        115                 120

<210> SEQ ID NO 74
<211> LENGTH: 219
<212> TYPE: PRT
<213> ORGANISM: homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 75
<211> LENGTH: 450
<212> TYPE: PRT
<213> ORGANISM: homo sapiens

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 76
<211> LENGTH: 16
<212> TYPE: PRT
<213> ORGANISM: homo sapiens

<400> SEQUENCE: 76

Arg Ser Ser Gln Ser Leu Leu His Ser Asn Gly Tyr Asn Tyr Leu Asp
1               5                   10                  15

<210> SEQ ID NO 77
<211> LENGTH: 7
<212> TYPE: PRT
<213> ORGANISM: homo sapiens

<400> SEQUENCE: 77

Leu Gly Val Asn Ser Val Ser
1               5

<210> SEQ ID NO 78
<211> LENGTH: 5
<212> TYPE: PRT
<213> ORGANISM: homo sapiens

<400> SEQUENCE: 78

Asn His Ala Ile Ser
1               5

<210> SEQ ID NO 79
<211> LENGTH: 17
<212> TYPE: PRT
<213> ORGANISM: homo sapiens

<400> SEQUENCE: 79

Gly Ile Ile Pro Ile Phe Gly Thr Ala Asn Tyr Ala Gln Lys Phe Gln
1               5                   10                  15
Gly

<210> SEQ ID NO 80
<211> LENGTH: 8
<212> TYPE: PRT
<213> ORGANISM: homo sapiens

<400> SEQUENCE: 80

Glu Trp Ala Asp Val Phe Asp Ile
1               5
```

<210> SEQ ID NO 81
<211> LENGTH: 8
<212> TYPE: PRT
<213> ORGANISM: homo sapiens

<400> SEQUENCE: 81

Glu Trp Ala Asp Val Phe Asp Ile
1               5

<210> SEQ ID NO 82
<211> LENGTH: 112
<212> TYPE: PRT
<213> ORGANISM: homo sapiens

<400> SEQUENCE: 82

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 83
<211> LENGTH: 117
<212> TYPE: PRT
<213> ORGANISM: homo sapiens

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 84
<211> LENGTH: 11
<212> TYPE: PRT
<213> ORGANISM: homo sapiens

```
<400> SEQUENCE: 84

Arg Ala Ser Gln Gly Ile Arg Asn Asp Leu Gly
1               5                   10

<210> SEQ ID NO 85
<211> LENGTH: 7
<212> TYPE: PRT
<213> ORGANISM: homo sapiens

<400> SEQUENCE: 85

Ala Ala Ser Ser Leu Gln Ser
1               5

<210> SEQ ID NO 86
<211> LENGTH: 5
<212> TYPE: PRT
<213> ORGANISM: homo sapiens

<400> SEQUENCE: 86

Gly Asn Tyr Met Ser
1               5

<210> SEQ ID NO 87
<211> LENGTH: 5
<212> TYPE: PRT
<213> ORGANISM: homo sapiens

<400> SEQUENCE: 87

Gly Asn Tyr Met Ser
1               5

<210> SEQ ID NO 88
<211> LENGTH: 16
<212> TYPE: PRT
<213> ORGANISM: homo sapiens

<400> SEQUENCE: 88

Leu Ile Tyr Ser Gly Asp Ser Thr Tyr Tyr Ala Asp Ser Val Lys Gly
1               5                   10                  15

<210> SEQ ID NO 89
<211> LENGTH: 10
<212> TYPE: PRT
<213> ORGANISM: homo sapiens

<400> SEQUENCE: 89

Asp Gly Tyr Tyr Val Ser Asp Met Val Val
1               5                   10

<210> SEQ ID NO 90
<211> LENGTH: 107
<212> TYPE: PRT
<213> ORGANISM: homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 91
<211> LENGTH: 118
<212> TYPE: PRT
<213> ORGANISM: homo sapiens

<400> SEQUENCE: 91

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 92
<211> LENGTH: 107
<212> TYPE: PRT
<213> ORGANISM: homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 93
<211> LENGTH: 118
<212> TYPE: PRT
<213> ORGANISM: homo sapiens

<400> SEQUENCE: 93

```
Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
            115
```

<210> SEQ ID NO 94
<211> LENGTH: 107
<212> TYPE: PRT
<213> ORGANISM: homo sapiens

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
                100                 105
```

<210> SEQ ID NO 95
<211> LENGTH: 118
<212> TYPE: PRT
<213> ORGANISM: homo sapiens

<400> SEQUENCE: 95

```
Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95
```

```
Arg Asp Gly Tyr Tyr Val Ser Asp Met Val Val Trp Gly Lys Gly Thr
                100                 105                 110

Thr Val Thr Val Ser Ser
        115

<210> SEQ ID NO 96
<211> LENGTH: 107
<212> TYPE: PRT
<213> ORGANISM: homo sapiens

<400> SEQUENCE: 96

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 97
<211> LENGTH: 118
<212> TYPE: PRT
<213> ORGANISM: homo sapiens

<400> SEQUENCE: 97

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
                20                  25                  30

Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
50                  55                  60

Gly Arg Phe Ala Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
        115

<210> SEQ ID NO 98
<211> LENGTH: 1255
<212> TYPE: PRT
<213> ORGANISM: homo sapiens

<400> SEQUENCE: 98

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
```

-continued

```
                    20                  25                  30
Leu Arg Leu Pro Ala Ser Pro Glu Thr His Leu Asp Met Leu Arg His
                35                  40                  45
Leu Tyr Gln Gly Cys Gln Val Val Gln Gly Asn Leu Glu Leu Thr Tyr
            50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                        85                  90                  95
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
                115                 120                 125
Val Thr Gly Ala Ser Pro Gly Gly Leu Arg Glu Leu Gln Leu Arg Ser
                130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
                210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
                290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
                370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
```

```
Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860
```

```
Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255
```